US008778348B2

(12) United States Patent
Knapp et al.

(10) Patent No.: US 8,778,348 B2
(45) Date of Patent: Jul. 15, 2014

(54) TRYPANOSOMA ANTIGENS, VACCINE COMPOSITIONS, AND RELATED METHODS

(75) Inventors: Elisabeth Knapp, Newark, DE (US); Vidadi Yusibov, Havertown, PA (US)

(73) Assignee: iBio Inc., Newark, DE (US)

( * ) Notice: Subject to any disclaimer, the term of this patent is extended or adjusted under 35 U.S.C. 154(b) by 596 days.

(21) Appl. No.: 12/110,877

(22) Filed: Apr. 28, 2008

(65) Prior Publication Data
US 2009/0324634 A1 Dec. 31, 2009

Related U.S. Application Data

(60) Provisional application No. 60/914,734, filed on Apr. 28, 2007, provisional application No. 60/984,945, filed on Nov. 2, 2007.

(51) Int. Cl.
*A61K 39/00* (2006.01)

(52) U.S. Cl.
USPC .......... 424/184.1; 424/185.1; 424/186.1; 424/190.1; 424/192.1; 424/201.1; 424/269.1; 530/350

(58) Field of Classification Search
None
See application file for complete search history.

(56) References Cited

U.S. PATENT DOCUMENTS

| | | | |
|---|---|---|---|
| 4,196,265 A | 4/1980 | Koprowski et al. |
| 4,270,537 A | 6/1981 | Romaine |
| 4,596,556 A | 6/1986 | Morrow et al. |
| 4,653,728 A | 3/1987 | Mochizuki et al. |
| 4,790,824 A | 12/1988 | Morrow et al. |
| 4,816,567 A | 3/1989 | Cabilly et al. |
| 4,886,499 A | 12/1989 | Cirelli et al. |
| 4,935,496 A | 6/1990 | Kudo et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,223,409 A | 6/1993 | Ladner et al. |
| 5,312,335 A | 5/1994 | McKinnon et al. |
| 5,316,931 A | 5/1994 | Donson et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,403,484 A | 4/1995 | Ladner et al. |
| 5,417,662 A | 5/1995 | Hjertman et al. |
| 5,427,908 A | 6/1995 | Dower et al. |
| 5,466,220 A | 11/1995 | Brennerman |
| 5,480,381 A | 1/1996 | Weston |
| 5,502,167 A | 3/1996 | Waldmann et al. |
| 5,503,627 A | 4/1996 | McKinnon et al. |
| 5,520,639 A | 5/1996 | Peterson et al. |
| 5,527,288 A | 6/1996 | Gross et al. |
| 5,530,101 A | 6/1996 | Queen et al. |
| 5,545,806 A | 8/1996 | Lonberg et al. |
| 5,545,807 A | 8/1996 | Surani et al. |
| 5,558,864 A | 9/1996 | Bendig et al. |
| 5,565,332 A | 10/1996 | Hoogenboom et al. |
| 5,569,189 A | 10/1996 | Parsons |
| 5,569,825 A | 10/1996 | Lonberg et al. |
| 5,580,717 A | 12/1996 | Dower et al. |
| 5,585,089 A | 12/1996 | Queen et al. |
| 5,591,828 A | 1/1997 | Bosslet et al. |
| 5,599,302 A | 2/1997 | Lilley et al. |
| 5,625,126 A | 4/1997 | Lonberg et al. |
| 5,633,425 A | 5/1997 | Lonberg et al. |
| 5,639,641 A | 6/1997 | Pedersen et al. |
| 5,649,912 A | 7/1997 | Peterson |
| 5,658,727 A | 8/1997 | Barbas et al. |
| 5,661,016 A | 8/1997 | Lonberg et al. |
| 5,667,988 A | 9/1997 | Barbas et al. |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,698,426 A | 12/1997 | Huse et al. |
| 5,702,892 A | 12/1997 | Mulligan-Kehoe |
| 5,704,911 A | 1/1998 | Parsons |
| 5,705,154 A | 1/1998 | Dalie et al. |
| 5,733,743 A | 3/1998 | Johnson et al. |
| 5,750,078 A | 5/1998 | Shitara et al. |
| 5,759,817 A | 6/1998 | Barbas |
| 5,770,403 A | 6/1998 | Dalie et al. |
| 5,770,429 A | 6/1998 | Lonberg et al. |
| 5,855,866 A | 1/1999 | Thorpe et al. |

(Continued)

FOREIGN PATENT DOCUMENTS

| | | |
|---|---|---|
| CZ | 20 031 859 | 2/2005 |
| EP | 404097 | 6/1990 |

(Continued)

OTHER PUBLICATIONS

Li et al. (Parasite Immunology, 2007, 29:191-199, published online Jan. 2007).*
Yusibov et al. (PNAS 94:5784-5788, 1997).*
Rasooly et al. (Vaccine 22:1007-1015, 2004).*
Uniprot database accession No. P04107 Nov. 1, 1986.*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Greenspan et al (Nature Biotechnology 7: 936-937, 1999).*
Chothia et al (The EMBO Journal, 1986, 5/4:823-26).*

(Continued)

*Primary Examiner* — Jennifer Graser
(74) *Attorney, Agent, or Firm* — Fish & Richardson P.C.

(57) ABSTRACT

The present invention relates to the intersection of the fields of immunology and protein engineering, and particularly to antigens and vaccines useful in prevention of infection by *Trypanosoma* protozoa. Provided are recombinant protein antigens, compositions, and methods for the production and use of such antigens and vaccine compositions.

23 Claims, 15 Drawing Sheets

(56) References Cited

U.S. PATENT DOCUMENTS

| | | | |
|---|---|---|---|
| 5,877,289 A | 3/1999 | Thorpe et al. | |
| 5,888,789 A | 3/1999 | Rodriguez et al. | |
| 5,893,397 A | 4/1999 | Peterson et al. | |
| 5,965,132 A | 10/1999 | Thorpe et al. | |
| 5,993,412 A | 11/1999 | Deily et al. | |
| 6,004,555 A | 12/1999 | Thorpe et al. | |
| 6,042,832 A | 3/2000 | Koprowski et al. | |
| 6,093,399 A | 7/2000 | Thorpe et al. | |
| 6,103,511 A | 8/2000 | Li et al. | |
| 6,261,535 B1 | 7/2001 | Thorpe et al. | |
| 6,524,825 B1 | 2/2003 | Mizzen et al. | |
| 6,649,172 B2 | 11/2003 | Johnson | |
| 6,740,740 B2 | 5/2004 | Garger et al. | |
| 6,797,491 B2 | 9/2004 | Neefe, Jr. et al. | |
| 6,841,659 B2 | 1/2005 | Turpen et al. | |
| 7,888,135 B2 * | 2/2011 | Tarleton et al. | 436/518 |
| 2004/0093643 A1 | 5/2004 | Ensle | |
| 2004/0170606 A1 | 9/2004 | Palmer et al. | |
| 2004/0268442 A1 | 12/2004 | Miller et al. | |
| 2005/0026291 A1 | 2/2005 | Fedorkin et al. | |
| 2005/0042229 A1 | 2/2005 | Yang et al. | |
| 2005/0048074 A1 | 3/2005 | Cardineau et al. | |
| 2005/0186621 A1 | 8/2005 | Galarza et al. | |
| 2006/0008473 A1 | 1/2006 | Yang et al. | |
| 2006/0265787 A1 | 11/2006 | Piruzian et al. | |
| 2008/0124272 A1 | 5/2008 | Yusibov et al. | |
| 2008/0279877 A1 | 11/2008 | Yusibov et al. | |
| 2010/0227373 A1 | 9/2010 | Yusibov et al. | |
| 2011/0027304 A1 | 2/2011 | Yusibov et al. | |
| 2011/0059130 A1 | 3/2011 | Yusibov | |

FOREIGN PATENT DOCUMENTS

| | | |
|---|---|---|
| WO | WO9311161 | 6/1993 |
| WO | WO9602555 | 2/1996 |
| WO | WO9612028 | 4/1996 |
| WO | WO9713537 | 4/1997 |
| WO | WO9737705 | 10/1997 |
| WO | WO9814595 | 4/1998 |
| WO | WO9845331 | 10/1998 |
| WO | WO9907860 | 2/1999 |
| WO | WO0020612 | 4/2000 |
| WO | WO0025574 | 5/2000 |
| WO | WO0046350 | 8/2000 |
| WO | WO03040179 | 5/2003 |
| WO | WO03057834 | 7/2003 |
| WO | WO2004043886 | 5/2004 |
| WO | WO2005026375 | 3/2005 |
| WO | WO2005049839 | 6/2005 |
| WO | WO2005067620 | 7/2005 |
| WO | WO2005081905 | 9/2005 |
| WO | WO2006003018 | 1/2006 |
| WO | WO2006124712 | 11/2006 |
| WO | WO2007089753 | 8/2007 |
| WO | WO2007095304 | 8/2007 |
| WO | WO2007095318 | 8/2007 |
| WO | WO2007149715 | 12/2007 |
| WO | WO2008021959 | 2/2008 |
| WO | WO2008033105 | 3/2008 |
| WO | WO2008033159 | 3/2008 |
| WO | WO2008048945 | 4/2008 |
| WO | WO2008110937 | 9/2008 |
| WO | WO2008134643 | 11/2008 |
| WO | WO2009009759 | 1/2009 |
| WO | WO2009026397 | 2/2009 |
| WO | WO2009054708 | 4/2009 |
| WO | WO2009058355 | 5/2009 |
| WO | WO2010036970 | 4/2010 |
| WO | WO2010037046 | 4/2010 |

OTHER PUBLICATIONS

Ahlquist et al., "Gene Expression Vectors Derived from Plant RNA Viruses", *Current Communications in Molecular Biology—Viral Vectors*, (Ed., Gluzman et al.) 183-189, 1988.

Akol and Murray, "*Trypanosoma congolense*: Susceptibility of cattle to cyclical challenge," *Exp. Parasitol.*, 55:386-393, 1983.

Barfield et al., "Gene Transfer in Plants of *Brassica juncea* Using *Agrobacterium tumefaciens* Mediated Transformation", *Plant Cell Reports* 1991, 10(6/7): 308-14.

Bates, "Genetic Transformation of Plants by Protoplast Electroporation", *Molecular Biotechnol.*, 1994, 2(2):135-145.

Beachy et al., "A Genetic Map for the Cowpea Strain of TMV" *Virology* 1976, 73: 498-507.

Bisaro et al., Genetic Analysis of Tomato Golden Mosaic Virus, *Current Communications in Molecular Biology—Viral Vectors*, (Ed., Gluzman et al.) 1988, 172-177.

Bol et al., "A Functional Equivalence of Top Component a RNA and Coat Protein in the Initiation of Infection by Alfalfa Mosaic Virus" *Virology* 1971, 46: 73-85.

Bol et al., "Alfalfa Mosaic Virus and Ilarviruses: Involvement of Coat Protein in Multiple Steps of the Replication Cycle" *J. Gen. Virol.* 1999, 80: 1089-1102.

Bruening et al., "In Vitro and in Vivo Translation of the Ribonucleic Acids of a Cowpea Strain of Tobacco Mosaic Virus" *Virology* 1976, 71: 498-517.

Canizares et al., "Use of viral vectors for vaccine production in plants", *Immunol. Cell Biol.*, 2005, 83:263-270.

Chen et al., "Complete sequence of the binary vector pB1121 and its application in cloning T-DNA insertion from transgenic plants", *Mol. Breed.*, 2003, 11, 287-293.

Chichester et al., "Immunogenicity of a subunit vaccine against *Bacillus anthracis*", *Vaccine*, 2007, 25:3111-3114.

Crossway, A., et al., "Integration of foreign DNA following microinjection of tobacco mesophyll protoplasts", *Mol. Gen. Genet.*, 1986, 202:179-185.

Curtis and Nam, "Transgenic radish (*Raphanus sativus* L. *longipinnatus* Bailey) by floral-dip method—plant development and surfactant are important in optimizing transformation efficiency", *Transgenic Research*, 2001, 10(4):363-371.

Dawson et al., "cDNA cloning of the complete genome of tobacco mosaic virus and production of infectious transcripts", *Proc. Natl Acad. Sci., USA*, 1986, 83:1832.

Desfeux et al., "Female Reproductive Tissues Are the Primary Target of *Agrobacterium*-Mediated Transformation by the *Arabidopsis* Floral-Dip Method", *Plant Physiology*, 2000, 123(3):895-904.

Fraley et al., "Expression of Bacterial Genes in Plant Cells" *Proc. Natl. Acad. Sci. USA* 1983, 80: 4803-4807.

Fraley et al., "Liposome-Mediated Delivery of Tobacco Mosaic Virus RNA Into Tobacco Protoplasts: A Sensitive Assay for Monitoring Liposome-Protoplast Interactions" *Proc. Natl. Acad. Sci. USA* 1982, 79: 1859-1863.

Fromm et al., "Expression of Genes Transferred Into Monocot and Dicot Plant Cells by Electroporation" *Proc. Natl. Acad. Sci. USA* 1985, 82: 5824, 1985.

Fütterer et al., "Use of DNA Plant Viruses and Plant Viral Expression Signals for Gene Expression in Plants and Plant Protoplasts", *Current Communications in Molecular Biology—Viral Vectors*, (Ed., Gluzman et al.) 1988, 178-182.

Gelvin, "*Agrobacterium*-Mediated Plant Transformation: the Biology behind the 'Gene-Jockeying' Tool", *Microbiol. Mol Biol. Rev.*, 2003, 67(1):16-37.

Giri and Narasu, "Transgenic hairy roots: recent trends and applications", *Biotechnol. Adv.*, 2000, 18:1-22.

Gluzman et al., *Communications in Molecular Biology: Viral Vectors*, Cold Spring Harbor Laboratory, Cold Spring Harbor, NY, pp. 172-189, 1988.

Goldenkova et al., "A Thermostable *Clostridium thermocellum* Lichenase-based Reporter System for Studying the Gene Expression Regulation in Prokaryotic and Eukaryotic Cells", *Mol. Biol.*, 2002, 36:698-704.

Grierson et al., "Plant Viruses", *Plant Molecular Biology*, Blackie, London, pp. 126-146, 1984.

Hahn et al., "Native-like in-vivo folding of a circularly permuted jellyroll protein shown by crystal structure analysis", *Proc. Natl. Acad. Sci., USA*, 1994, 91(22):10417-10421.

(56) References Cited

OTHER PUBLICATIONS

Hellens et al., "pGreen: a versatile and flexible binary Ti vector for *Agrobacterium*-mediated plant transformation" *Plant Molecular Biology* 2000, 42: 819-832.
Herbert and Lumsden, "*Trypanosoma brucei*: A rapid 'matching' method for estimating the host's parasitemia," *Exp. Parasitol*, 40:427, 1976.
Hunter et al., "Messenger RNA for the Coat Protein of Tobacco Mosaic Virus" *Nature* 1976, 260: 759-760.
Ishikawa et al., "In Vitro Mutagenesis of the Putative Replicase Genes of Tobacco Mosaic Virus" *Nucleic Acids Res*. 1986, 14: 8291-8308.
Jaspars et al., "Plant Viruses With a Multipartite Genome" *Adv. Virus Res*. 1974, 19: 37-149.
Kapila et al., "An *Agrobacterium*-mediated transient gene expression system for intact leaves", *Plant Sci*., 1997, 122:101-108.
Kapusta et al., "A plant-derived edible vaccine against hepatitis B virus", *FASEB J.*, 1999, 13:1796-1799.
Kikkert et al., "Biological Projectiles (Phage, Yeast, Bacteria) for Genetic Transformation of Plants", *In Vitro Cell. Dev. Bio.—Plant*, 1999. 35(1):43-50.
Klein et al., "High-velocity microprojectiles for delivering nucleic acids into living cells", *Nature*, May 7, 1987, 327:70-73.
Knapp et al., "Conundrum of the Lack of Defective RNAs (dRNAs) Associated with Tobamovirus Infections: dRNAs That Can Move Are Not Replicated by the Wild-Type Virus; dRNAs That Are Replicated by the Wild-Type Virus Do Not Move", *J. Virol*., 2001, 75:5518.
Knudsen and Muller, "Transformation of the developing barley endosperm by particle bombardment", *Planta*, 1991, 185:330-336.
Krens et al., "In vitro transformation of plant protoplasts with Ti-plasmid DNA", *Nature*, 1982, 296:72-74.
Kumagai, et al., "Rapid, High-Level Expression of Glycosylated Rice α-Amylase in Transfected Plants by an RNA Viral Vector" *Gene* 2000, 245: 169-174.
Lawton et al., "Expression of a Soybean (3-Conclycinin Gene Under the Control of the Cauliflower Mosaic Virus Virus 35S and 19S Promoters in Transformed Petunia Tissues" *Plant Mol. Biol* 1987, 9: 315-324.
Lewandowski and Dawson, "Deletion of Internal Sequences Results in Tobacco Mosaic Virus Defective RNAs That Accumulate to High Levels without Interfering with Replication of the Helper Virus", *Virology*, 1998, 251:427-437.
Loesch-Fries, et al., "Expression of Alfalfa Mosaic Virus RNA 4 cDNA Transcripts in Vitro and in Vivo" *Virology* 1985, 146: 177-187.
Lubega et al , "Immunization with a tubulin-rich preparation from *Trypanosoma brucei* confers broad protection against African trypanosomosis," *Exp. Parasitol.*, 2002, 102:9-22.
Lubega et al., "*Trypanosoma brucei*: anti-tubulin antibodies specifically inhibit trypanosome growth in culture," *Exp. Parasitol*., 2002, 102:134-142.
McCormick et al., "Rapid Production of Specific Vaccines for Lymphoma by Expression of the Tumor-Derived Single-Chain Fv Epitopes in Tobacco Plants" *Proc. Natl. Acad. Sci. USA* 1999, 96: 703-708.
Mathew, *Plant Viruses Online—Cassava Indian mosaic bigeminvirus* (http://imagels.uidaho.eduivide/), downloaded on Feb. 21, 2006, 5 pgs.
Meshi et al., "Function of the 30 kd Protein of Tobacco Mosaic Virus: Involvement in Cell-To-Cell Movement and Dispensability for Replication" *EMBO J.* 1987, 6: 2557-63.
Modelska et al., "Immunization against rabies with plant-derived antigen", *Proc. Nati. Acad. Sci., USA*, 1998, 95:2481-2485.
Musiychuk et al., "A launch vector for the production of vaccine antigens in plants", *Influenza and Other Respiratory Viruses*, 2007, 1:1.
Neeleman et al., "Role of Alfalfa Mosaic Virus Coat Protein Gene in Symptom Formation" *Virology* 1991, 181: 687-693.
Neeleman et al., "Infection of Tobacco With Alfalfa Mosaic Virus cDNAs Sheds Light on the Early Function of the Coat Protein" *Virology* 1993, 196: 883-887.

Peres et al., 2001 , "Shoot regeneration capacity from roots and transgenic hairy roots of tomato cultivars and wild related species", *Plant Cell, Tissue, and Organ Culture*, 2001, 65:37-44.
Pilon-Smits et al., "Overexpression of ATP Sulfurylase in Indian Mustard Leads to Increased Selenate Uptake, Reduction, and Tolerance" *Plant Physiol*. 1999, 119(1): 123-132.
Qing et al., "Transformation of Pakchoi (*Brassica rapa* L. ssp. *chinensis*) by *Agrobacterium* Infiltration", *Molecular Breeding*, 2000, 1:67-72.
Rao and Ravishankar, "Plant cell cultures: Chemical factories of secondary metabolites", *Biotechnol. Adv.*, 2002, 20:101-153.
Riva et al., "*Agrobacterium tumefaciens*: a natural tool for plant transformation", *EJB Electronic J. Biotech.*, 1998, 1(3), 118-133.
Saito, et al., "Long-Distance Movement and Viral Assembly of Tobacco Mosaic Virus Mutants" *Virology* 1990, 176: 329-336.
Schell et al., "Transgenic Plants As Tools to Study the Molecular Organization of Plant Genes." *Science* 1987, 237: 1176-1183.
Tacket et al., "Human Immune Responses to a Novel Norwalk Virus Vaccine Delivered in Transgenic Potatoes", *J. Infect. Dis*., 2000, 182:302-305.
Thanavala et al., "Immunogenicity in humans of an edible vaccine for hepatitis B", *Proc. Natl. Acad. Sci., USA*, 2005, 102:3378-3382.
Turpen et al., "Transfection of whole plants from wounds inoculated with *Agrobacterium tumefaciens* containing cDNA of tobacco mosaic virus", *J. Virol, Methods*, 1993, 42:227.
Van Der Kuyl et al., "Complementation and Recombination between Alfalfa Mosaic Virus RNA3 Mutants in Tobacco Plants", *Virology*, 1991, 183:731-738.
Van Der Kuyl et al., "Role of Alfalfa Mosaic Virus Coat Protein in Regulation of the Balance between Viral Plus and Minus Strand RNA Synthesis" *Virology*, 1991, 185:496-499.
Van Der Vossen, et al., "Early and Late Functions of Alfalfa Mosaic Virus Coat Protein Can Be Mutated Separately" *Virology* 1994, 202: 891-903.
Verch et al., "Expression and assembly of a full-length monoclonal antibody in plants using a plant virus vector", *J. Immunol. Methods*, 1998, 220, 69-75.
Voinnet et al., "An enhanced transient expression system in plants based on suppression of gene silencing by the p19 protein of tomato bushy stunt virus", *The Plant Journal*, (2003) 33: 949-956.
Woo, P. T. K., "The Haematocrit Centrifuge Technique for the Diagnosis of African Trypanosomiasis", *Acta Tropica*, 27:384, 1970.
Yusibov et al., "Expression in plants and immunogenicity of plant virus-based experimental rabies vaccine" *Vaccine*, 2002, 20:3155-3164.
Yusibov et al., "N-Terminal Basic Amino Acids of Alfalfa Mosaic Virus Coat Protein Involed in the Initiation of Infection" *Virology* 1995, 208:405-407.
Yusibov et al., "Purification, characterization, assembly and crystallization of assembled alfalfa mosaic virus coat protein expressed in *Escherichia coli"*, *J. Gen. Virol*., 1996, 77:567-573.
Yusibov et al., "Antigens Produced in Plants by Infection With Chimeric Plant Viruses Immunize Against Rabies Virus and HIV-1" *Proc. Natl. Acad. Sci. USA* 1997, 94: 5784-5788.
Supplementary European Search Report dated Jun. 9, 2010 for European Appln. No. EP 08 78 0572 (5 pgs.).
Accession CAA4959, Apr. 18, 2005.
Air, "Mechanism of antigenic variation in an individual epitope on influenza virus N9 neurammidase," *J. Virology*, 64(12):5797-5803, 1990.
Alignment of 11706573-6 to SEQ ID No. 6 in U.S. Appl. No. 10/558,109 on Feb. 24, 2009.
Alignment of 11706573-30 to SEQ ID No. 6 in U.S. Appl. No. 10/558,109 on Feb. 24, 2009.
Alignment of 11706576-12 to SEQ ID No. 6 in U.S. Appl. No. 10/558,109 on Feb. 24, 2009.
Alignment of 12110877-30 to SEQ ID No. 6 in U.S. Appl. No. 10/558,109 on Feb. 24, 2009.
Alvarez et al., "Plant-made subunit vaccine against pneumonic and bubonic plague is orally immunogenic in mice," *Vaccine*, 24(14):2477-2490, 2006.

(56) References Cited

OTHER PUBLICATIONS

Anderson et al., "Recombinant V antigen protects mice against pneumonic and bubonic plague caused by F1-capsule-positive and -negative strains of *Yersinia pestis*," *Infect. Immun.*, 64(11):4580-5, 1996.
Andrews et al., "Fraction 1 capsular antigen (F1) purification from *Yersinia pestis* CO92 and from an *Escherichia coli* recombinant strain and efficacy against lethal plague challenge," *Infect. Immun.*, 64(6):2180-7, 1996.
Ay et al., "Crystal structures and properties of de novo circularly permuted 1,3-1,4-beta-glucanases," *Proteins*, 30(2):155-67, 1998.
Aymard et al., "Role of antineuraminidase antibodies in protection against influenza," *Bulletin de l'Academie nationale de medicine*, 182(8):1723-1736, 1998.
Aymard et al., "Neuraminidase assays," *Developments in Biologicals*, 115:75-83, 2003.
Barbas et al., "Assembly of combinatorial antibody libraries on phage surfaces: The gene III site," *Proc. Natl. Acad. Sci. USA*, 88:7978, 1991.
Barbas et al., "Semisynthetic combinatorial antibody libraries: A chemical solution to the diversity problem," *Proc. Natl. Acad. Sci. USA*, 89:4457, 1992.
Bedell et al., "The E6-E7 region of human papillomavirus type 18 is sufficient for transformation of NIH 3T3 and Rat-1 cells," *J. Virol.*, 61:3635-40, 1987.
Berger et al., "Therapeutic applications of monoclonal antibodies," *Am J Med Sci.*, 324(1):14-30, 2002.
Boyd and Beeson, "Animal models for evaluation of compounds against influenza viruses," *J. Antimicrob. Chemother.*, 1 (Suppl.), 43-47, 1975.
Brett et al., "Immunization against influenza A virus: comparison of conventional inactivated, live-attenuated and recombinant baculovirus produced purified hemagglutinin and neuraminidase vaccines in a murine model system," *Virology*, 339(2):273-280, 2005.
Broothaerts et al., "Gene transfer to plants by diverse species of bacteria," *Nature*, 433:629-633, 2005.
Brodzik et al., "Advances in alfalfa mosaic virus-mediated expression of anthrax antigen in planta," *Biochem. Biophys. Res. Commun.*, 338(2):717-722, 2005.
Burke et al., "Cloning of large segments of exogenous DNA into yeast by means of artificial chromosome vectors," *Science*, 236:806, 1987.
Buscaglia et al., "Tandem amino acid repeats from *Trypanosoma cruzi* shed antigens increase the half-life of proteins in blood," *Blood*, 93(6):2025-2032, 1999.
Calandrelli et al., "Purification and characterization of thermostable xylanase and beta-xylosidase by the thermophilic bacterium *Bacillus termantarcticus," Res. Microbiol.*, 155(4): 283-9, 2004.
Chain et al., "Complete genome sequence of *Yersinia pestis* strains Antiqua and Nepal516: evidence of gene reduction in an emerging pathogen," *J. Bacteriol.*, 188(12):4453-63, 2006.
Chen et al., "Induction and relief of nasal congestion in ferrets infected with influenza virus," *Int. J. Exp. Path.*, 76:55-64, 1995.
Chica et al., "Semi-rational approaches to engineering enzyme activity: combining the benefits of directed evolution and rational design," *Curr. Opin. Biotechnol.*, 16:378-384, 2005.
Chichester et al., "Immunogenicity of a subunit vaccine against *Bacillus anthracis," Vaccine*, 25:3111-3114, 2007.
Chichester et al., "Different response requirements for IFNγ production in ELISPOT assays by CD4+ T cells from mice early and late after submission," *J. Immunol. Methods*, 309:99-107, 2006.
Corbel, "Reasons for instability of bacterial vaccines," *Developments in Biological Standardization*, 87:113-124, 1996.
Costa et al., "Conformational stability and antibody response to the 18kDa heat-shock protein formulated into different vehicles," *Appl. Biochem. Biotechnol.*, 73(1):19-28, 1998.
DeGraff et al., "In vitro evidence that the coat protein of alfalfa mosaic virus plays a direct role in the regulation of plus and minus RNA synthesis: implications for the life cycle of alfalfa mosaic virus," *Virology*, 208:583-589, 1995.
Deng et al., "Genome sequence of *Yersinia pestis* KIM," *J. Bacteriol.*, 184(16):4601-11, 2002.
Dréau et al., "Human papilloma virus in melanoma biopsy specimens and its relation to melanoma progression," *Ann. Surgery*, 231:664-671, 2000.
Fenton et al., "Immunity to influenza in ferrets. XIV: Comparative immunity following infection or immunization with live or inactivated vaccine," *Br. J. Exp. Path.*, 62:297, 1981.
Fernando et al., "Expression, purification and immunological characterization of the transforming protein E7, from cervical cancer-associated human papillomavirus type 16," *Clin Exp Immunol*, 115:397-403, 1999.
Flick-Smith et al., "A recombinant carboxy-terminal domain of the protective antigen of *Bacillus anthracis* protects mice against anthrax infection," *Infect. Immun.*, 70:1653-1656, 2002.
Floss et al., "Production of vaccines and therapeutic antibodies for veterinary applications in transgenic plants: an overview," *Transgenic Res.*, 16(3):315-332, 2007.
Franconi et al., "Plant-derived human papillomavirus 16 E7 oncoprotein induces immune response and specific tumor production," *Cancer Res.*, 62:3654, 2002.
Gleba et al., "Magnifection—a new platform for expressing recombinant vaccines in plants," *Vaccine*, 23:2042-2048, 2005.
Green et al., "Transient protein expression in three *Pisum sativum* (green pea) varieties," *Biotechnol. J.*, 4(2):230-238, 2009.
Gu et al., "Protection against anthrax toxin by vaccination with a DNA plasmid encoding anthrax protective antigen," *Vaccine*, 17:340, 1999.
Heath et al., "Protection against experimental bubonic and pneumonic plague by a recombinant capsular F1-V antigen fusion protein vaccine," *Vaccine*, 16(11/12):1131-7, 1998.
Hobson et al., "The role of serum haemagglutination-inhibiting antibody in protection against challenge infection with influenza A2 and B viruses," *J. Hyg.*, 70:767, 1972.
Huang et al., "Plant-derived measles virus hemagglutinin protein induces neutralizing antibodies in mice," *Vaccine*, 19(15-16):2163-2171, 2001.
Huber et al., "Distinct contributions of vaccine-induced immunoglobulin G1 (IgG1) and IgG2a antibodies to protective immunity against influenza," *Clin. Vaccine Immunol.*, 13:981-90, 2006.
Hull et al., "Human-derived, plant-produced monoclonal antibody for the treatment of anthrax," *Vaccine*, 23:2082-2086, 2005.
Huse et al., "Generation of a large combinatorial library of the immunoglobulin repertoire in phage lambda," *Science*, 246:1275, 1989.
Jirholt et al., "Exploiting sequence space: shuffling in vivo formed complementarity determining regions into a master framework," *Gene*, 215:471, 1998.
Johnson et al., "Respiratory syncytial virus (RSV) G glycoprotein is not necessary for vaccine-enhanced disease induced by immunization with formalin-inactivated RSV," *J. Virol*, 78(11):6024-32, 2004.
Jones et al., "Replacing the complementarity—determining regions in a human antibody with those from a mouse," *Nature*, 321:522, 1986.
Kang et al., "Linkage of recognition and replication functions by assembling combinatorial antibody Fab libraries along phage surfaces," *Proc. Natl. Acad. Sci. USA*, 88:4363, 1991.
Kao et al., "A method for high-frequency intergeneric fusion of plant protoplasts," *Planta*, 115:355, 1974.
Katayama and Mine, "*Quillaja* saponin can modulate ovalbumin-induced IgE allergic responses through regulation of Th1/Th2 balance in a murine model," *J. Agric. Food Chem.*, 54:3271-6, 2006.
Konieczny et al., "The combination of IgM subunits and proteolytic IgG fragments by controlled formation of interchain disulphides," *Haematologia* (Budap), 14:95, 1981.
Kubler-Kielb et al., "Long-lasting and transmission-blocking activity of antibodies to *Plasmodium falciparum* elicited in mice by protein conjugates of Pfs25," *Proc. Natl. Acad. Sci. USA*, 104(1):293-298, 2007.
Lambkin et al., "Strong local and systemic protective immunity induced in the ferret model by an intranasal virosome-formulated influenza subunit vaccine," *Vaccine*, 22:4390, 2004.

(56) References Cited

OTHER PUBLICATIONS

Lee and Air, "Contacts between influenza virus N9 neuraminidase and monoclonal antibody NC10," *Virol.*, 300(2):255-268, 2002.
Leite et al., "Expression of correctly processed human growth hormone in seeds of transgenic tobacco plants," *Mol. Breeding*, 6:47-53, 2000.
Lensen et al., "Measurement by membrane feeding of reduction in *Plasmodium falciparum* transmission induced by endemic sera," *Trans. R. Soc. Trop. Med. Hyg.*, 90(1):20-2, 1996.
Lim et al., "An anthrax lethal factor-neutralizing monoclonal antibody protects rats before and after challenge with anthrax toxin," *Infect. Immun.*, 73:6547, 2005.
Lin et al., "Treatment of established tumors with a novel vaccine that enhances major histocompatibility class II presentation of tumor antigen," *Cancer Res.*, 56:21,1996.
Little et al., "Passive protection by polyclonal antibodies against *Bacillus anthracis* infection in guinea pigs," *Infect. Immun.*, 65:5171-5175, 1997.
Lorence and Verpoorte, "Gene transfer and expression in plants," *Meth. Mol. Biol.*, 267:329-350, 2004.
Maliga et al., "Transient cycloheximide resistance in a tobacco cell line," *Mol. Gen. Genet.*, 149:267-271, 1976.
Maassab et al., "Evaluation of a cold-recombinant influenza virus vaccine in ferrets," *J. Infect. Dis.*, 146(6):780-790, 1982.
Mbawuike et al., "Humoral and cell-mediated immune responses of humans to inactivated influenza vaccine with or without QS21 adjuvant," *Vaccine*, 25:3263-9, 2007.
McHugh et al., "Improved stability of a protein vaccine through elimination of a partially unfolded state," *Protein Sci.*, 13:2736-2743, 2004.
Mellin et al., "Human papillomavirus (HPV) DNA in tonsillar cancer: clinical correlates, rise of relapse, and survival," *Int. J. Cancer*, 89:300-304, 2000.
Menczel et al., "Streptomycin resistant and sensitive somatic hybrids of *Nicotiana tabacum + Nicotiana knightiana*: correlation of resistance to *N. tabacum* plastids," *Theor. Appl. Genet.*, 59:191-195, 1981.
Mett et al., "A plant-produced influenza subunit vaccine protects ferrets against virus challenge," *Influenza and Other Respiratory Viruses*, 2(1):33-40, 2008.
Mett et al., "Plants as biofactories," *Biologicals: Journal of the International Association of Biological Standardization*, 36(6):354-358, 2008.
Mett et al., "A plant-produced plague vaccine candidate confers protection to monkeys," *Vaccine*, 25(16):3014-3017, 2007.
Moayeri et al., "The roles of anthrax toxin in pathogenesis," *Curr. Opin. Microbiol.*, 7(1):19-24, 2004.
Moreira et al., "A thermostable maltose-tolerant α-anylase from *Asperillgus tamarii*," *J. Basic Microbiol.*, 44:29-35, 2004.
Morrison et al., "Chimeric human antibody molecules: Mouse antigen-binding domains with human constant region domains," *Proc. Natl. Acad. Sci. USA*, 81:6851, 1984.
Morrison et al., "Production of novel immunoglobulin molecules by gene transfection," *Mt. Sinai J. Med.*, 53:175, 1986.
Murashige et al., "A revised medium for rapid growth and bio assays with tobacco tissue cultures," *Physiologia Plantarum*, 15:473, 1962.
Musiychuk et al., "Preparation and properties of *Clostridium thermocellum* lichenase deletion variants and their use for construction of bifunctional hybrid proteins," *Biochem. (MOSC)*, 65(12):1397-1402, 2000.
Nagy et al., "Thermal stability of chemically denatured green fluorescent protein (GFP)—A preliminary study," *Thermochimica Acta*, 410(1), abstract, 2004.
Nass, "Anthrax vaccine—model of a response to the biologic warfare threat," *Infect. Dis. Clin. North Am.*, 13:187-208, 1999.
NCBI GenBank Accession No. ABP96852, "Influenza A virus" (A/Egypt/2616-NAMRU3/2007(H5N1)) hemagglutinin (HA) gene, complete CDS, Apr. 30, 2007.
NCBI GenBank Accession No. AAS93885, "Influenza A virus" (A/Cheju/274/2002(H3N2)) neuraminidase (NA) gene, complete CDS, Apr. 25, 2004.
Park et al., "Molecular biology of cervical cancer and its precursors," *Cancer*, 76:1902-1913, 1995.
Parkhill et al., "Genome sequence of *Yersinia pestis*, the causative agent of plague," *Nature*, 413:523-7, 2001.
Petosa et al., "Crystal structure of the anthrax toxin protective antigen," *Nature*, 385:833-838, 1997.
Piruzian et al., "The use of a thermostable beta-glucanase gene from *Clostridium thermocellum* as a reporter gene in plants," *Mol. Gen. Genet.*, 257:561-567, 1998.
Piruzian et al., "A reporter system for prokaryotic eukaryotic cells based on the thermo-stable lichenase from *Clostridium thermocellum*," *Mol. Gen. Genet.*, 266: 778-786, 2002.
Potter et al., "Immunity to influenza in ferrets II. Influence of adjuvants on immunization," *Br. J. Exp. Pathol.*, 53:168, 1972.
Potter et al., "Immunity to influenza in ferrets VI. Immunization with adjuvanted vaccines," *Arch. Gesamte Virusforsch.*, 42:285, 1973.
Potter et al., "Immunity to influenza in ferrets V. Immunization with inactivated virus in adjuvant 65," *J. Hyg. Lond.*, 71:97, 1973.
Pruett et al., "Critical interactions in binding antibody NC41 to influenza N9 neuraminidase: amino acid contacts on the antibody heavy chain," *Biochem.*, 37:10660-10670, 1998.
Qian et al., "Conjugating recombinant proteins to *Pseudomonas aeruginosa* ExoProtein A: A strategy for enhancing immunogenicity of malaria vaccine candidate," *Vaccine*, 25(20): 3923-3933, 2007.
Reinstein et al., "Degradation of the E7 human papillomavirus oncoprotein by the ubiquitin-proteasome system: targeting via ubiquitination of the N-terminal residue," *Oncogene*, 19:5944-5950, 2000.
Riechmann et al., "Reshaping human antibodies for therapy," *Nature*, 332:323, 1988.
Rowe et al., "Detection of antibody to avian influenza A (H5N1) virus in human serum by using a combination of serologic assays," *J. Clin. Microbiol.*, 37:937-43 , 1999.
Sabbatini et al., "Pilot study of a heptavalent vaccine-keyhole limpet hemocyanin conjugate plus QS21in patients with epithelial ovarian, fallopian tube, or peritoneal cancer," *Clin. Cancer Res.*, 13:4170-7, 2007.
Santi et al., "Protection conferred by recombinant *Yersinia pestis* antigens produced by a rapid and highly scalable plant expression system," *Proc. Natl. Acad. Sci. USA*, 103(4):861-866, 2006.
Saravolac et al "Immunoprophylactic strategies against respiratory influenza virus infection," *Vaccine*, 19:2227-32, 2001.
Scheiblauer et al., "Pathogenicity of influenza A/Seal/Mass/1/80 virus mutants for mammalian species," *Arch Virol*, 140:341-384, 1995.
Schild et al., "A single-radial-immunodiffusion technique for the assay of influenza haemagglutinin antigen—Proposals for an assay method for the haemagglutinin content of influenza vaccines," *Bull. World Health Org.*, 52:223-31, 1975.
Seedorf et al., "Human papillomavirus type 16 DNA sequence," *Virology*, 145:181, 1985.
Sen et al., "Developments in directed evolution for improving enzyme functions," *Appl. Biochem. Biotechnol.*, 143(3):212-23, 2007.
Shima et al., "Hyperthermophilic and salt-dependent formyltransferase from *Methanopyrus kanleri*," *Biochem. Soc. Trans.*, 32:269-72, 2004.
Shimasaki et al., "Rapid diagnostics: the detection of neuraminidase activity as a technology for high-specificity targets," *Philosophical transactions of the Royal Society of London. Series B, Biological Sciences*, 356(1416):1925-1931, 2001.
Shivprasad et al., "Heterologous sequences greatly affect foreign gene expression in tobacco mosaic virus-based vectors," *Virology*, 255(2):312-23, 1999.
Shoji et al., "Immunogenicity of hemagglutinin from A/Bar-headed/Goose/Qinghai/1A/05 and A/Anhui/1/05 strains of H5N1 influenza viruses produced in *Nicotiana benthamiana* plants," *Vaccine*, 27(25-26):3467-3470, 2009.
Shoji et al., "Plant-expressed HA as a seasonal influenza vaccine candidate," *Vaccine*, 26(23):2930-2934, 2008.
Singh et al., "Gln277 and Phe544 residues are involved in thermal inactivation of protective antigen of *Bacillus anthracis*," *Biochem. Biophys. Res. Commun.*, 296:1058-1062, 2002.

(56) References Cited

OTHER PUBLICATIONS

Singh et al., "Study of immunization against anthrax with the purified recombinant protective antigen of *Bacillus anthracis*," *Infect. Immun.*, (66):3447-3448, 1998.
Singh et al., "Thermal inactivation of protective antigen of *Bacillus anthracis* and its prevention by polyol osmolytes," *Biochem. Biophys. Res. Commun.*, 322:1029-1037, 2004.
Smahel et al., "Modified HPV16 E7 genes as DNA vaccine against E7-containing oncogenic cells," *Virology*, 281:231-238, 2001.
Snow et al., "The global distribution of clinical episodes of *Plasmodium falciparum* malaria," *Nature*, 434:214-217, 2005.
Soderlind et al., "Complementarity-determining region (CDR) implantation: a theme of recombination," *Immunotechnol.*, 4:279, 1999.
Soderlind et al., "Recombining germline-derived CDR sequences for creating diverse single framework antibody libraries," *Nature Biotechnol.*, 18:852, 2000.
Soini et al., "Presence of human papillomavirus DNA and abnormal p53 protein accumulation in lung carcinoma," *Thorax*, 51:887-893, 1996.
Spilliaert et al., "Cloning and sequencing of a *Rhodothermus marinus* gene, bglA, coding for a thermostable beta-glucanase and its expression in *Escherichia coli*," *Eur. J. Biochem.*, 224(3):923-930, 1994.
Stewart et al., "Mutant barley (1→3,1→4)-β-glucan endohydrolases with enhanced thermostability," *Protein Engineering*, 14(4):245-253, 2001.
Thomas et al., "HPV-18 E6 mediated inhibition of p53 DNA binding activity is independent of E6 induced degradation," *Oncogene*, 10:261-8, 1995.
Throsby et al., "Heterosubtypic neutralizing monoclonal antibodies cross-protective against H5NI and H1N1 recovered from human IgM+ memory B cells," *Plos One*, LNKD-PUBMED:19079604, 3(12):E3942, 2008.
Toms et al., "Behaviour in ferrets of swine influenza virus isolated from man," *The Lancet*, pp. 68-71, 1977.
Tsai et al., "Crystal structure of a natural circularly permuted jellyroll protein: 1,3-1,4-beta-D-glucanase from *Fibrobacter succinogens*," *J. Mob. Biol.*, 330(3):607-20, 2003.
UniProt Database [Online] EBI Accession No. Q0PDN1, "SubName: Full=Hemagglutinin," Sep. 5, 2006.
UniProt Database [Online] EBI Accession No. A9X0E7, "SubName: Full=Hemagglutinin; Flags: Precursor," Feb. 5, 2008.
Van der Kolk et al., "Evaluation of the standard membrane feeding assay (SMFA) for the determination of malaria transmission-reducing activity using empirical data," *Parasitol.*, 130(Pt 1):13-22, 2005 (with Erratum in: *Parasitol.*, 131(Pt 4):578, 2005).
Volten-Doting, Plant Viruses Online (http://image.fs.uidaho.edu/vide/deser009.htm) (downloaded May 18, 2002) (11 pgs.).
Wagner et al., "Plant virus expression system for transient production of recombinant allergens in *Nicotiana benthamiana*," *Methods: A Companion to Methods in Enzymology*, 32(3):227-234, 2004.
Wang et al, "Immunogenicity of *Plasmodium yoelii* merozoite surface protein 4/5 produced in transgenic plants," *Int. J. Parasitol.*, 38(1):103-110, 2007.
Wang et al., "Structural basis for thermostability of beta-glycosidase from the thermophilic eubacterium *Thermus nonproteolyticus* HG102," *J. Bacteriol.*, 185:4248-55, 2003.
Webster et al., "Measles virus hemagglutinin protein expressed in transgenic lettuce induces neutralizing antibodies in mice following mucosal vaccination," *Vaccine*, 24(17): 3538-3544, 2006.
Webster et al., "Protection of ferrets against influenza challenge with a DNA vaccine to the haemagglutinin," *Vaccine*, 12(16):1495-1498, 1994.
Webster et al., "Antigenic structure and variation in an influenza virus N9 neuraminidase," *J. Virology*, 61:2910-2916, 1987.
Wiesmuller et al., "Peptide vaccines and peptide libraries," *Biol. Chem.*, 382(4):571-9, 2001.
Williamson et al., "Human immune response to a plague vaccine comprising recombinant F1 and V antigens," *Infect. Immun.*, 73(6):3598-608, 2005.
Williamson et al., "A single dose sub-unit vaccine protects against pneumonic plague," *Vaccine*, 19:566-71, 2000.
Williamson et al., "A new improved sub-unit vaccine for plague: the basis of protection," *FEMS Immunol. Med. Microbiol.*, 12:223-30, 1995.
Wilson et al., "Structure of the haemagglutinin membrane glycoprotein of influenza virus at 3 Å resolution," *Nature*, 289:366, 1981.
Winter and Milstein, "Man-made antibodies," *Nature*, 349:293, 1991.
The World Health Organization Global Influenza Program Surveillance Network, Evolution of H5N1 Avian Influenza Viruses in Asia, *Emerging Infectious Diseases*, 11(10):1515-1521, 2005.
Yang et al., "Production and diagnostic application of monoclonal antibodies against influenza virus H5," *J. Virolog. Methods*, 162(1-2):194-202, 2009.
Yusibov et al., "Functional significance of three basic N-terminal amino acids of alfalfa mosaic virus coat protein," *Virol.*, 242:1-5, 1998.
Yusibov et al., "An influenza N1 neuraminidase-specific monoclonal antibody with broad inactivating activity against H5N1 viruses," *Human Antibodies*, 16(1-2):33, 2007.
Yusibov et al., "An influenza N1 neuraminidase-specific monoclonal antibody protects animal against live challenge with homologous H5N1 virus," *Human Antibodies*, 17(1-2):15, 2008.
Zapata et al., "Engineering linear F(ab')2 fragments for efficient production in *Escherichia coli* and enhanced antiproliferative activity," *Prot. Eng.*, 8:1057, 1995.
Zumbach et al., "Antibodies against oncoproteins E6 and E7 of human papillomavirus types 16 and 18 in patients with head-and-neck squamous-cell carcinoma," *Int. J. Cancer*, 85:815-818, 2000.
Advisory Action dated Jan. 15, 2010 for U.S. Appl. No. 11/706,568 (3 pgs.).
Communication dated Sep. 23, 2009 for European Appln. No. 04776107.7 (3 pgs.).
Communication dated Apr. 21, 2010 for European Appln. No. 04776107.7 (4 pgs.).
Communication dated May 20, 2010 for European Appln. No. 04776107.7 (3 pgs.).
Communication dated Feb. 18, 2010 for EP Appln. No. 07750905.7 (2 pgs.).
International Preliminary Report on Patentability dated Aug. 19, 2008 for Int'l. Appln. No. PCT/US07/003948 (6 pgs.).
International Preliminary Report on Patentability dated Aug. 19, 2008 for Int'l. Appln. No. PCT/US07/003969 (6 pgs.).
International Preliminary Report on Patentability dated Aug. 19, 2008 for Int'l. Appln. No. PCT/US07/003973 (6 pgs.).
International Preliminary Report on Patentability dated Mar. 17, 2009 for Int'l. Appln. No. PCT/US07/004103 (5 pgs.).
International Preliminary Report on Patentability dated Oct. 21, 2008 for Int'l. Appln. No. PCT/US08/061782 (7 pgs.).
International Preliminary Report on Patentability dated Jan. 12, 2010 for Int'l. Appln. No. PCT/US08/069860 (5 pgs.).
International Preliminary Report on Patentability dated Mar. 4, 2010 for Int'l. Appln. No. PCT/US08/073776 (6 pgs.).
International Preliminary Report on Patentability dated Mar. 29, 2011 for Int'l Appln. No. PCT/US09/058640 (7 pgs.).
International Preliminary Report on Patentability dated Mar. 29, 2011 for Int'l. Appln. No. PCT/US09/058669 (12 pgs.).
International Search Report dated Dec. 23, 2005 for Int'l Appln. No. PCT/US04/16452 (2 pgs.).
International Search Report and Written Opinion dated Jun. 18, 2008 for Int'l. Appln. No. PCT/US07/003948 (9 pgs.).
International Search Report and Written Opinion dated Sep. 4, 2007 for Int'l. Appln. No. PCT/US07/003969 (10 pgs.).
International Search Report and Written Opinion dated Aug. 3, 2007 for Int'l. Appln. No. PCT/US07/003973 (9 pgs.).
International Search Report and Written Opinion dated Aug. 7, 2007 for Int'l. Appln. No. PCT/US07/004103 (9 pgs.).
International Search Report and Written Opinion dated Oct. 21, 2008 for Int'l. Appln. No. PCT/US08/061782 (10 pgs.).
International Search Report and Written Opinion dated May 29, 2009 for Int'l Appln. No. PCT/US08/069860 (8 pgs.).

(56) References Cited

OTHER PUBLICATIONS

International Search Report and Written Opinion dated Apr. 24, 2009 for Int'l. Appln. No. PCT/US08/073776 (11 pgs.).
International Search Report and Written Opinion dated May 11, 2010 for Int'l Appln. No. PCT/US09/058488 (20 pgs.).
International Search Report and Written Opinion dated Feb. 2, 2010 for Int'l Appln. No. PCT/US09/058640 (13 pgs.).
International Search Report and Written Opinion dated May 19, 2010 for Int'l Appln. No. PCT/US09/058669 (21 pgs.).
International Search Report and Written Opinion dated Jan. 27, 2011 for Int'l. Appln. No. PCT/US10/050693 (7 pgs.).
Notification of Defects in Patent Application dated Sep. 16, 2010 for Israel Patent Appln. No. 193391 (3 pgs.).
Office Action (non-final) dated Nov. 4, 2008 for U.S. Appl. No. 11/706,568 (7 pgs.).
Office Action (non-final) dated Jan. 6, 2009 for U.S. Appl. No. 11/706,568 (8 pgs.).
Office Action (final) dated Jul. 15, 2009 for U.S. Appl. No. 11/706,568 (7 pgs.).
Supplementary European Search Report dated Dec. 5, 2006 for European Appln. No. 04776107 (2 pgs.).
Supplementary European Search Report dated May 5, 2010 for European Appln. No. 07750784 (8 pgs.).
Supplementary European Search Report dated Oct. 8, 2009 for European Appln. No. 07750950 (5 pgs.).
Baldwin et al., "Vaccinia-expressed human papillomavirus 16 and 18 E6 and E7 as a therapeutic vaccination for vulval and vaginal intraepithelial neoplasia," Clin. Cancer Res., 9(12):5205-5213, 2003.
de Jong et al., "Enhancement of human papillomavirus (HPV) type 16 E6 and E7-specific T-cell immunity in healthy volunteers through vaccination with TA-CIN, an HPV16 L2E7E6 fusion protein vaccine," Vaccine, 20(29-30):3456-3464, 2002.
Marillonnet Sylvestre et al., "Systemic *Agrobacterium tumefaciens*—mediated transfection of viral relicons for efficient transient expression in plant," Nature Biotechnology, 23(6):718-723, 2005.
Mett et al., "A non-glycosylated, plant-produced human monoclonal antibody against anthrax protective antigen protects mice and non-human primates from *B. anthracis* spore challenge," *Human Vaccines*, 7:183-190, 2011.

Noah et al., "Qualification of the hemagglutination inhibition assay in support of pandemic influenza vaccine licensure," Clin. Vaccine Immunol., 16(4):558-566, 2009.
Nuttall et al., "A functional antibody lacking N-linked glycans in efficiently folded, assembled and secreted by tobacco mesophyll protoplasts," Plant Biotechnology Journal, 3:497-504, 2005.
Pfitzner et al., "Isolation and characterization of cDNA clones encoding pathogenesis-related proteins from tobacco mosaic virus infected tobacco plants," Nucleic Acids Research, 15(11):4449-4465, 1987.
Pokorna et al., "Combined immunization with fusion genes of mutated E7 gene of human papillomavirus type 16 did not enhance antitumor effect," The Journal of Gene Medicine, 7(6): 696-707, 2005.
Smahel et al., "Enhancement of immunogenicity of HPV16 E7 oncogene by fusion with *E. coli* β-glucuronidase," The Journal of Gene Medicine, 6(10):1092-1101, 2004.
Sweet et al., "Pathogenicity of Influenza Virus," Microbiological Reviews, pp. 303-330, 1980.
Yusibov et al., "The Potential of Plant Virus Vectors for Vaccine Production," Drugs in R & D 7(4):203-217), 2006.
Yusibov et al., "Novel approaches to the development of vaccines: progress on anthrax". Joint meeting, Sep. 27-30, 2005, Bergen, Norway. Sep. 1, 2005, p. 13. Retrieved from the Internet: URL:http://www.sgm.ac.uk/meetings/pdfabstractsjbergen2005abs.pdf [retrieved on Jun. 13, 2012], 44 pgs.
Communication—Summons to Attend Oral Proceedings dated Jan. 4, 2013 from European Appl. No. 06850507.2 (7 pgs.).
Examiner's First Report dated Aug. 24, 2011 for Australian Appln. No. 2007215082 (3 pgs.).
Office Action (restriction requirement) dated Nov. 28, 2007 for U.S. Appl. No. 11/706,573 (8 pgs.).
Office Action (non-final) dated Apr. 16, 2008 for U.S. Appl. No. 11/706,573 (11 pgs.).
Office Action (non-final) dated Jan. 21, 2009 for U.S. Appl. No. 11/706,573 (10 pgs.).
Office Action (non-final) dated Feb. 22, 2010 for U.S. Appl. No. 11/706,573 (11 pgs.).
Office Action (non-final) dated Nov. 24, 2010 for U.S. Appl. No. 11/706,573 (11 pgs.).
Supplementary European Search Report dated Jun. 19, 2012 for European Appln. No. EP 07 75 0787 (12 pages).
Supplementary European Search Report for European Appln. No. 08826237 dated Jan. 25, 2013 (10 pgs.).

\* cited by examiner

FIGURE 1A

Alignment of alpha tubulin sequences from different *Trypanosoma* species

```
cruzi        MREAICIHIGQAGCQVGNACWELFCLEHGIQPDGAMPSDKTIGVEDDAFNTFFSETGAGK 60
brucei       MREAICIHIGQAGCQVGNACWELFCLEHGIQPDGAMPSDKTIGVEDDAFNTFFSETGAGK 60
danilewskyi  MREAICIHIGQAGCQVGNACWELFCLEHGIQPDGAMPSDKTIGVEDDAFNTFFSETGAGK 60
grayi        MREAICIHIGQAGCQVGNACWELFCLEHGIQPDGAMPSDKTIGAEDDAFNTFFSETGAGK 60
             ****************************************.************** cruzi        HVPRAVFLDLEPTVVDEIRTGTYRQLFHPEQLISGKEDAANNYARGHYTIGKEIVDLCLD 120
brucei       HVPRAVFLDLEPTVVDEVRTGTYRQLFHPEQLISGKEDAANNYARGHYTIGKEIVDLCLD 120
danilewskyi  HVPRAVFLDLEPTVVDEIRTGTYRQLFHPEQLISGKEDAANNYARGHYTIGKEIVDLCLD 120
grayi        HVPRAVFLDLEPTVVDEIRTGTYRQLFHPEQLITGKEDAANNYARGHYTIGKEIVDLCLD 120
             ***************:***********:************************ cruzi        RIRKLADNCTGLQGFLVYHAVGGGTGSGLGALLLERLSVDYGKKSKLGYTVYPSPQVSTA 180
brucei       RIRKLADNCTGLQGFLVYHAVGGGTGSGLGALLLERLSVDYGKKSKLGYTVYPSPQVSTA 180
danilewskyi  RIRKLADNCTGLQGFLVYHAVGGGTGSGLGALLLERLSVDYGKKSKLGYTVYPSPQVSTA 180
grayi        RIRKLADNCTGLQGFLVYHAVGGGTGSGLGALLLERLSVDYGKKSKLGYTVYPSPQVSTA 180
             ************************************************************ cruzi        VVEPYNSVLSTHSLLEHTDVAAMLDNEAIYDLTRRNLDIERPTYTNLNRLIGQVVSALTA 240
brucei       VVEPYNSVLSTHSLLEHTDVAAMLDNEAIYDLTRRNLDIERPTYTNLNRLIGQVVSSLTA 240
danilewskyi  VVEPYNSVLSTHSLLEHTDVAAMLDNEAIYDLTRRNLDIERPTYTNLNRLIAQVVSSLTA 240
grayi        VVEPYNSVLSTHSLLEHTDVAAMLDNEAIYDLTRRNLDIERPTYTNLNRLIAQVVSSLTA 240
             *************************************************.:* cruzi        SLRFDGALNVDLTEFQTNLVPYPRIHFVLTSYAPVISAEKAYHEQLSVSEISNAVFEPAS 300
brucei       SLRFDGALNVDLTEFQTNLVPYPRIHFVLTSYAPVISAEKAYHEQLSVSEISNAVFEPAS 300
danilewskyi  SLRFDGALNVDLTEFQTNLVPYPRIHFVLTSYAPVISAEKAYHEQLSVSEISNAVFEPAS 300
grayi        SLRFDGALNVDLTEFQTNLVPYPRIHFVLTSYAPVISAEKAYHEQLSVSEISNAVFEPAS 300
             ************************************************************ cruzi        MMTKCDPRHGKYMACCLMYRGDVVPKDVNAAVATIKTKRTIQFVDWSPTGFKCGINYQPP 360
brucei       MMTKCDPRHGKYMACCLMYRGDVVPKDVNAAVATIKTKRTIQFVDWSPTGFKCGINYQPP 360
danilewskyi  MMTKCDPRHGKYMACCLMYRGDVVPKDVNAAVATIKTKRTIQFVDWSPTGFKCGINYQPP 360
grayi        MMTKCDPRHGKYMACCLMYRGDVVPXDVNAAVATIKTKRTIQFVDWSPTGFXCGINYQPP 360
             *********************** ****************** ***** cruzi        TVVPGGDLAKVQRAVCMIANSTAIAEVFARIDHKFDLMYSKRAFVHWYVGEGMEEGEFSE 420
brucei       TVVPGGDLAKVQRAVCMIANSTAIAEVFARIDHKFDLMYSKRAFVHWYVGEGMEEGEFSE 420
danilewskyi  TVVPGGDLAKVQRAVCMIANSTAIAEVFARIDHKFDLMYSKRAFVHWYVGEGMEEGEFSE 420
grayi        TVVPGGDLAKVQRAVCMIANSTAIAEVFARIDHKFDLMYSKRAFVHWYVGEGMEEGEFSE 420
             ************************************************************ cruzi        AREDLAALEKDYEEVGAESADMEGEEDVEEY 451
brucei       AREDLAALEKDYEEVGAESADMDGEEDVEEY 451
danilewskyi  AREDLAALEKDYEEVGAESGDLEGEEDVEEY 451
grayi        AREDLAALEKDYEEVGAESADMEGEEDVEEY 451
             *******************.*::********
```

FIGURE 1B

Alignment of beta tubulin sequences from different *Trypanosoma* species

```
brucei        MREIVCVQAGQCGNQIGSKFWEVISDEHGVDPTGTYQGDSDLQLERINVYFDEATGGRYV  60
cruzi         -REIVCVQAGQCGNQIGSKFWEVISDEHGVDPTGTYQGDSDLQLERINVYFDEATGGRYV  59
cyclops       MREIVCIQAGQCGNQIGSKFWEVISDEHGVDPTGTYQGDSDLQLERINVYFDEATGGRYV  60
danilewskyi   MREIVCVQAGQCGNQIGSKFWEVISDEHGVDPTGTYQGDSDLQLERINVYFDEATGGRYV  60
              ***:**************************************************** brucei        PRSVLIDLEPGTMDSVRAGPYGQIFRPDNFIFGQSGAGNNWAKGHYTEGAELIDSVLDVC  120
cruzi         PRAVLIDLEPGTMDSVRAGPYGQIFRPDNFIFGQSGAGNNWAKGHYTEGAELIDSVLDVC  119
cyclops       PRAVLIDLEPGTMDSVRAGPYGQVFRPDNFIFGQSGAGNNWAKGHYTEGAELIDSVLDVC  120
danilewskyi   PRAVLIDLEPGTMDSVRAGPYGQIFRPDNFIFGQSGAGNNWAKGHYTEGAELIDSVLDVC  120
              :****************:********************************** brucei        CKEAESCDCLQGFQICHSLGGGTGSGMGTLLISKLREQYPDRIMMTFSIIPSPKVSDTVV  180
cruzi         RKEAESCDCLQGFQICHSLGGGTGSGMGTLLISKLREEYPDRIMMTFSIIPSPKVSDTVV  179
cyclops       RKEAESCDCLQGFQIAHSLGGGTGSGMGTLLISKLREEYPDRIMMTFSIIPSPKVSDTVV  180
danilewskyi   RKEAESCDCLQGFQIAHSLGGGTGSGMGTLLISKLREEYPDRIMMTFSIIPSPKVSDTVV  180
              ************ ******************:******************** brucei        EPYNTTLSVHQLVENSDESMCIDNEALYDICFRTLKLTTPTFGDLNHLVSAVVSGVTCCL  240
cruzi         EPYNTTLSVHQLVENSDESMCIDNEALYDICFRTLKLTTPTFGDLNHLVSAVVSGVTCCL  239
cyclops       EPYNTTLSVHQLVENSDESMCIDNEALYDICFRTLKLTTPTFGDLNHLVSAVMSGVTCCL  240
danilewskyi   EPYNTTLSVHQLVENSDESMCIDNEALYDICFRTLKLTTPTFGDLNHLVSAVMSGVTCCL  240
              **************************************************:***** brucei        RFPGQLNSDLRKLAVNLVPFPRLHFFMMGFAPLTSRGSQQYRGLSVPELTQQMFDAKNMM  300
cruzi         RFPGQLNSDLRKLAVNLVPFPRLHFFMMGFAPLSSRGSQQYRGLSVPDVTQQMFDAKNMM  299
cyclops       RFPGQLNSDLRKLAVNLVPFPRLHFFMMGFAPLTSRGSQQYRGLSVPELTQQMFDAKNMM  300
danilewskyi   RFPGQLNSDLRKLAVNLVPFPRLHFFMMGFAPLTSRGSQQYRGLSVPELTQQMFDAKNMM  300
              *******************************:*********::********* brucei        QAADPRHGRYLTASALFRGRMSTKEVDEQMLNVQNKNSSYFIEWIPNNIKSSVCDIPPKG  360
cruzi         QAADPAHGRYLTASALFRGRMSTKEVDEQMLNVQNKNSSYFIEWIPNNIKSSICDIPPKG  359
cyclops       QAADPRHGRYLTASALFRGRMSTKEVDEQMLNVLNKNSSYFIEWIPNNIKSSICDIPPKG  360
danilewskyi   QAAEPRHGRYLTASALFRGRMSTKEIDEQMLNVQNKNSSYFIEWIPNNIKSSICDIPPKG  360
              ***:* *****************:*** ******************** brucei        LKMAVTFIGNNTCIQEMFRRVGEQFTLMFRRKAFLHWYTGEGMDEMEFTEAESNMNDLVS  420
cruzi         LKMAVTFVGNNTCIQEMFRRVGEQFTAMFRRKAFLHWYTGEGMDEMEFTEAESNMNDLVS  419
cyclops       LKMAVTFIGNNTCIQEMFRRVGEQFTAMFRRKAFLHWY----------------------  398
danilewskyi   LKMAVTFIGNNTCIQEMFRRVGEQFTAMFRRKAFLHWYTGEGMDEMEFTEAESNMNDLVS  420
              *****:*************:********* brucei        EYQQYQDATIEEEGEFDEEEQY  442
cruzi         EYQQYQDATIEEEGEFDEEEQY  441
cyclops       ----------------------
danilewskyi   EYQQYQDATVEEEGEFDEEEQY  442
```

FIGURE 1C

```
Alpha tubulin ubiquitous cow ("bos")
Alpha tubulin ubiquitous homo ("homo")
Alpha tubulin Trypanosoma ("Tryps")

bos    MRECISIHVGQAGVQIGNACWELYCLEHGIQPDGQMPSDKTIGGGDDSFNTFFSETGAGK    60
homo   MRECISIHVGQAGVQIGNACWELYCLEHGIQPDGQMPSDKTIGGGDDSFNTFFSETGAGK    60
Tryps  MREAICIHIGQAGCQVGNACWELFCLEHGIQPDGAMPSDKTIGVEDDAFNTFFSETGAGK    60
       *.:.:*****.*:*.*:*******.******.*:.************** bos    HVPRAVFVDLEPTVIDEVRTGTYRQLFHPEQLITGKEDAANNYARGHYTIGKEIIDLVLD   120
homo   HVPRAVFVDLEPTVIDEVRTGTYRQLFHPEQLITGKEDAANNYARGHYTIGKEIIDLVLD   120
Tryps  HVPRAVFLDLEPTVVDEVRTGTYRQLFHPEQLISGKEDAANNYARGHYTIGKEIVDLCLD   120
       *****:**:**************:******************::* bos    RIRKLADQCTGLQGFLVFHSFGGGTGSGFTSLLMERLSVDYGKKSKLEFSIYPAPQVSTA   180
homo   RIRKLADQCTGLQGFLVFHSFGGGTGSGFTSLLMERLSVDYGKKSKLEFSIYPAPQVSTA   180
Tryps  RIRKLADNCTGLQGFLVYHAVGGGTGSGLGALLLERLSVDYGKKSKLGYTVYPSPQVSTA   180
       *****:*******:*::*****:.::********. ::::******* bos    VVEPYNSILTTHTTLEHSDCAFMVDNEAIYDICRRNLDIERPTYTNLNRLISQIVSSITA   240
homo   VVEPYNSILTTHTTLEHSDCAFMVDNEAIYDICRRNLDIERPTYTNLNRLISQIVSSITA   240
Tryps  VVEPYNSVLSTHSLLEHTDVAAMLDNEAIYDLTRRNLDIERPTYTNLNRLIGQVVSSLTA   240
       *******:*:**: ***:*.*:*:******: *************:*:*:***:**

bos    SLRFDGALNVDLTEFQTNLVPYPRIHFPLATYAPVISAEKAYHEQLSVAEITNACFEPAN   300
homo   SLRFDGALNVDLTEFQTNLVPYPRIHFPLATYAPVISAEKAYHEQLSVAEITNACFEPAN   300
Tryps  SLRFDGALNVDLTEFQTNLVPYPRIHFVLTSYAPVISAEKAYHEQLSVSEISNAVFEPAS   300
       **************************.*::***************:**:**.****:

bos    QMVKCDPRHGKYMACCLLYRGDVVPKDVNAAIATIKTKRSIQFVDWCPTGFKVGINYQPP   360
homo   QMVKCDPRHGKYMACCLLYRGDVVPKDVNAAIATIKTKRSIQFVDWCPTGFKVGINYQPP   360
Tryps  MMTKCDPRHGKYMACCLMYRGDVVPKDVNAAVATIKTKRTIQFVDWSPTGFKCGINYQPP   360
       :*.************:*********:***:**.*.**** bos    TVVPGGDLAKVQRAVCMLSNTTAIAEAWARLDHKFDLMYAKRAFVHWYVGEGMEEGEFSE   420
homo   TVVPGGDLAKVQRAVCMLSNTTAIAEAWARLDHKFDLMYAKRAFVHWYVGEGMEEGEFSE   420
Tryps  TVVPGGDLAKVQRAVCMIANSTAIAEVFARIDHKFDLMYSKRAFVHWYVGEGMEEGEFSE   420
       *****************::*:***.::******:***************** bos    AREDMAALEKDYEEVGVDSVEGEGEEEGEEY   451
homo   AREDMAALEKDYEEVGVDSVEGEGEEEGEEY   451
Tryps  AREDLAALEKDYEEVGAESADMGEEDVEEY   451
       ****:***********.: .: :***: ***
```

FIGURE 1D

Alignment of beta tubulin proteins in cow, human, and Trypanosoma species

```
Cow          MREIVHIQAGQCGNQIGAKFWEVISDEHGIDPTGSYHGDSDLQLERINVYYNEATGNKYV 60
Human        MREIVHLQAGQCGNQIGAKFWEVISDEHGIDPTGTYHGDSDLQLERINVYYNEATGGKYV 60
Trypanosoma  MREIVCVQAGQCGNQIGSKFWEVISDEHGVDPTGTYQGDSDLQLERINVYFDEATGGRYV 60
             ****  :********** :************.******* *****:********.****..:**

Cow          PRAILVDLEPGTMDSVRSGPFGQIFRPDNFVFGQSGAGNNWAKGHYTEGAELVDSVLDVV 120
Human        PRAVLVDLEPGTMDSVRSGPFGQIFRPDNFVFGQSGAGNNWAKGHYTEGAELVDSVLDVV 120
Trypanosoma  PRSVLIDLEPGTMDSVRAGPYGQIFRPDNFIFGQSGAGNNWAKGHYTEGAELIDSVLDVC 120
             **::*:***********:**:*********:*********************:******

Cow          RKESESCDCLQGFQLTHSLGGGTGSGMGTLLISKIREEYPDRIMNTFSVMPSPKVSDTVV 180
Human        RKEAESCDCLQGFQLTHSLGGGTGSGMGTLLISKIREEYPDRIMNTFSVVPSPKVSDTVV 180
Trypanosoma  CKEAESCDCLQGFQICHSLGGGTGSGMGTLLISKLREQYPDRIMMTFSIIPSPKVSDTVV 180
             ** :***********: ****************:**:******* ***::*:*********

Cow          EPYNATLSVHQLVENTDETYSIDNEALYDICFRTLKLTTPTYGDLNHLVSATMSGVTTCL 240
Human        EPYNATLSVHQLVENTDETYCIDNEALYDICFRTLKLTTPTYGDLNHLVSATMSGVTTCL 240
Trypanosoma  EPYNTTLSVHQLVENSDESMCIDNEALYDICFRTLKLTTPTFGDLNHLVSAVVSGVTCCL 240
             ****.**********.**: *********************:********.*:*** **

Cow          RFPGQLNADLRKLAVNMVPFPRLHFFMPGFAPLTSRGSQQYRALTVPELTQQMFDSKNMM 300
Human        RFPGQLNADLRKLAVNMVPFPRLHFFMPGFAPLTSRGSQQYRALTVPELTQQMFDAKNMM 300
Trypanosoma  RFPGQLNSDLRKLAVNLVPFPRLHFFMMGFAPLTSRGSQQYRGLSVPELTQQMFDAKNMM 300
             *******:********:**********.*************.*.:*********:****

Cow          AACDPRHGRYLTVAAIFRGRMSMKEVDEQMLNVQNKNSSYFVEWIPNNVKTAVCDIPPRG 360
Human        AACDPRHGRYLTVAAVFRGRMSMKEVDEQMLNVQNKNSSYFVEWIPNNVKTAVCDIPPRG 360
Trypanosoma  QAADPRHGRYLTASALFRGRMSTKEVDEQMLNVQNKNSSYFIEWIPNNIKSSVCDIPPKG 360
             *.***********::*******:*****************:******:*:.******:*

Cow          LKMSATFIGNSTAIQELFKRISEQFTAMFRRKAFLHWYTGEGMDEMEFTEAESNMNDLVS 420
Human        LKMSATFIGNSTAIQELFKRISEQFTAMFRRKAFLHWYTGEGMDEMEFTEAESNMNDLVS 420
Trypanosoma  LKMAVTFIGNNTCIQEMFRRVGEQFTLMFRRKAFLHWYTGEGMDEMEFTEAESNMNDLVS 420
             ***:.*****.*.***:*:*:.****  ********************************

Cow          EYQQYQDATADEQGEFEEEEGEDEA 445
Human        EYQQYQDATAEEEGEFEEEAEEEVA 445
Trypanosoma  EYQQYQDATIEEEGEFDEEEQY--- 442
             *********  :*:***:**
```

Figure 4

AIMV CP with β tubulin peptide
AIMV CP

AIMV CP with β tubulin peptide
AIMV CP Standard

UD  UC  1/40  1/100
     dilutions

*Significant P<0.05

*Significant P<0.05

Figure 7B

TRYPANOSOMA ANTIGENS, VACCINE COMPOSITIONS, AND RELATED METHODS

CROSS-REFERENCE TO RELATED APPLICATIONS

This application claims priority under 35 U.S.C. §119(e) to U.S. provisional patent applications, U.S. Ser. No. 60/914,734, filed Apr. 28, 2008 2007 ("the '734 application") and U.S. Ser. No. 60/984,945, filed Nov. 2, 2007 ("the '945 application"). The entire contents of each of the '734 application and the '945 application are incorporated herein by reference.

BACKGROUND OF THE INVENTION

African trypanosomiasis, also known as "sleeping sickness" in humans and "nagana" in animals, is a serious parasitic disease that if left untreated is almost always fatal. The disease, spread by the bite of tsetse flies, occurs in 36 countries of sub-Saharan Africa and is reaching epidemic proportions. According to the World Health Organization (WHO), there are an estimated 40,000 newly infected people each year with mortality rates reaching more than 66,000 and increasing. The social and economic impact of this disease is even more devastating because it is equally fatal to humans and animals. In Africa, the wide occurrence of trypanosomiasis in both humans and livestock is a great constraint to development, particularly in rural areas. The situation is worsened by the direct impact of nagana on agriculture and food supply in sub-Saharan Africa. Millions of hectares of land cannot be economically exploited because of human and animal African trypanosomiasis. High mortality in cattle has a significant impact on milk and meat production. For example, tsetse-free-areas produce 83% more milk and 97% more meat per unit of land than tsetse-infested areas. The economic losses in cattle production alone are in the range of US$1.2 billion with total agricultural Gross Domestic Product losses approaching an estimated US$5 billion per annum. In an area that is already suffering from poor economy and almost non-existing medical infrastructure, the burden of this disease becomes even more devastating with significant local and regional impact. Currently there is no vaccine available to prevent this disease.

Thus, there is a need to provide sources of vaccines and antigens for production of vaccines. Improved vaccine design and development, as well as methods of making and using such compositions of matter are needed which provide inexpensive and highly accessible sources of such therapeutic and/or prophylactic compositions.

SUMMARY OF THE INVENTION

The present invention provides *Trypanosoma* (e.g. *T. brucei*) antigens and vaccine components produced in plants. The present invention provides one or more *Trypanosoma* antigens generated as a fusion with Alfalfa mosaic virus coat protein (AlMV CP). The present invention provides one or more *Trypanosoma* antigens generated as a fusion with a thermostable protein (e.g. lichenase). The invention provides vaccine compositions containing *Trypanosoma* antigens. Furthermore, the invention provides *T. brucei* vaccines comprising at least two different *Trypanosoma* antigens. In some embodiments, inventive compositions include one or more plant components. Still further provided are methods for production and use of the antigen and vaccine compositions of the invention.

BRIEF DESCRIPTION OF THE DRAWING

FIG. 1. Alignment of Alpha and Beta Tubulin Proteins. FIGS. 1A and 1B show CLUSTAL W (1.82) multiple sequence alignments of alpha tubulin (A) and beta tubulin (B) proteins in four different *Trypanosoma* species. FIG. 1A shows sequence alignments of alpha tubulin in *T. cruzi* (SEQ ID NO: 35), *T. brucei* (SEQ ID NO: 1), *T. danilewskyi* (SEQ ID NO: 36) and *T. grayi* (SEQ ID NO: 37). FIG. 1B shows sequence alignments of beta tubulin in *T. cruzi* (SEQ ID NO: 38), *T. brucei* (SEQ ID NO: 2), *T. danilewskyi* (SEQ ID NO: 40), and *T. grayi* (SEQ ID NO: 39). FIGS. 1A and 1B show CLUSTAL W (1.82) multiple sequence alignments of alpha tubulin and beta tubulin proteins in cow, human and *Trypanosoma*. FIG. 1C shows sequence alignments of alpha tubulin in cow (SEQ ID NO. 33), human (SEQ ID NO. 34) and *Trypanosoma* (SEQ ID NO: 1). FIG. 1D shows sequence alignments of beta tubulin in cow (SEQ ID NO. 41), human (SEQ ID NO. 42) and *Trypanosoma* (SEQ ID NO: 2). Sequences of tubulin peptides shown in Tables 1 and 2 are bold and underlined.

FIG. 4. Analysis of purified recombinant virus particles by Western blot. To monitor recombinant virus particle purification during downstream processing, samples were taken from the supernatant after removal of plant debris and from the supernatant after ultra-centrifugation and compared to the final purified sample. Samples were prepared in 5×SDS loading buffer, boiled for 8 minutes, and centrifuged at 13,000 rpm before loading of 10 μl onto a 10% SDS PAGE gel. After separation of virus protein, recombinant virus protein was visualized directly through coomassie staining. For Western blot analysis, the gels were blotted to nitrocellulose membranes. Membranes were processed using polyclonal antisera against the AlMV coat protein as primary antibody and Alkaline-phosphatase-labeled antibody as secondary antibody. UD: undiluted virus preparation. UC: ultracentrifugation supernatant.

Figure 2:
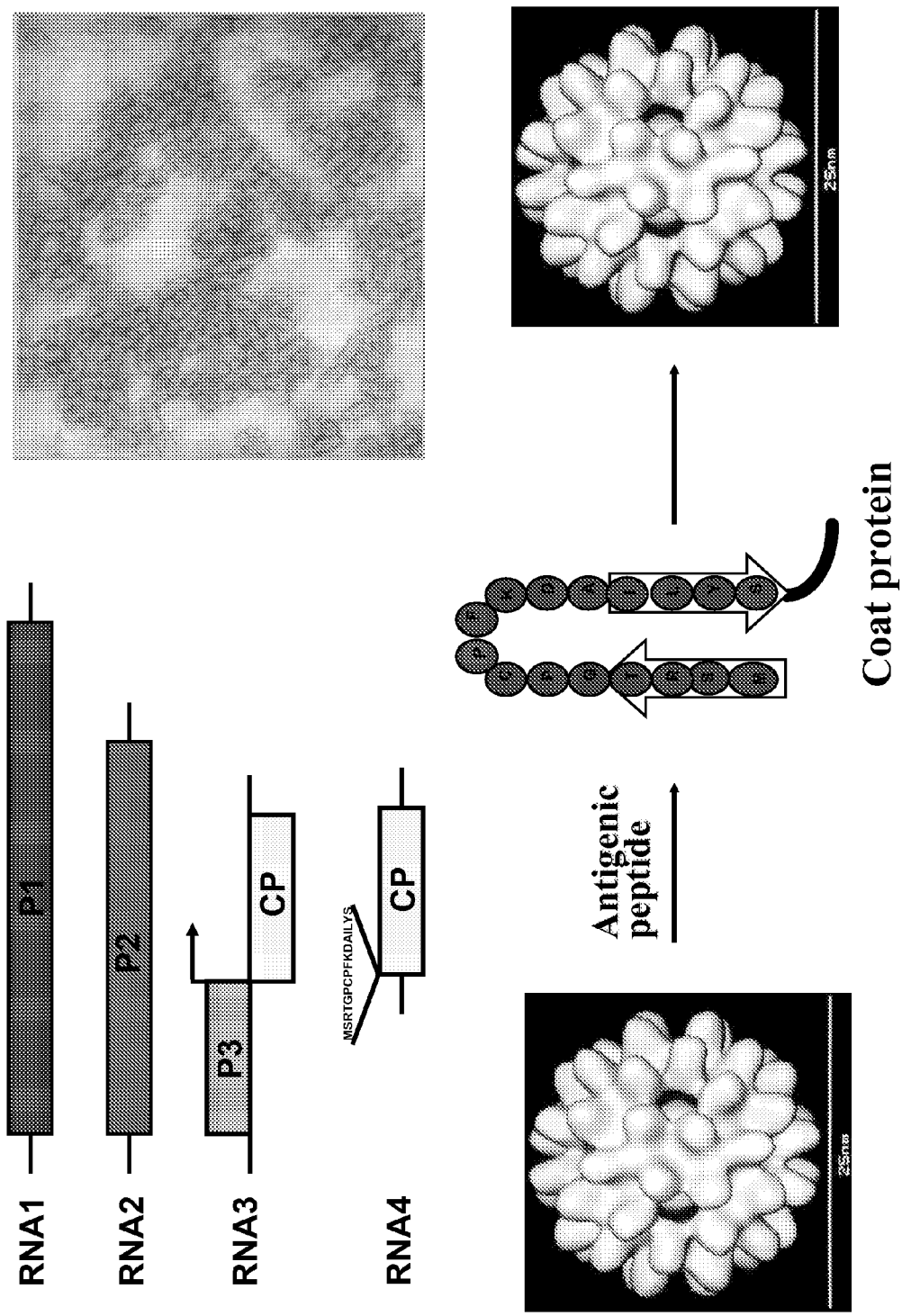
FIG. 2. Strategies for candidate vaccine development: AlMV particle-based approach. α- and β-tubulin amino acid sequences of *Trypanosoma* brucei were aligned with those of *Homo sapiens* (human) and *Bos taurus* (cow). α- and β-tubulin sequences that had low homology with those of *H. sapiens* and *B. taurus* were chosen as target peptides. The *T. brucei* microtubule-associated protein p15 (MAP15) amino acid sequence consists of sixteen nearly identical tandem repeats of five amino acids with a periodicity of five amino acids. Thus, five target peptides were selected from within the MAP15 sequences that comprise the main structural elements of this protein. DNA sequences of target peptides were synthesized and cloned as in-frame N-terminal fusions with Alfalfa mosaic virus coat protein (AlMV CP), which is expressed by the AlMV-based RNA3 vector. The AlMV-based RNA 3 vector requires the replicase proteins P1 and P2 for replication of RNA3. Recombinant AlMV CP is expressed from RNA3 via subgenomic messenger RNA4. During multiplication of the AlMV system in tobacco plants, the recombinant AlMV CP assembles into virions that display multiple copies of the target peptide on their surfaces.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, and/or 3' end formation); (3) translation of an RNA into a polypeptide or protein; (4) post-translational modification of a polypeptide or protein.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product: As used herein, the term "gene product" or "expression product" generally refers to an RNA transcribed from the gene (pre- and/or post-processing) or a polypeptide (pre- and/or post-modification) encoded by an RNA transcribed from the gene.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g. between nucleic acid molecules (e.g. DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95% or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using a NWSgapdna.CMP matrix.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, at least 4, at least 5, at least 6, at least 7, at least 8, at least 9, at least 10, or more residues. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention may be specifically directed to "unmodified nucleic acids," meaning nucleic acids (e.g. polynucleotides and residues, including nucleotides and/or nucleosides) that have not been chemically modified in order to facilitate or achieve delivery.

Operably linked: As used herein, the term "operably linked" refers to a relationship between two nucleic acid sequences wherein the expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. A nucleic acid sequence that is operably linked to a second nucleic acid sequence may be covalently linked, either directly or indirectly, to such a sequence, although any effective three-dimensional association is acceptable.

Portion: As used herein, the phrase a "portion" or "fragment" of a substance, in the broadest sense, is one that shares some degree of sequence and/or structural identity and/or at least one functional characteristic with the relevant intact substance. For example, a "portion" of a protein or polypeptide is one that contains a continuous stretch of amino acids, or a collection of continuous stretches of amino acids, that together are characteristic of a protein or polypeptide. In some embodiments, each such continuous stretch generally will contain at least 2, 5, 10, 15, 20 or more amino acids. In general, a portion is one that, in addition to the sequence identity specified above, shares at least one functional characteristic with the relevant intact protein. In some embodiments, the portion may be biologically active.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, etc. In some embodiments, proteins may comprise natural amino acids, non-natural amino acids, synthetic amino acids, and combinations thereof. The term "peptide" is generally used to refer to a polypeptide having a length of less than about 100 amino acids.

Similarity: As used herein, the term "similarity" refers to the overall relatedness between polymeric molecules, e.g. between nucleic acid molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Subject: As used herein, the term "subject" or "patient" refers to any organism to which compositions in accordance with the invention may be administered, e.g., for experimental, diagnostic, prophylactic, and/or therapeutic purposes. Typical subjects include animals (e.g., mammals such as mice, rats, rabbits, non-human primates, and humans; insects; worms; etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition.

Therapeutic agent: As used herein, the phrase "therapeutic agent" refers to any agent that, when administered to a subject, has a therapeutic effect and/or elicits a desired biological and/or pharmacological effect.

Treatment: As used herein, the term "treatment" (also "treat" or "treating") refers to any administration of a biologically active agent that partially or completely alleviates, ameliorates, relives, inhibits, delays onset of, prevents, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Vector: As used herein, "vector" refers to a nucleic acid molecule which can transport another nucleic acid to which it has been linked. In some embodiment, vectors can achieve extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DETAILED DESCRIPTION OF THE INVENTION

The invention relates to *Trypanosoma* (e.g. *T. brucei*) antigens useful in the preparation of vaccines against *Trypanosoma* infection, and fusion proteins comprising such *Trypanosoma* antigens operably linked to alfalfa mosaic virus (AlMV) coat protein (CP) and/or a thermostable protein (e.g. lichenase). The invention relates to methods of production of provided antigens, including but not limited to, production in plant systems. Further, the invention relates to vectors, fusion proteins, plant cells, plants and vaccine compositions comprising the antigens and fusion proteins of the invention. Still further provided are methods of inducing immune response against *Trypanosoma* infection in a subject comprising administering vaccine compositions of the invention to a subject.

*Trypanosoma brucei* Antigens

*Trypanosoma* are intravascular, extracellular protozoan parasites which are transmitted by tsetse flies of the genus *Glossina*. The main pathogenic *Trypanosoma* species in animals are *T. congolense, T. vivax, T simiae*, and *T. brucei*. There are three major subtypes of *T. brucei. T. b. brucei*, which causes nagana in animals, is morphologically indistinguishable from the human parasites *T. brucei gambiense* and *T. brucei rhodesiense* which, respectively, cause the chronic Gambian and the acute Rhodesian types of sleeping sickness. To give but a few examples, other *Trypanosoma* species include *T. avium*, which causes trypanosomiasis in birds; *T. boissoni*, which causes disease in elasmobranch (cartilaginous fish); *T. carassii*, which causes disease in freshwater teleosts (ray-finned fish); *T. cruzi*, which causes Chagas disease in humans; *T. congolense*, which causes Nagana in cattle, horses, and camels; *T. equinum*, which causes disease in horses; *T. equiperdum*, which causes dourine or covering sickness in horses and other Equidae; *T. evansi*, which causes one form of the disease surra in certain animals, including humans; *T. levisi*, which causes disease in rats; *T. melophagium*, which causes disease in sheep; *T. percae* which causes disease in fish; *T. rotatorium*, which causes disease in amphibians; *T. simiae*, which causes nagana; *T. suis*, which causes one form of surra; *T. theileri*, which causes disease in ruminants; *T. triglae*, which causes disease in teleosts; and *T. vivax*, which causes nagana.

*Trypanosoma* (e.g. *T. brucei*) antigen proteins of the present invention include any immunogenic protein or peptide capable of eliciting an immune response against *Trypanosoma* protozoa. Generally, immunogenic proteins of interest include *Trypanosoma* antigens (e.g., *Trypanosoma* proteins, fusion proteins, etc.), immunogenic portions thereof, or immunogenic variants thereof and combinations of any of the foregoing.

Any *Trypanosoma* protein can be produced and utilized as an antigen in accordance with the present invention. Typically, *Trypanosoma* proteins (i.e. full-length proteins, portions, fragments, and/or domains thereof, peptides, etc.) that are useful as antigens are not substantially identical and/or homologous to proteins which are expressed by the animal being vaccinated. In some embodiments, *Trypanosoma* proteins are less than 90%, less than 80%, less than 70%, less than 60%, less than 50%, less than 40%, less than 30%, less than 20%, or less than 10% identical and/or homologous to proteins which are expressed by the animal being vaccinated. In some embodiments, a particular *Trypanosoma* protein may have portions and/or domains that are substantially identical and/or homologous to proteins which are expressed by the animal being vaccinated as well as portions and/or domains that are not substantially identical and/or homologous to proteins which are expressed by the animal being vaccinated. In some embodiments, proteins and/or peptides to be used in accordance with the present invention are protein portions and/or domains that are not substantially identical and/or homologous to proteins which are expressed by the animal being vaccinated that have been separated and/or isolated from protein portions and/or domains that are substantially identical and/or homologous to proteins which are expressed by the animal being vaccinated.

*Trypanosoma* (e.g. *T. brucei*) antigens for use in accordance with the present invention may include full-length *Trypanosoma* proteins or portions (i.e. fragments, domains, etc.) of *Trypanosoma* proteins, and/or fusion proteins comprising full-length *Trypanosoma* proteins or portions of *Trypanosoma* proteins. Where portions of *Trypanosoma* proteins are utilized, whether alone or in fusion proteins, such portions retain immunological activity (e.g., cross-reactivity with anti-*Trypanosoma* antibodies). Based on their capacity to induce immunoprotective response against protozoal infection, alpha tubulin and beta tubulin are antigens of interest in generating vaccines. The properties of tubulins of lower eukaryotes (including protozoa, such as *Trypanosoma* species) differ from those of mammals, making it possible to selectively target the lower eukaryotic tubulin for vaccine development. Additional antigens, such as the microtubule-associated proteins p15 (MAP15) and p52 (MAP52) may be useful in production of vaccines (e.g., combination vaccines) in order to improve efficacy of immunoprotection.

Thus, the invention provides plant cells and/or plants expressing a heterologous protein, such as a *Trypanosoma* antigen (e.g., *Trypanosoma* protein or a fragment thereof, a fusion protein comprising a *Trypanosoma* protein or portion thereof). A heterologous protein of the invention can comprise any *Trypanosoma* antigen of interest, including, but not limited to alpha tubulin, beta tubulin, MAP15, and MAP52, or fusion proteins, portions, or combinations of alpha tubulin, beta tubulin, MAP15, and MAP52, a portion of alpha tubulin, a portion of beta tubulin, a portion of MAP15 and/or a portion of MAP52. In some embodiments, the invention provides plant cells and/or plants expressing a full-length heterologous protein. In some embodiments, the invention provides plant cells and/or plants expressing a portion of a heterologous protein. In some embodiments, the invention provides plant cells and/or plants expressing multiple portions of a heterologous protein. In some embodiments, such multiple portions are each produced from an individual vector. In some embodiments, such multiple protein portions are tandemly expressed from the same vector (i.e. a "polytope"). In some embodiments, all of the multiple protein portions of a polytope are identical to one another. In some embodiments, not all of the multiple protein portions are identical to one another.

Amino acid sequences of a variety of different *Trypanosoma* proteins from *T. brucei* proteins (e.g., alpha tubulin, beta tubulin, MAP15, and MAP52) are known in the art and are available in public databases such as GenBank. Exemplary full length protein sequences for alpha tubulin, beta tubulin, and MAP15 are provided below:

```
T. brucei alpha tubulin, full-length
(SEQ ID NO.: 1):
MREAICIHIGQAGCQVGNACWELFCLEHGIQPDGAMPSDKTIGVEDDAFN

TFFSETGAGKHVPRAVFLDLEPTVVDEVRTGTYRQLFHPEQLISGKEDAA

NNYARGHYTIGKEIVDLCLDRIRKLADNCTGLQGFLVYHAVGGGTGSGLG

ALLLERLSVDYGKKSKLGYTVYPSPQVSTAVVEPYNSVLSTHSLLEHTDV

AAMLDNEAIYDLTRRNLDIERPTYTNLNRLIGQVVSSLTASLRFDGALNV

DLTEFQTNLVPYPRIHFVLTSYAPVISAEKAYHEQLSVSEISNAVFEPAS

MMTKCDPRHGKYMACCLMYRGDVVPKDVNAAVATIKTKRTIQFVDWSPTG

FKCGINYQPPTVVPGGDLAKVQRAVCMIANSTAIAEVFARIDHKFDLMYS

KRAFVHWYVGEGMEEGEFSEAREDLAALEKDYEEVGAESADMDGEEDVEE

Y

T. brucei beta tubulin, full-length
(SEQ ID NO.: 2):
MREIVCVQAGQCGNQIGSKFWEVISDEHGVDPTGTYQGDSDLQLERINVY

FDEATGGRYVPRSVLIDLEPGTMDSVRAGPYGQIFRPDNFIFGQSGAGNN

WAKGHYTEGAELIDSVLDVCCKEAESCDCLQGFQICHSLGGGTGSGMGTL

LISKLREQYPDRIMMTFSIIPSPKVSDTVVEPYNTTLSVHQLVENSDESM

CIDNEALYDICFRTLKLTTPTFGDLNHLVSAVVSGVTCCLRFPGQLNSDL

RKLAVNLVPFPRLHFFMMGFAPLTSRGSQQYRGLSVPELTQQMFDAKNMM

QAADPRHGRYLTASALFRGRMSTKEVDEQMLNVQNKNSSYFIEWIPNNIK

SSVCDIPPKGLKMAVTFIGNNTCIQEMFRRVGEQFTLMFRRKAFLHWYTG

EGMDEMEFTEAESNMNDLVSEYQQYQDATIEEEGEFDEEEQY

T. brucei microtubule associated protein p15
(MAP15), full-length (SEQ ID NO.: 3):
ARATAVPKKAVAKKAAPKKTVAKKAAPKKAVAKKVAPKKAVAKKVVAKK

AVAKKVVAKKVAPKKVVAKKVAPKKVAGKKAAAKKA
```

Alternatively or additionally, FIG. 1 presents several alignments of alpha- and beta-tubulin proteins from different *Trypanosoma* species and from cow, human, and *Trypanosoma*. Sequences of tubulin peptides shown in Tables 1 and 2 are bold and underlined.

The following paragraphs present several non-limiting examples of *Trypanosoma* proteins, portions and/or domains thereof, peptides, etc. that could be used in accordance with the present invention. DNA sequences of 24 target peptides presented below, selected from alpha tubulin, beta tubulin and MAP15, were synthesized and cloned as in-frame N-terminal fusions with Alfalfa mosaic virus coat protein (AlMV CP; see Example 1). Separately, target peptides were engineered in tandem (i.e. "polytopes") and cloned into the loop region of *Clostridium thermocellum* lichenase (LicKM; see Example 1).

Alpha Tubulin

In certain embodiments, full length alpha tubulin is utilized in vaccine compositions of the invention. In some embodiments one or more portions and/or domains of alpha tubulin is used. In certain embodiments, two or three or more portions and/or domains are utilized, as one or more separate polypeptides or linked together in one or more fusion polypeptides. A few exemplary portions of alpha tubulin that can be used in accordance with the present invention are presented in Table 1:

TABLE 1

Exemplary Portions of T. brucei Alpha Tubulin

| Construct | Amino Acid Sequence | Position of Peptide |
|---|---|---|
| 1-10 (18 aa) | REAICIHIGQAGCQVGNA (SEQ ID NO. 4) | 2-19 |
| 2-13 (14 aa) | TGSGLGALLLERLS (SEQ ID NO. 5) | 145-158 |
| 3-17 (24 aa) | YNSVLSTHSLLEHTDVAAMLDNEA (SEQ ID NO. 6) | 185-208 |
| 4-11 (15aa) | NRLIGQVVSSLTASL (SEQ ID NO. 7) | 228-242 |
| 5-18 (14aa) | IHFVLTSYAPVISA (SEQ ID NO. 8) | 265-278 |
| 6-19 (21 aa) | LSVSEISNAVFEPASMMTKCD (SEQ ID NO. 9) | 286-306 |
| 7-29 (18aa) | DVNAAVATIKTKRTIQFV (SEQ ID NO. 10) | 327-344 |
| 8-21 (20aa) | VCMIANSTAIAEVFARIDHK (SEQ ID NO. 11) | 375-394 |

Beta Tubulin

In certain embodiments, full length beta tubulin is utilized in vaccine compositions of the invention. In some embodiments one or more portions and/or domains of beta tubulin is used. In certain embodiments, two or three or more portions and/or domains are utilized, as one or more separate polypeptides or linked together in one or more fusion polypeptides. A few exemplary portions of alpha tubulin that can be used in accordance with the present invention are presented in Table 2:

TABLE 2

Exemplary Portions of T. brucei Beta Tubulin

| Construct | Amino Acid Sequence | Position of Peptide |
|---|---|---|
| 1-1 (18aa) | DEHGVDPTGTYQGDSDLQ (SEQ ID NO. 12) | 26-43 |
| 2-4 (9aa) | PRSVLIDLE (SEQ ID NO. 13) | 61-69 |
| 3-24 (13 aa) | SVRAGPYGQIFRP (SEQ ID NO. 14) | 75-89 |
| 4-12 (23aa) | LLISKLREQYPDRIMMTFSIIPS (SEQ ID NO. 15) | 150-172 |
| 5-14 (14 aa) | HQLVENSDESMCID (SEQ ID NO. 16) | 190-203 |
| 6-18 (12aa) | VSAVVSGVTCCL (SEQ ID NO. 17) | 229-240 |
| 7-19 (11aa) | QYRGLSVPELT (SEQ ID NO. 18) | 280-290 |
| 8-22 (17aa) | SYFIEWIPNNIKSSVCD (SEQ ID NO. 19) | 339-355 |
| 9-25 (12aa) | PPKGLKMAVTFI (SEQ ID NO. 20) | 357-368 |
| 10-28 (20aa) | NTCIQEMFRRVGEQFTLMFR (SEQ ID NO. 21) | 371-390 |

TABLE 2-continued

Exemplary Portions of *T. brucei* Beta Tubulin

| Construct | Amino Acid Sequence | Position of Peptide |
|---|---|---|
| 11-31 (15aa) | DATIEEEGEFDEEEQ (SEQ ID NO. 22) | 427-441 |

MAP15

In certain embodiments, full length MAP15 is utilized in vaccine compositions of the invention. In some embodiments one or more portions and/or domains of MAP15 is used. In certain embodiments, two or three or more portions and/or domains are utilized, as one or more separate polypeptides or linked together in one or more fusion polypeptides. A few exemplary portions of alpha tubulin that can be used in accordance with the present invention are presented in Table 3:

TABLE 3

Exemplary Portions of *T. brucei* MAP15

| Construct | Amino Acid Sequence | Position of Peptide |
|---|---|---|
| 1c-26 (25 aa) | ARATAVPKKAVAKKAAPKKTVAKKA (SEQ ID NO. 23) | 1-25 |
| 2c-30 (31 aa) | ARATAVPKKAVAKKAAPKKTVAKKAAPKKAV (SEQ ID NO. 24) | 1-31 |
| 3c-4 (24 aa) | AKKVAPKKAVAKKVVAKKAVAKKV (SEQ ID NO. 25) | 32-55 |
| 4c-34 (30 aa) | VAKKVAPKKVVAKKVAPKKVAGKKAAAKKA (SEQ ID NO. 26) | 56-85 |
| 5c-37 (26 aa) | VAPKKVVAKKVAPKKVAGKKAAAKKA (SEQ ID NO. 27) | 60-85 |

As exemplary antigens, we have utilized sequences from *T. brucei* alpha tubulin, beta tubulin, and/or MAP15 as described in detail herein. However, it will be understood by one skilled in the art that the methods and compositions provided herein may be adapted to utilize any *Trypanosoma* sequences. It will also be understood by one skilled in the art that the methods and compositions provided herein may be adapted to utilize sequences of any *Trypanosoma* species and/or subtype. Such variation is contemplated and encompassed within the methods and compositions provided herein.

Production of *Trypanosoma* Antigens

In accordance with the present invention, *Trypanosoma* (e.g. *T. brucei*) antigens (including *Trypanosoma* protein(s), portions, fragments, domains, variants, and/or fusions thereof) may be produced in any desirable system; production is not limited to plant systems. Vector constructs and expression systems are well known in the art and may be adapted to incorporate use of *Trypanosoma* antigens provided herein. For example, *Trypanosoma* antigens (including *Trypanosoma* protein(s), portions, fragments, domains, variants, and/ or fusions thereof) can be produced in known expression systems, including mammalian cell systems, transgenic animals, microbial expression systems, insect cell systems, and plant systems, including transgenic and transient plant systems. Particularly where *Trypanosoma* antigens are produced as fusion proteins, it may be desirable to produce such fusion proteins in non-plant systems.

In some embodiments of the invention, *Trypanosoma* antigens are desirably produced in plant systems. Plants are relatively easy to manipulate genetically, and have several advantages over alternative sources such as human fluids, animal cell lines, recombinant microorganisms and transgenic animals. Plants have sophisticated post-translational modification machinery for proteins that is similar to that of mammals (although it should be noted that there are some differences in glycosylation patterns between plants and mammals). This enables production of bioactive reagents in plant tissues. Also, plants can economically produce very large amounts of biomass without requiring sophisticated facilities. Thus, protein production in plants typically requires a much lower capital investment and cost-of-goods than does protein production using other systems. Moreover, plants are not subject to contamination with animal pathogens. Like liposomes and microcapsules, plant cells are expected to provide protection for passage of antigen to the gastrointestinal tract. In many instances, production of proteins in plants leads to improved consumer safety.

Plants may be utilized for production of heterologous proteins via use of various production systems. One such system includes use of transgenic/genetically-modified plants where a gene encoding target product is permanently incorporated into the genome of the plant. Transgenic systems may generate crop production systems. A variety of foreign proteins, including many of mammalian origin and many vaccine candidate antigens, have been expressed in transgenic plants and shown to have functional activity (Tacket et al., 2000, *J. Infect. Dis.*, 182:302; and Thanavala et al., 2005, *Proc. Natl. Acad. Sci., USA,* 102:3378). Additionally, administration of unprocessed transgenic plants expressing hepatitis B major surface antigen to non-immunized human volunteers resulted in production of immune response (Kapusta et al., 1999, *FASEB J.,* 13:1796).

One system for expressing polypeptides in plants utilizes plant viral vectors engineered to express foreign sequences (e.g., transient expression). This approach allows for use of healthy non-transgenic plants as rapid production systems. Thus, genetically engineered plants and plants infected with recombinant plant viruses can serve as "green factories" to rapidly generate and produce specific proteins of interest. Plant viruses have certain advantages that make them attractive as expression vectors for foreign protein production. Several members of plant RNA viruses have been well characterized, and infectious cDNA clones are available to facilitate genetic manipulation. Once infectious viral genetic material enters a susceptible host cell, it replicates to high levels and spreads rapidly throughout the entire plant. There are several approaches to producing target polypeptides using plant viral expression vectors, including incorporation of target polypeptides into viral genomes. One approach involves engineering coat proteins of viruses that infect bacteria, animals or plants to function as carrier molecules for antigenic peptides. Such carrier proteins have the potential to assemble and form recombinant virus-like particles displaying desired antigenic epitopes on their surface. This approach allows for time-efficient production of vaccine candidates, since the particulate nature of a vaccine candidate facilitates easy and cost-effective recovery from plant tissue. Additional advantages include enhanced target-specific immunogenicity, the potential to incorporate multiple vaccine determinants, and ease of formulation into vaccines that can be delivered nasally, orally or parenterally. As an example, spinach leaves containing recombinant plant viral particles carrying epitopes of virus fused to coat protein have generated immune response upon administration (Modelska et al., 1998, *Proc. Natl. Acad. Sci., USA,* 95:2481; and Yusibov et al., 2002, *Vaccine,* 19/20:3155).

Plant Expression Systems

Any plant susceptible to incorporation and/or maintenance of heterologous nucleic acid and capable of producing heterologous protein may be utilized in accordance with the present invention. In general, it will often be desirable to utilize plants that are amenable to growth under defined conditions, for example in a greenhouse and/or in aqueous systems. It may be desirable to select plants that are not typically consumed by human beings or domesticated animals and/or are not typically part of the human food chain, so that they may be grown outside without concern that expressed polynucleotide may be undesirably ingested. In some embodiments, however, it will be desirable to employ edible plants. In particular embodiments, it will be desirable to utilize plants that accumulate expressed polypeptides in edible portions of a plant.

Often, certain desirable plant characteristics will be determined by the particular polynucleotide to be expressed. To give but a few examples, when a polynucleotide encodes a protein to be produced in high yield (as will often be the case, for example, when antigen proteins are to be expressed), it will often be desirable to select plants with relatively high biomass (e.g., tobacco, which has additional advantages that it is highly susceptible to viral infection, has a short growth period, and is not in the human food chain). Where a polynucleotide encodes antigen protein whose full activity requires (or is inhibited by) a particular post-translational modification, the ability (or inability) of certain plant species to accomplish relevant modification (e.g., a particular glycosylation) may direct selection. For example, plants are capable of accomplishing certain post-translational modifications (e.g., glycosylation), however, plants will not generate sialation patterns which is found in mammalian post-translational modification. Thus, plant production of antigen may result in production of a different entity than the identical protein sequence produced in alternative systems.

In certain embodiments of the invention, crop plants, or crop-related plants are utilized. In certain specific embodiments, edible plants are utilized.

Plants for use in accordance with the present invention include Angiosperms, Bryophytes (e.g., Hepaticae, Musci, etc.), Pteridophytes (e.g., ferns, horsetails, lycopods), Gymnosperms (e.g., conifers, cycase, Ginko, Gnetales), and Algae (e.g., Chlorophyceae, Phaeophyceae, Rhodophyceae, Myxophyceae, Xanthophyceae, and Euglenophyceae). Exemplary plants are members of the family Leguminosae (Fabaceae; e.g., pea, alfalfa, soybean); Gramineae (Poaceae; e.g., corn, wheat, rice); Solanaceae, particularly of the genus *Lycopersicon* (e.g., tomato), *Solanum* (e.g., potato, eggplant), *Capsium* (e.g., pepper), or *Nicotiana* (e.g., tobacco); Umbelliferae, particularly of the genus *Daucus* (e.g., carrot), *Apium* (e.g., celery), or *Rutaceae* (e.g., oranges); Compositae, particularly of the genus *Lactuca* (e.g., lettuce); Brassicaceae (Cruciferae), particularly of the genus *Brassica* or *Sinapis*. In certain aspects, plants of the invention may be plants of the *Brassica* or *Arabidopsis* genus. Some exemplary Brassicaceae family members include *Brassica campestris, B. carinata, B. juncea, B. napus, B. nigra, B. oleraceae, B. tournifortii, Sinapis alba,* and *Raphanus sativus*. Some suitable plants that are amendable to transformation and are edible as sprouted seedlings include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower, peas, etc.

Introducing Vectors Into Plants

In general, vectors may be delivered to plants according to known techniques. For example, vectors themselves may be directly applied to plants (e.g., via abrasive inoculations, mechanized spray inoculations, vacuum infiltration, particle bombardment, or electroporation). Alternatively or additionally, virions may be prepared (e.g., from already infected plants), and may be applied to other plants according to known techniques.

A wide variety of viruses are known that infect various plant species, and can be employed for polynucleotide expression according to the present invention (see, for example, in *The Classification and Nomenclature of Viruses,* "Sixth Report of the International Committee on Taxonomy of Viruses" (Ed. Murphy et al.), Springer Verlag: New York, 1995, the entire contents of which are incorporated herein by reference; Grierson et al., *Plant Molecular Biology,* Blackie, London, pp. 126-146, 1984; Gluzman et al., *Communications in Molecular Biology: Viral Vectors,* Cold Spring Harbor Laboratory, Cold Spring Harbor, N.Y., pp. 172-189, 1988; and Mathew, *Plant Viruses Online* (http://image.fs.uidaho.edu/vide/). In certain embodiments of the invention rather than delivering a single viral vector to a plant cell, multiple different vectors are delivered which, together, allow for replication (and, optionally cell-to-cell and/or long distance movement) of viral vector(s). Some or all of the proteins may be encoded by the genome of transgenic plants. In certain aspects, described in further detail herein, these systems include one or more viral vector components.

Vector systems that include components of two heterologous plant viruses in order to achieve a system that readily infects a wide range of plant types and yet poses little or no risk of infectious spread. An exemplary system has been described previously (see, e.g., PCT Publication WO 00/25574 and U.S. Patent Publication 2005/0026291, both of which are incorporated herein by reference. As noted herein, in particular aspects of the present invention, viral vectors are applied to plants (e.g., plant, portion of plant, sprout, etc.), for example, through infiltration or mechanical inoculation, spray, etc. Where infection is to be accomplished by direct application of a viral genome to a plant, any available technique may be used to prepare the genome. For example, many viruses that are usefully employed in accordance with the present invention have ssRNA genomes. ssRNA may be prepared by transcription of a DNA copy of the genome, or by replication of an RNA copy, either in vivo or in vitro. Given the readily availability of easy-to-use in vitro transcription systems (e.g., SP6, T7, reticulocyte lysate, etc.), and also the convenience of maintaining a DNA copy of an RNA vector, it is expected that inventive ssRNA vectors will often be prepared by in vitro transcription, particularly with T7 or SP6 polymerase.

In certain embodiments of the invention rather than introducing a single viral vector type into a plant, multiple different viral vectors are introduced. Such vectors may, for example, trans-complement each other with respect to functions such as replication, cell-to-cell movement, and/or long distance movement. Vectors may contain different polynucleotides encoding *Trypanosoma* antigen of the invention. Selection for plant(s) or portions thereof that express multiple polypeptides encoding one or more *Trypanosoma* antigen(s) may be performed as described above for single polynucleotides or polypeptides.

Plant Tissue Expression Systems As discussed above, in accordance with the present invention, *Trypanosoma* antigens may be produced in any desirable system. Vector constructs and expression systems are well known in the art and may be adapted to incorporate use of *Trypanosoma* antigens provided herein. For example, transgenic plant production is known and generation of constructs and plant production may be adapted according to known techniques in the art. In some embodiments, transient expression systems in plants are desirable. Two of these systems include production of clonal roots and clonal plant systems, and derivatives thereof, as well as production of sprouted seedlings systems.

Clonal Plants

Clonal roots maintain RNA viral expression vectors and stably produce target protein uniformly in an entire root over extended periods of time and multiple subcultures. In contrast to plants, where a target gene is eliminated via recombination during cell-to-cell or long distance movement, in root cultures the integrity of a viral vector is maintained and levels of target protein produced over time are similar to those observed during initial screening. Clonal roots allow for ease of production of heterologous protein material for oral formulation of antigen and vaccine compositions. Methods and reagents for generating a variety of clonal entities derived from plants which are useful for production of antigen (e.g., antigen proteins of the invention) have been described previously and are known in the art (see, for example, PCT Publication WO 05/81905, which is incorporated herein by reference). Clonal entities include clonal root lines, clonal root cell lines, clonal plant cell lines, and clonal plants capable of production of antigen (e.g., antigen proteins of the invention). The invention further provides methods and reagents for expression of antigen polynucleotide and polypeptide products in clonal cell lines derived from various plant tissues (e.g., roots, leaves), and in whole plants derived from single cells (clonal plants). Such methods are typically based on use of plant viral vectors of various types.

For example, in one aspect, the invention provides methods of obtaining a clonal root line that expresses a polynucleotide encoding a *Trypanosoma* antigen of the invention comprising steps of: (i) introducing a viral vector that comprises a polynucleotide encoding a *Trypanosoma* antigen of the invention into a plant or portion thereof, and (ii) generating one or more clonal root lines from a plant. Clonal root lines may be generated, for example, by infecting a plant or plant portion (e.g., a harvested piece of leaf) with an *Agrobacterium* (e.g., *A. rhizogenes*) that causes formation of hairy roots. Clonal root lines can be screened in various ways to identify lines that maintain virus, lines that express a polynucleotide encoding a *Trypanosoma* antigen of the invention at high levels, etc. The invention further provides clonal root lines, e.g., clonal root lines produced according to inventive methods and further encompasses methods of expressing polynucleotides and producing polypeptide(s) encoding *Trypanosoma* antigen(s) of the invention using clonal root lines.

The invention further provides methods of generating a clonal root cell line that expresses a polynucleotide encoding a *Trypanosoma* antigen of the invention comprising steps of: (i) generating a clonal root line, cells of which contain a viral vector whose genome comprises a polynucleotide encoding a *Trypanosoma* antigen of the invention; (ii) releasing individual cells from a clonal root line; and (iii) maintaining cells under conditions suitable for root cell proliferation. The invention provides clonal root cell lines and methods of expressing polynucleotides and producing polypeptides using clonal root cell lines.

In one aspect, the invention provides methods of generating a clonal plant cell line that expresses a polynucleotide encoding a *Trypanosoma* antigen of the invention comprising steps of: (i) generating a clonal root line, cells of which contain a viral vector whose genome comprises a polynucleotide encoding a *Trypanosoma* antigen of the invention; (ii) releasing individual cells from a clonal root line; and (iii) maintaining cells in culture under conditions appropriate for plant cell proliferation. The invention further provides methods of generating a clonal plant cell line that expresses a polynucleotide encoding a *Trypanosoma* antigen of the invention comprising steps of: (i) introducing a viral vector that comprises a polynucleotide encoding a *Trypanosoma* antigen of the invention into cells of a plant cell line maintained in culture; and (ii) enriching for cells that contain viral vector. Enrichment may be performed, for example, by (i) removing a portion of cells from the culture; (ii) diluting removed cells so as to reduce cell concentration; (iii) allowing diluted cells to proliferate; and (iv) screening for cells that contain viral vector. Clonal plant cell lines may be used for production of a *Trypanosoma* antigen in accordance with the present invention.

The invention includes a number of methods for generating clonal plants, cells of which contain a viral vector that comprises a polynucleotide encoding *Trypanosoma* antigen of the invention. For example, the invention provides methods of generating a clonal plant that expresses a polynucleotide encoding *Trypanosoma* antigen of the invention comprising steps of: (i) generating a clonal root line, cells of which contain a viral vector whose genome comprises a polynucleotide encoding *Trypanosoma* antigen of the invention; (ii) releasing individual cells from a clonal root line; and (iii) maintaining released cells under conditions appropriate for formation of a plant. The invention further provides methods of generating a clonal plant that expresses a polynucleotide encoding *Trypanosoma* antigen of the invention comprising steps of: (i) generating a clonal plant cell line, cells of which contain a viral vector whose genome comprises a polynucleotide encoding a *Trypanosoma* antigen of the invention; and (ii) maintaining cells under conditions appropriate for formation of a plant. In general, clonal plants according to the invention can express any polynucleotide encoding a *Trypanosoma* antigen of the invention. Such clonal plants can be used for production of a antigen polypeptide.

As noted above, the present invention provides systems for expressing a polynucleotide or polynucleotide(s) encoding *Trypanosoma* antigen(s) of the invention in clonal root lines, clonal root cell lines, clonal plant cell lines (e.g., cell lines derived from leaf, stem, etc.), and in clonal plants. A polynucleotide encoding a *Trypanosoma* antigen of the invention is introduced into an ancestral plant cell using a plant viral vector whose genome includes polynucleotide encoding a *Trypanosoma* antigen of the invention operably linked to (i.e., under control of) a promoter. A clonal root line or clonal plant cell line is established from a cell containing virus according to any of several techniques further described below. The plant virus vector or portions thereof can be introduced into a plant cell by infection, by inoculation with a viral transcript or infectious cDNA clone, by electroporation, by T-DNA mediated gene transfer, etc.

The following sections describe methods for generating clonal root lines, clonal root cell lines, clonal plant cell lines, and clonal plants that express a polynucleotide encoding a *Trypanosoma* antigen of the invention are then described. A "root line" is distinguished from a "root cell line" in that a root line produces actual rootlike structures or roots while a root cell line consists of root cells that do not form rootlike structures. Use of the term "line" is intended to indicate that cells of the line can proliferate and pass genetic information on to progeny cells. Cells of a cell line typically proliferate in culture without being part of an organized structure such as those found in an intact plant. Use of the term "root line" is intended to indicate that cells in the root structure can proliferate without being part of a complete plant. It is noted that the term "plant cell" encompasses root cells. However, to distinguish the inventive methods for generating root lines and root cell lines from those used to directly generate plant cell lines from non-root tissue (as opposed to generating clonal plant cell lines from clonal root lines or clonal plants derived from clonal root lines), the terms "plant cell" and "plant cell line" as used herein generally refer to cells and cell lines that consist of non-root plant tissue. Plant cells can be, for example, leaf, stem, shoot, flower part, etc. It is noted that seeds can be derived from clonal plants generated as derived herein. Such seeds may contain viral vector as will plants obtained from such seeds. Methods for obtaining seed stocks are well known in the art (see, for example, U.S Patent Publication 2004/093643).

Clonal Root Lines

The present invention provides systems for generating a clonal root line in which a plant viral vector is used to direct expression of a polynucleotide encoding a *Trypanosoma* antigen of the invention. One or more viral expression vector(s) including a polynucleotide encoding a *Trypanosoma* antigen of the invention operably linked to a promoter is introduced into a plant or a portion thereof according to any of a variety of known methods. For example, plant leaves can be inoculated with viral transcripts. Vectors themselves may be directly applied to plants (e.g., via abrasive inoculations, mechanized spray inoculations, vacuum infiltration, particle bombardment, or electroporation). Alternatively or additionally, virions may be prepared (e.g., from already infected plants), and may be applied to other plants according to known techniques.

Where infection is to be accomplished by direct application of a viral genome to a plant, any available technique may be used to prepare viral genome. For example, many viruses that are usefully employed in accordance with the present invention have ssRNA genomes. ssRNA may be prepared by transcription of a DNA copy of the genome, or by replication of an RNA copy, either in vivo or in vitro. Given the readily available, easy-to-use in vitro transcription systems (e.g., SP6, T7, reticulocyte lysate, etc.), and also the convenience of maintaining a DNA copy of an RNA vector, it is expected that inventive ssRNA vectors will often be prepared by in vitro transcription, particularly with T7 or SP6 polymerase. Infectious cDNA clones can be used. Agrobacterially mediated gene transfer can be used to transfer viral nucleic acids such as viral vectors (either entire viral genomes or portions thereof) to plant cells using, e.g., agroinfiltration, according to methods known in the art.

A plant or plant portion may then be then maintained (e.g., cultured or grown) under conditions suitable for replication of viral transcript. In certain embodiments of the invention virus spreads beyond the initially inoculated cell, e.g., locally from cell to cell and/or systemically from an initially inoculated leaf into additional leaves. However, in some embodiments of the invention virus does not spread. Thus viral vector may contain genes encoding functional MP and/or CP, but may be lacking one or both of such genes. In general, viral vector is introduced into (infects) multiple cells in the plant or portion thereof.

Following introduction of viral vector into a plant, leaves are harvested. In general, leaves may be harvested at any time following introduction of a viral vector. However, it may be desirable to maintain a plant for a period of time following introduction of a viral vector into the plant, e.g., a period of time sufficient for viral replication and, optionally, spread of virus from the cells into which it was initially introduced. A clonal root culture (or multiple cultures) is prepared, e.g., by known methods further described below.

In general, any available method may be used to prepare a clonal root culture from a plant or plant tissue into which a viral vector has been introduced. One such method employs genes that exist in certain bacterial plasmids. These plasmids are found in various species of *Agrobacterium* that infect and transfer DNA to a wide variety of organisms. As a genus, *Agrobacteria* can transfer DNA to a large and diverse set of plant types including numerous dicot and monocot angiosperm species and gymnosperms (see, for example, Gelvin, 2003, *Microbiol. Mol. Biol. Rev.,* 67:16, and references therein, all of which are incorporated herein by reference). The molecular basis of genetic transformation of plant cells is transfer from bacterium and integration into plant nuclear genome of a region of a large tumor-inducing (Ti) or rhizogenic (Ri) plasmid that resides within various *Agrobacterial* species. This region is referred to as the T-region when present in the plasmid and as T-DNA when excised from plasmid. Generally, a single-stranded T-DNA molecule is transferred to a plant cell in naturally occurring *Agrobacterial* infection and is ultimately incorporated (in double-stranded form) into the genome. Systems based on Ti plasmids are widely used for introduction of foreign genetic material into plants and for production of transgenic plants.

Infection of plants with various *Agrobacterial* species and transfer of T-DNA has a number of effects. For example, *A. tumefaciens* causes crown gall disease while *A. rhizogenes* causes development of hairy roots at the site of infection, a condition known as "hairy root disease." Each root arises from a single genetically transformed cell. Thus root cells in roots are clonal, and each root represents a clonal population of cells. Roots produced by *A. rhizogenes* infection are characterized by a high growth rate and genetic stability (Giri et al., 2000, *Biotech. Adv.,* 18:1, and references therein, all of which are incorporated herein by reference). In addition, such roots are able to regenerate genetically stable plants (Giri 2000, supra).

In general, the present invention encompasses use of any strain of *Agrobacteria*, particularly *A. rhizogenes* strains, that is capable of inducing formation of roots from plant cells. As mentioned above, a portion of the Ri plasmid (Ri T-DNA) is responsible for causing hairy root disease. While transfer of this portion of the Ri plasmid to plant cells can conveniently be accomplished by infection with *Agrobacteria* harboring the Ri plasmid, the invention encompasses use of alternative methods of introducing the relevant region into a plant cell. Such methods include any available method of introducing genetic material into plant cells including, but not limited to, biolistics, electroporation, PEG-mediated DNA uptake, Ti-based vectors, etc. The relevant portions of Ri T-DNA can be introduced into plant cells by use of a viral vector. Ri genes can be included in the same vector that contains a polynucleotide encoding a *Trypanosoma* antigen of the invention or in a different viral vector, which can be the same or a different type to that of the vector that contains a polynucleotide encoding a *Trypanosoma* antigen of the invention. It is noted that the entire Ri T-DNA may not be required for production of hairy roots, and the invention encompasses use of portions of Ri T-DNA, provided that such portions contain sufficient genetic material to induce root formation, as known in the art. Additional genetic material, e.g., genes present within the Ri plasmid but not within T-DNA, may be transferred to a plant cell in accordance with the invention, particularly genes whose expression products facilitate integration of T-DNA into the plant cell DNA.

In order to prepare a clonal root line in accordance with certain embodiments of the invention, harvested leaf portions are contacted with *A. rhizogenes* under conditions suitable for infection and transformation. Leaf portions are maintained in culture to allow development of hairy roots. Each root is clonal, i.e., cells in the root are derived from a single ancestral cell into which Ri T-DNA was transferred. In accordance with the invention, a portion of such ancestral cells will contain a viral vector. Thus cells in a root derived from such an ancestral cell may contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within the clonal root, movement of viral vector within the root is not necessary to maintain viral vector throughout the root. Individual clonal hairy roots may be removed from the leaf portion and further cultured. Such roots are also referred to herein as root lines. Isolated clonal roots continue to grow following isolation.

A variety of different clonal root lines have been generated using inventive methods. These root lines were generated using viral vectors containing polynucleotide(s) encoding a *Trypanosoma* antigen of the invention (e.g., encoding including *Trypanosoma* protein(s), portions, fragments, domains, variants, and/or fusions thereof). Root lines were tested by Western blot. Root lines displayed a variety of different expression levels of various polypeptides. Root lines displaying high expression were selected and further cultured. These root lines were subsequently tested again and shown to maintain high levels of expression over extended periods of time, indicating stability. Expression levels were comparable to or greater than expression in intact plants infected with the same viral vector used to generate clonal root lines. In addition, stability of expression of root lines was superior to that obtained in plants infected with the same viral vector. Up to 80% of such virus-infected plants reverted to wild type after 2-3 passages. (Such passages involved inoculating plants with transcripts, allowing infection (local or systemic) to become established, taking a leaf sample, and inoculating fresh plants that are subsequently tested for expression).

Root lines may be cultured on a large scale for production of antigen of the invention polypeptides as discussed further below. It is noted that clonal root lines (and cell lines derived from clonal root lines) can generally be maintained in medium that does not include various compounds, e.g., plant growth hormones such as auxins, cytokinins, etc., that are typically employed in culture of root and plant cells. This feature greatly reduces expense associated with tissue culture, and the inventors expect that it will contribute significantly to economic feasibility of protein production using plants.

Any of a variety of methods may be used to select clonal roots that express a polynucleotide encoding *Trypanosoma* antigen(s) of the invention. Western blots, ELISA assays, etc., can be used to detect an encoded polypeptide. In the case of detectable markers such as GFP, alternative methods such as visual screens can be performed. If a viral vector that contains a polynucleotide that encodes a selectable marker is used, an appropriate selection can be imposed (e.g., leaf material and/or roots derived therefrom can be cultured in the presence of an appropriate antibiotic or nutritional condition and surviving roots identified and isolated). Certain viral vectors contain two or more polynucleotide(s) encoding *Trypanosoma* antigen(s) of the invention, e.g., two or more polynucleotides encoding different polypeptides. If one of these is a selectable or detectable marker, clonal roots that are selected or detected by selecting for or detecting expression of the marker will have a high probability of also expressing a second polynucleotide. Screening for root lines that contain particular polynucleotides can also be performed using PCR and other nucleic acid detection methods.

Alternatively or additionally, clonal root lines can be screened for presence of virus by inoculating host plants that will form local lesions as a result of virus infection (e.g., hypersensitive host plants). For example, 5 mg of root tissue can be homogenized in 50 ul of phosphate buffer and used to inoculate a single leaf of a tobacco plant. If virus is present in root cultures, within two to three days characteristic lesions will appear on infected leaves. This means that root line contains recombinant virus that carries a polynucleotide encoding a *Trypanosoma* antigen of the invention (a target gene). If no local lesions are formed, there is no virus, and the root line is rejected as negative. This method is highly time and cost efficient. After initially screening for the presence of virus, roots that contain virus may be subjected to secondary screening, e.g., by Western blot or ELISA to select high expressers. Additional screens, e.g., screens for rapid growth, growth in particular media or under particular environmental conditions, etc., can be applied. These screening methods may, in general, be applied in the development of any of clonal root lines, clonal root cell lines, clonal plant cell lines, and/or clonal plants described herein.

As will be evident to one of ordinary skill in the art, a variety of modifications may be made to the description of the inventive methods for generating clonal root lines that contain a viral vector. Such modifications are within the scope of the invention. For example, while it is generally desirable to introduce viral vector into an intact plant or portion thereof prior to introduction of Ri T-DNA genes, in certain embodiments of the invention the Ri-DNA is introduced prior to introducing viral vector. In addition, it is possible to contact intact plants with *A. rhizogenes* rather than harvesting leaf portions and then exposing them to bacterium.

Other methods of generating clonal root lines from single cells of a plant or portion thereof that harbor a viral vector can be used (i.e., methods not using *A. rhizogenes* or genetic material from the Ri plasmid). For example, treatment with certain plant hormones or combinations of plant hormones is known to result in generation of roots from plant tissue.

Clonal Cell Lines Derived from Clonal Root Lines

As described above, the invention provides methods for generating clonal root lines, wherein cells in root lines contain a viral vector. As is well known in the art, a variety of different cell lines can be generated from roots. For example, root cell lines can be generated from individual root cells obtained from a root using a variety of known methods. Such root cell lines may be obtained from various different root cell types within the root. In general, root material is harvested and dissociated (e.g., physically and/or enzymatically digested) to release individual root cells, which are then further cultured. Complete protoplast formation is generally not necessary. If desired, root cells can be plated at very dilute cell concentrations, so as to obtain root cell lines from single root cells. Root cell lines derived in this manner are clonal root cell lines containing viral vector. Such root cell lines therefore exhibit stable expression of a polynucleotide encoding a *Trypanosoma* antigen of the invention. Clonal plant cell lines can be obtained in a similar manner from clonal roots, e.g., by culturing dissociated root cells in the presence of appropriate plant hormones. Screens and successive rounds of enrichment can be used to identify cell lines that express a polynucleotide encoding a *Trypanosoma* antigen of the invention at high levels. However, if the clonal root line from which the cell line is derived already expresses at high levels, such additional screens may be unnecessary.

As in the case of the clonal root lines, cells of a clonal root cell line are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within a clonal root cell line, movement of viral vector among cells is not necessary to maintain viral vector. Clonal root cell lines can be used for production of a polynucleotide encoding *Trypanosoma* antigen of the invention as described below.

Clonal Plant Cell Lines

The present invention provides methods for generating a clonal plant cell line in which a plant viral vector is used to direct expression of a polynucleotide encoding a *Trypanosoma* antigen of the invention. According to the inventive method, one or more viral expression vector(s) including a polynucleotide encoding a *Trypanosoma* antigen of the invention operably linked to a promoter is introduced into cells of a plant cell line that is maintained in cell culture. A number of plant cell lines from various plant types are known in the art, any of which can be used. Newly derived cell lines can be generated according to known methods for use in practicing the invention. A viral vector is introduced into cells of a plant cell line according to any of a number of methods. For example, protoplasts can be made and viral transcripts then electroporated into cells. Other methods of introducing a plant viral vector into cells of a plant cell line can be used.

A method for generating clonal plant cell lines in accordance with the invention and a viral vector suitable for introduction into plant cells (e.g., protoplasts) can be used as follows: Following introduction of viral vector, a plant cell line may be maintained in tissue culture. During this time viral vector may replicate, and polynucleotide(s) encoding a *Trypanosoma* antigen(s) of the invention may be expressed. Clonal plant cell lines are derived from culture, e.g., by a process of successive enrichment. For example, samples may be removed from culture, optionally with dilution so that the concentration of cells is low, and plated in Petri dishes in individual droplets. Droplets are then maintained to allow cell division.

It will be appreciated that droplets may contain a variable number of cells, depending on the initial density of the culture and the amount of dilution. Cells can be diluted such that most droplets contain either 0 or 1 cell if it is desired to obtain clonal cell lines expressing a polynucleotide encoding a *Trypanosoma* antigen of the invention after only a single round of enrichment. However, it can be more efficient to select a concentration such that multiple cells are present in each droplet and then screen droplets to identify those that contain expressing cells. In general, any appropriate screening procedure can be employed. For example, selection or detection of a detectable marker such as GFP can be used. Western blots or ELISA assays can be used. Individual droplets (100 ul) contain more than enough cells for performance of these assays. Multiple rounds of enrichment are performed to isolate successively higher expressing cell lines. Single clonal plant cell lines (i.e., populations derived from a single ancestral cell) can be generated by further limiting dilution using standard methods for single cell cloning. However, it is not necessary to isolate individual clonal lines. A population containing multiple clonal cell lines can be used for expression of a polynucleotide encoding one or more *Trypanosoma* antigen(s) of the invention.

In general, certain considerations described above for generation of clonal root lines apply to the generation of clonal plant cell lines. For example, a diversity of viral vectors containing one or more polynucleotide(s) encoding a *Trypanosoma* antigen(s) of the invention can be used as combinations of multiple different vectors. Similar screening methods can be used. As in the case of clonal root lines and clonal root cell lines, cells of a clonal plant cell line are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within a clonal plant cell line, movement of viral vector among cells is not necessary to maintain viral vector. The clonal plant cell line can be used for production of a polypeptide encoding a *Trypanosoma* antigen of the invention as described below.

Clonal Plants

Clonal plants can be generated from clonal roots, clonal root cell lines, and/or clonal plant cell lines produced according to various methods described above. Methods for the generation of plants from roots, root cell lines, and plant cell lines such as clonal root lines, clonal root cell lines, and clonal plant cell lines described herein are well known in the art (see, e.g., Peres et al., 2001, *Plant Cell, Tissue, Organ Culture*, 65:37; and standard reference works on plant molecular biology and biotechnology cited elsewhere herein). The invention therefore provides a method of generating a clonal plant comprising steps of (i) generating a clonal root line, clonal root cell line, or clonal plant cell line according to any of the inventive methods described above; and (ii) generating a whole plant from a clonal root line, clonal root cell line, or clonal plant. Clonal plants may be propagated and grown according to standard methods.

As in the case of clonal root lines, clonal root cell lines, and clonal plant cell lines, cells of a clonal plant are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within the clonal plant, movement of viral vector is not necessary to maintain viral vector.

Sprouts and Sprouted Seedling Plant Expression Systems

Systems and reagents for generating a variety of sprouts and sprouted seedlings which are useful for production of *Trypanosoma* antigen(s) according to the present invention have been described previously and are known in the art (see, for example, PCT Publication WO 04/43886, which is incorporated herein by reference). The present invention further provides sprouted seedlings, which may be edible, as a biomass containing a *Trypanosoma* antigen. In certain aspects, biomass is provided directly for consumption of antigen containing compositions. In some aspects, biomass is processed prior to consumption, for example, by homogenizing, crushing, drying, or extracting. In certain aspects, *Trypanosoma* antigen is purified from biomass and formulated into a pharmaceutical composition.

Additionally provided are methods for producing *Trypanosoma* antigen(s) in sprouted seedlings that can be consumed or harvested live (e.g., sprouts, sprouted seedlings of the *Brassica* genus). In certain aspects, the present invention involves growing a seed to an edible sprouted seedling in a contained, regulatable environment (e.g., indoors, in a container, etc.). A seed can be a genetically engineered seed that contains an expression cassette encoding a *Trypanosoma* antigen, which expression is driven by an exogenously inducible promoter. A variety of exogenously inducible promoters can be used that are inducible, for example, by light, heat, phytohormones, nutrients, etc.

In related embodiments, the present invention provides methods of producing *Trypanosoma* antigen(s) in sprouted seedlings by first generating a seed stock for a sprouted seedling by transforming plants with an expression cassette that encodes *Trypanosoma* antigen using an *Agrobacterium* transformation system, wherein expression of a *Trypanosoma* antigen is driven by an inducible promoter. Transgenic seeds can be obtained from a transformed plant, grown in a contained, regulatable environment, and induced to express a *Trypanosoma* antigen.

In some embodiments methods are provided that involves infecting sprouted seedlings with a viral expression cassette encoding a *Trypanosoma* antigen, expression of which may be driven by any of a viral promoter or an inducible promoter. Sprouted seedlings are grown for two to fourteen days in a contained, regulatable environment or at least until sufficient levels of *Trypanosoma* antigen have been obtained for consumption or harvesting.

The present invention further provides systems for producing *Trypanosoma* antigen(s) in sprouted seedlings that include a housing unit with climate control and a sprouted seedling containing an expression cassette that encodes one or more *Trypanosoma* antigens, wherein expression is driven by a constitutive or inducible promoter. Systems can provide unique advantages over the outdoor environment or greenhouse, which cannot be controlled. Thus, the present invention enables a grower to precisely time the induction of expression of *Trypanosoma* antigen. It can greatly reduce time and cost of producing *Trypanosoma* antigen(s).

In certain aspects, transiently transfected sprouts contain viral vector sequences encoding an inventive *Trypanosoma* antigen. Seedlings are grown for a time period so as to allow for production of viral nucleic acid in sprouts, followed by a period of growth wherein multiple copies of virus are produced, thereby resulting in production of *Trypanosoma* antigen(s).

In certain aspects, genetically engineered seeds or embryos that contain a nucleic acid encoding *Trypanosoma* antigen(s) are grown to sprouted seedling stage in a contained, regulatable environment. The contained, regulatable environment may be a housing unit or room in which seeds can be grown indoors. All environmental factors of a contained, regulatable environment may be controlled. Since sprouts do not require light to grow, and lighting can be expensive, genetically engineered seeds or embryos may be grown to sprouted seedling stage indoors in the absence of light.

Other environmental factors that can be regulated in a contained, regulatable environment of the present invention include temperature, humidity, water, nutrients, gas (e.g., $O_2$ or $CO_2$ content or air circulation), chemicals (small molecules such as sugars and sugar derivatives or hormones such as such as phytohormones gibberellic or absisic acid, etc.) and the like.

According to certain methods of the present invention, expression of a nucleic acid encoding a *Trypanosoma* antigen may be controlled by an exogenously inducible promoter. Exogenously inducible promoters are caused to increase or decrease expression of a nucleic acid in response to an external, rather than an internal stimulus. A number of environmental factors can act as inducers for expression of nucleic acids carried by expression cassettes of genetically engineered sprouts. A promoter may be a heat-inducible promoter, such as a heat-shock promoter. For example, using as heat-shock promoter, temperature of a contained environment may simply be raised to induce expression of a nucleic acid. Other promoters include light inducible promoters. Light-inducible promoters can be maintained as constitutive promoters if light in a contained regulatable environment is always on. Alternatively or additionally, expression of a nucleic acid can be turned on at a particular time during development by simply turning on the light. A promoter may be a chemically inducible promoter is used to induce expression of a nucleic acid. According to these embodiments, a chemical could simply be misted or sprayed onto seed, embryo, or seedling to induce expression of nucleic acid. Spraying and misting can be precisely controlled and directed onto target seed, embryo, or seedling to which it is intended. The contained environment is devoid of wind or air currents, which could disperse chemical away from intended target, so that the chemical stays on the target for which it was intended.

According to the present invention, time of expression is induced can be selected to maximize expression of a *Trypanosoma* antigen in sprouted seedling by the time of harvest. Inducing expression in an embryo at a particular stage of growth, for example, inducing expression in an embryo at a particular number of days after germination, may result in maximum synthesis of a *Trypanosoma* antigen at the time of harvest. For example, inducing expression from the promoter 4 days after germination may result in more protein synthesis than inducing expression from the promoter after 3 days or after 5 days. Those skilled in the art will appreciate that maximizing expression can be achieved by routine experimentation. In certain methods, sprouted seedlings are harvested at about 1, 2, 3, 4, 5, 6, 7, 8, 9, 10, 11, or 12 days after germination.

In cases where the expression vector has a constitutive promoter instead of an inducible promoter, sprouted seedling may be harvested at a certain time after transformation of sprouted seedling. For example, if a sprouted seedling were virally transformed at an early stage of development, for example, at embryo stage, sprouted seedlings may be harvested at a time when expression is at its maximum post-transformation, e.g., at about 1, 2, 3, 4, 5, 6, 7, 8, 9, 10, 11, 12, 13, or 14 days post-transformation. It could be that sprouts develop one, two, three or more months post-transformation, depending on germination of seed.

Generally, once expression of *Trypanosoma* antigen(s) begins, seeds, embryos, or sprouted seedlings are allowed to grow until sufficient levels of *Trypanosoma* antigen(s) are expressed. In certain aspects, sufficient levels are levels that would provide a therapeutic benefit to a patient if harvested biomass were eaten raw. Alternatively or additionally, sufficient levels are levels from which *Trypanosoma* antigen can be concentrated or purified from biomass and formulated into a pharmaceutical composition that provides a therapeutic benefit to a patient upon administration. Typically, *Trypanosoma* antigen is not a protein expressed in sprouted seedling in nature. At any rate, *Trypanosoma* antigen is typically expressed at concentrations above that which would be present in the sprouted seedling in nature.

Once expression of *Trypanosoma* antigen is induced, growth is allowed to continue until sprouted seedling stage, at which time sprouted seedlings are harvested. Sprouted seedlings can be harvested live. Harvesting live sprouted seedlings has several advantages including minimal effort and breakage. Sprouted seedlings of the present invention may be grown hydroponically, making harvesting a simple matter of lifting a sprouted seedling from its hydroponic solution. No soil is required for growth of sprouted seedlings of the invention, but may be provided if deemed necessary or desirable by the skilled artisan. Because sprouts can be grown without soil, no cleansing of sprouted seedling material is required at the time of harvest. Being able to harvest the sprouted seedling directly from its hydroponic environment without washing or scrubbing minimizes breakage of harvested material. Breakage and wilting of plants induces apoptosis. During apoptosis, certain proteolytic enzymes become active, which can degrade pharmaceutical protein expressed in the sprouted seedling, resulting in decreased therapeutic activity of the protein. Apoptosis-induced proteolysis can significantly decrease yield of protein from mature plants. Using methods of the present invention, apoptosis may be avoided when no harvesting takes place until the moment proteins are extracted from the plant.

For example, live sprouts may be ground, crushed, or blended to produce a slurry of sprouted seedling biomass, in a buffer containing protease inhibitors. Buffer may be maintained at about 4° C. In some aspects, sprouted seedling biomass is air-dried, spray dried, frozen, or freeze-dried. As in mature plants, some of these methods, such as air-drying, may result in a loss of activity of pharmaceutical protein. However, because sprouted seedlings are very small and have a large surface area to volume ratio, this is much less likely to occur. Those skilled in the art will appreciate that many techniques for harvesting biomass that minimize proteolysis of expressed protein are available and could be applied to the present invention.

In some embodiments, sprouted seedlings are edible. In certain embodiments, sprouted seedlings expressing sufficient levels of *Trypanosoma* antigens are consumed upon harvesting (e.g., immediately after harvest, within minimal period following harvest) so that absolutely no processing occurs before sprouted seedlings are consumed. In this way, any harvest-induced proteolytic breakdown of *Trypanosoma* antigen before administration of *Trypanosoma* antigen to a patient in need of treatment is minimized. For example, sprouted seedlings that are ready to be consumed can be delivered directly to a patient. Alternatively or additionally, genetically engineered seeds or embryos are delivered to a patient in need of treatment and grown to sprouted seedling stage by a patient. In one aspect, a supply of genetically engineered sprouted seedlings are provided to a patient, or to a doctor who will be treating patients, so that a continual stock of sprouted seedlings expressing certain desirable *Trypanosoma* antigens may be cultivated. This may be particularly valuable for populations in developing countries, where expensive pharmaceuticals are not affordable or deliverable. The ease with which sprouted seedlings of the invention can be grown makes sprouted seedlings of the present invention particularly desirable for such developing populations.

The regulatable nature of the contained environment imparts advantages to the present invention over growing plants in the outdoor environment. In general, growing genetically engineered sprouted seedlings that express pharmaceutical proteins in plants provides a pharmaceutical product faster (because plants are harvested younger) and with less effort, risk, and regulatory considerations than growing genetically engineered plants. The contained, regulatable environment used in the present invention reduces or eliminates risk of cross-pollinating plants in nature.

For example, a heat inducible promoter likely would not be used outdoors because outdoor temperature cannot be controlled. The promoter would be turned on any time the outdoor temperature rose above a certain level. Similarly, the promoter would be turned off every time the outdoor temperature dropped. Such temperature shifts could occur in a single day, for example, turning expression on in the daytime and off at night. A heat inducible promoter, such as those described herein, would not even be practical for use in a greenhouse, which is susceptible to climatic shifts to almost the same degree as outdoors. Growth of genetically engineered plants in a greenhouse is quite costly. In contrast, in the present system, every variable can be controlled so that the maximum amount of expression can be achieved with every harvest.

In certain embodiments, sprouted seedlings of the present invention are grown in trays that can be watered, sprayed, or misted at any time during development of sprouted seedling. For example, a tray may be fitted with one or more watering, spraying, misting, and draining apparatus that can deliver and/or remove water, nutrients, chemicals etc. at specific time and at precise quantities during development of the sprouted seedling. For example, seeds require sufficient moisture to keep them damp. Excess moisture drains through holes in trays into drains in the floor of the room. Typically, drainage water is treated as appropriate for removal of harmful chemicals before discharge back into the environment.

Another advantage of trays is that they can be contained within a very small space. Since no light is required for sprouted seedlings to grow, trays containing seeds, embryos, or sprouted seedlings may be tightly stacked vertically on top of one another, providing a large quantity of biomass per unit floor space in a housing facility constructed specifically for these purposes. In addition, stacks of trays can be arranged in horizontal rows within the housing unit. Once seedlings have grown to a stage appropriate for harvest (about two to fourteen days) individual seedling trays are moved into a processing facility, either manually or by automatic means, such as a conveyor belt.

The system of the present invention is unique in that it provides a sprouted seedling biomass, which is a source of a *Trypanosoma* antigen(s). Whether consumed directly or processed into the form of a pharmaceutical composition, because sprouted seedlings are grown in a contained, regulatable environment, sprouted seedling biomass and/or pharmaceutical composition derived from biomass can be provided to a consumer at low cost. In addition, the fact that the conditions for growth of sprouted seedlings can be controlled makes the quality and purity of product consistent. The contained, regulatable environment of the invention obviates many safety regulations of the EPA that can prevent scientists from growing genetically engineered agricultural products out of doors.

Transformed Sprouts

A variety of methods can be used to transform plant cells and produce genetically engineered sprouted seedlings. Two available methods for transformation of plants that require that transgenic plant cell lines be generated in vitro, followed by regeneration of cell lines into whole plants include *Agrobacterium tumefaciens* mediated gene transfer and microprojectile bombardment or electroporation. Viral transformation is a more rapid and less costly method of transforming embryos and sprouted seedlings that can be harvested without an experimental or generational lag prior to obtaining desired product. For any of these techniques, the skilled artisan would appreciate how to adjust and optimize transformation protocols that have traditionally been used for plants, seeds, embryos, or spouted seedlings.

*Agrobacterium* Transformation Expression Cassettes

*Agrobacterium* is a representative genus of the gram-negative family Rhizobiaceae. This species is responsible for plant tumors such as crown gall and hairy root disease. In dedifferentiated plant tissue, which is characteristic of tumors, amino acid derivatives known as opines are produced by the *Agrobacterium* and catabolized by the plant. The bacterial genes responsible for expression of opines are a convenient source of control elements for chimeric expression cassettes. According to the present invention, *Agrobacterium* transformation system may be used to generate edible sprouted seedlings, which are merely harvested earlier than mature plants. *Agrobacterium* transformation methods can easily be applied to regenerate sprouted seedlings expressing *Trypanosoma* antigens.

In general, transforming plants involves transformation of plant cells grown in tissue culture by co-cultivation with an *Agrobacterium tumefaciens* carrying a plant/bacterial vector. The vector contains a gene encoding a *Trypanosoma* antigen. The *Agrobacterium* transfers vector to plant host cell and is then eliminated using antibiotic treatment. Transformed plant cells expressing *Trypanosoma* antigen are selected, differentiated, and finally regenerated into complete plantlets (Hellens et al., 2000, *Plant Mol. Biol.,* 42:819; Pilon-Smits et al., 1999, *Plant Physiolog.,* 119:123; Barfield et al., 1991, *Plant Cell Reports,* 10:308; and Riva et al., 1998, *J. Biotech.,* 1 (3); each of which is incorporated by reference herein).

Expression vectors for use in the present invention include a gene (or expression cassette) encoding a *Trypanosoma* antigen designed for operation in plants, with companion sequences upstream and downstream of the expression cassette. Companion sequences are generally of plasmid or viral origin and provide necessary characteristics to the vector to transfer DNA from bacteria to the desired plant host.

The basic bacterial/plant vector construct may desirably provide a broad host range prokaryote replication origin, a prokaryote selectable marker. Suitable prokaryotic selectable markers include resistance toward antibiotics such as ampicillin or tetracycline. Other DNA sequences encoding additional functions that are well known in the art may be present in the vector.

*Agrobacterium* T-DNA sequences are required for *Agrobacterium* mediated transfer of DNA to the plant chromosome. The tumor-inducing genes of T-DNA are typically removed and replaced with sequences encoding a *Trypanosoma* antigen. T-DNA border sequences are retained because they initiate integration of the T-DNA region into the plant genome. If expression of *Trypanosoma* antigen is not readily amenable to detection, the bacterial/plant vector construct may include a selectable marker gene suitable for determining if a plant cell has been transformed, e.g., nptII kanamycin resistance gene. On the same or different bacterial/plant vector (Ti plasmid) are Ti sequences. Ti sequences include virulence genes, which encode a set of proteins responsible for excision, transfer and integration of T-DNA into the plant genome (Schell, 1987, *Science,* 237:1176). Other sequences suitable for permitting integration of heterologous sequence into the plant genome may include transposon sequences, and the like, for homologous recombination.

Certain constructs will include an expression cassette encoding an antigen protein. One, two, or more expression cassettes may be used in a given transformation. The recombinant expression cassette contains, in addition to a *Trypanosoma* antigen encoding sequence, at least the following elements: a promoter region, plant 5' untranslated sequences, initiation codon (depending upon whether or not an expressed gene has its own), and transcription and translation termination sequences. In addition, transcription and translation terminators may be included in expression cassettes or chimeric genes of the present invention. Signal secretion sequences that allow processing and translocation of a protein, as appropriate, may be included in the expression cassette. A variety of promoters, signal sequences, and transcription and translation terminators are described, for example, in Lawton et al. (1987, *Plant Mol. Biol.,* 9:315) and in U.S. Pat. No. 5,888,789 (both of which are incorporated herein by reference). In addition, structural genes for antibiotic resistance are commonly utilized as a selection factor (Fraley et al. 1983, *Proc. Natl. Acad. Sci., USA,* 80:4803, incorporated herein by reference). Unique restriction enzyme sites at the 5' and 3' ends of a cassette allow for easy insertion into a pre-existing vector. Other binary vector systems for *Agrobacterium*-mediated transformation, carrying at least one T-DNA border sequence are described (PCT/EP99/07414, incorporated herein by reference).

Regeneration

Seeds of transformed plants may be harvested, dried, cleaned, and tested for viability and for the presence and expression of a desired gene product. Once this has been determined, seed stock is typically stored under appropriate conditions of temperature, humidity, sanitation, and security to be used when necessary. Whole plants may then be regenerated from cultured protoplasts, e.g., as described in Evans et al. (*Handbook of Plant Cell Cultures*, Vol. 1, MacMillan Publishing Co., New York, N.Y., 1983, incorporated herein by reference); and in Vasil (ed., *Cell Culture and Somatic Cell Genetics of Plants*, Acad. Press, Orlando, Fla., Vol. I, 1984, and Vol. III, 1986, incorporated herein by reference). In certain aspects, plants are regenerated only to sprouted seedling stage. In some aspects, whole plants are regenerated to produce seed stocks and sprouted seedlings are generated from seeds of the seed stock.

All plants from which protoplasts can be isolated and cultured to give whole, regenerated plants can be transformed by the present invention so that whole plants are recovered that contain a transferred gene. It is known that practically all plants can be regenerated from cultured cells or tissues, including, but not limited to, all major species of plants that produce edible sprouts. Some suitable plants include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower etc.

Means for regeneration vary from one species of plants to the next. However, those skilled in the art will appreciate that generally a suspension of transformed protoplants containing copies of a heterologous gene is first provided. Callus tissue is formed and shoots may be induced from callus and subsequently rooted. Alternatively or additionally, embryo formation can be induced from a protoplast suspension. These embryos germinate as natural embryos to form plants. Steeping seed in water or spraying seed with water to increase the moisture content of the seed to between 35-45% initiates germination. For germination to proceed, seeds are typically maintained in air saturated with water under controlled temperature and airflow conditions. The culture media will generally contain various amino acids and hormones, such as auxin and cytokinins. It is advantageous to add glutamic acid and proline to the medium, especially for such species as alfalfa. Shoots and roots normally develop simultaneously.

Efficient regeneration will depend on the medium, the genotype, and the history of the culture. If these three variables are controlled, then regeneration is fully reproducible and repeatable.

The mature plants, grown from the transformed plant cells, are selfed and non-segregating, homozygous transgenic plants are identified. The inbred plant produces seeds containing inventive antigen-encoding sequences. Such seeds can be germinated and grown to sprouted seedling stage to produce *Trypanosoma* antigen(s) according to the present invention.

In related embodiments, seeds of the present invention may be formed into seed products and sold with instructions on how to grow seedlings to the appropriate sprouted seedling stage for administration or harvesting into a pharmaceutical composition. In some related embodiments, hybrids or novel varieties embodying desired traits may be developed from inbred plants of the invention.

Direct Integration

Direct integration of DNA fragments into the genome of plant cells by microprojectile bombardment or electroporation may be used in the present invention (see, e.g., Kikkert, et al., 1999, *Plant: J. Tiss. Cult. Assoc.*, 35:43; Bates, 1994, *Mol. Biotech.*, 2:135). More particularly, vectors that express *Trypanosoma* antigen(s) of the present invention can be introduced into plant cells by a variety of techniques. As described above, vectors may include selectable markers for use in plant cells. Vectors may include sequences that allow their selection and propagation in a secondary host, such as sequences containing an origin of replication and selectable marker. Typically, secondary hosts include bacteria and yeast. In one embodiment, a secondary host is bacteria (e.g., *Escherichia coli*, the origin of replication is a colE1-type origin of replication) and a selectable marker is a gene encoding ampicillin resistance. Such sequences are well known in the art and are commercially available (e.g., Clontech, Palo Alto, Calif. or Stratagene, La Jolla, Calif.).

Vectors of the present invention may be modified to intermediate plant transformation plasmids that contain a region of homology to an *Agrobacterium tumefaciens* vector, a T-DNA border region from *Agrobacterium tumefaciens*, and antigen encoding nucleic acids or expression cassettes described above. Further vectors may include a disarmed plant tumor inducing plasmid of *Agrobacterium tumefaciens*.

According to this embodiment, direct transformation of vectors invention may involve microinjecting vectors directly into plant cells by use of micropipettes to mechanically transfer recombinant DNA (see, e.g., Crossway, 1985, *Mol. Gen. Genet.*, 202:179, incorporated herein by reference). Genetic material may be transferred into a plant cell using polyethylene glycols (see, e.g., Krens et al., 1982, *Nature* 296:72). Another method of introducing nucleic acids into plants via high velocity ballistic penetration by small particles with a nucleic acid either within the matrix of small beads or particles, or on the surface (see, e.g., Klein et al., 1987, *Nature* 327:70; Knudsen et al., *Planta*, 185:330). Yet another method of introduction is fusion of protoplasts with other entities, either minicells, cells, lysosomes, or other fusible lipid-surfaced bodies (see, e.g., Fraley et al., 1982, *Proc. Natl. Acad. Sci., USA*, 79:1859). Vectors of the invention may be introduced into plant cells by electroporation (see, e.g., Fromm et al. 1985, *Proc. Natl. Acad. Sci., USA*, 82:5824). According to this technique, plant protoplasts are electroporated in the presence of plasmids containing a gene construct. Electrical impulses of high field strength reversibly permeabilize biomembranes allowing introduction of pasmids. Electroporated plant protoplasts reform the cell wall divide and form plant callus, which can be regenerated to form sprouted seedlings of the invention. Those skilled in the art will appreciate how to utilize these methods to transform plants cells that can be used to generate edible sprouted seedlings.

Viral Transformation

Similar to conventional expression systems, plant viral vectors can be used to produce full-length proteins, including full length antigen. According to the present invention, plant virus vectors may be used to infect and produce antigen(s) in seeds, embryos, sprouted seedlings, etc. Viral system that can be used to express everything from short peptides to large complex proteins. Specifically, using tobamoviral vectors is described, for example, by McCormick et al. (1999, *Proc. Natl. Acad. Sci., USA*, 96:703; Kumagai et al. 2000, *Gene*, 245:169; and Verch et al., 1998, *J. Immunol. Methods*, 220: 69; all of which are incorporated herein by reference). Thus, plant viral vectors have a demonstrated ability to express short peptides as well as large complex proteins.

In certain embodiments, transgenic sprouts, which express *Trypanosoma* antigen, are generated utilizing a host/virus system. Transgenic sprouts produced by viral infection provide a source of transgenic protein that has already been demonstrated to be safe. For example, sprouts are free of contamination with animal pathogens. Unlike, for example, tobacco, proteins from an edible sprout could at least in theory be used in oral applications without purification, thus significantly reducing costs. In addition, a virus/sprout system offers a much simpler, less expensive route for scale-up and manufacturing, since trangenes are introduced into virus, which can be grown up to a commercial scale within a few days. In contrast, transgenic plants can require up to 5-7 years before sufficient seed or plant material is available for large-scale trials or commercialization.

According to the present invention, plant RNA viruses have certain advantages, which make them attractive as vectors for foreign protein expression. The molecular biology and pathology of a number of plant RNA viruses are well characterized and there is considerable knowledge of virus biology, genetics, and regulatory sequences. Most plant RNA viruses have small genomes and infectious cDNA clones are available to facilitate genetic manipulation. Once infectious virus material enters a susceptible host cell, it replicates to high levels and spreads rapidly throughout the entire sprouted seedling (one to ten days post inoculation). Virus particles are easily and economically recovered from infected sprouted seedling tissue. Viruses have a wide host range, enabling use of a single construct for infection of several susceptible species. These characteristics are readily transferable to sprouts.

Foreign sequences can be expressed from plant RNA viruses, typically by replacing one of the viral genes with desired sequence, by inserting foreign sequences into the virus genome at an appropriate position, or by fusing foreign peptides to structural proteins of a virus. Moreover, any of these approaches can be combined to express foreign sequences by trans-complementation of vital functions of a virus. A number of different strategies exist as tools to express foreign sequences in virus-infected plants using tobacco mosaic virus (TMV), alfalfa mosaic virus (AlMV), and chimeras thereof.

The genome of AlMV is a representative of the Bromoviridae family of viruses and consists of three genomic RNAs (RNAs1-3) and subgenomic RNA (RNA4). Genomic RNAs1 and 2 encode virus replicase proteins P1 and P2, respectively. Genomic RNA3 encodes cell-to-cell movement protein P3 and coat protein (CP). CP is translated from subgenomic RNA4, which is synthesized from genomic RNA3, and is required to start infection. Studies have demonstrated the involvement of CP in multiple functions, including genome activation, replication, RNA stability, symptom formation, and RNA encapsidation (see e.g., Bol et al., 1971, *Virology*, 46:73; Van Der Vossen et al., 1994, *Virology* 202:891; Yusibov et al., *Virology*, 208:405; Yusibov et al., 1998, *Virology*, 242:1; Bol et al., (Review, 100 refs.), 1999, *J. Gen. Virol.*, 80:1089; De Graaff, 1995, *Virology*, 208:583; Jaspars et al., 1974, *Adv. Virus Res.*, 19:37; Loesch-Fries, 1985, *Virology*, 146:177; Neeleman et al., 1991, *Virology*, 181:687; Neeleman et al., 1993, *Virology*, 196:883; Van Der Kuyl et al., 1991, *Virology*, 183:731; and Van Der Kuyl et al., 1991, *Virology*, 185:496).

Encapsidation of viral particles is typically required for long distance movement of virus from inoculated to un-inoculated parts of seed, embryo, or sprouted seedling and for systemic infection. According to the present invention, inoculation can occur at any stage of plant development. In embryos and sprouts, spread of inoculated virus should be very rapid. Virions of AlMV are encapsidated by a unique CP (24 kD), forming more than one type of particle. The size (30 to 60 nm in length and 18 nm in diameter) and shape (spherical, ellipsoidal, or bacilliform) of the particle depends on the size of the encapsidated RNA. Upon assembly, the N-terminus of AlMV CP is thought to be located on the surface of the virus particles and does not appear to interfere with virus assembly (Bol et al., 1971, *Virology,* 6:73). Additionally, ALMV CP with an additional 38-amino acid peptide at its N-terminus forms particles in vitro and retains biological activity (Yusibov et al., 1995, *J. Gen. Virol.,* 77:567).

AlMV has a wide host range, which includes a number of agriculturally valuable crop plants, including plant seeds, embryos, and sprouts. Together, these characteristics make ALMV CP an excellent candidate as a carrier molecule and AlMV an attractive candidate vector for expression of foreign sequences in a plant at the sprout stage of development. Moreover, upon expression from a heterologous vector such as TMV, AlMV CP encapsidates TMV genome without interfering with virus infectivity (Yusibov et al., 1997, *Proc. Natl. Acad. Sci., USA,* 94:5784, incorporated herein by reference). This allows use of TMV as a carrier virus for AlMV CP fused to foreign sequences.

TMV, the prototype of tobamoviruses, has a genome consisting of a single plus-sense RNA encapsidated with a 17.0 kD CP, which results in rod-shaped particles (300 nm in length). CP is the only structural protein of TMV and is required for encapsidation and long distance movement of virus in an infected host (Saito et al., 1990, *Virology* 176:329). 183 and 126 kD proteins are translated from genomic RNA and are required for virus replication (Ishikawa et al., 1986, *Nucleic Acids Res.,* 14:8291). 30 kD protein is the cell-to-cell movement protein of virus (Meshi et al., 1987, *EMBO J.,* 6:2557). Movement and coat proteins are translated from subgenomic mRNAs (Hunter et al., 1976, *Nature,* 260:759; Bruening et al., 1976, *Virology,* 71:498; and Beachy et al., 1976, *Virology,* 73:498, each of which is incorporated herein by reference).

Other methods of transforming plant tissues include transforming the flower of a plant. Transformation of *Arabidopsis thaliana* can be achieved by dipping plant flowers into a solution of *Agrobacterium tumefaciens* (Curtis et al., 2001, *Transgenic Res.,* 10:363; and Qing et al., 2000, *Molecular Breeding: New Strategies in Plant Improvement* 1:67). Transformed plants are formed in the population of seeds generated by "dipped" plants. At a specific point during flower development, a pore exists in the ovary wall through which *Agrobacterium tumefaciens* gains access to the interior of the ovary. Once inside the ovary, the *Agrobacterium tumefaciens* proliferates and transforms individual ovules (Desfeux et al., 2000, *Plant Physiology,* 123:895). Transformed ovules follow the typical pathway of seed formation within the ovary.

*Agrobacterium*-Mediated Transient Expression

As indicated herein, in many embodiments of the present invention, systems for rapid (e.g., transient) expression of proteins or polypeptides in plants are desirable. Among other things, the present invention provides a powerful system for achieving such rapid expression in plants that utilizes an agrobacterial construct to deliver a viral expression system encoding the protein or polypeptide of interest. In some embodiments, any of the *Trypanosoma* antigens described herein can be expressed utilizing the launch vector technology, e.g., as described below. In some embodiments, launch vector constructs can also be utilized in the context of thermostable proteins, as described in more detail in the section entitled "*Trypanosoma Poplypeptide Fusions with Thermostable Proteins.*"

In some embodiments, according to the present invention, a "launch vector" is prepared that contains agrobacterial sequences including replication sequences and also contains plant viral sequences (including self-replication sequences) that carry a gene encoding the protein or polypeptide of interest. The launch vector is introduced into plant tissue, typically by agroinfiltration, which allows substantially systemic delivery. For transient transformation, non-integrated T-DNA copies of the launch vector remain transiently present in the nucleous and are transcribed leading to the expression of the carrying genes (Kapila et al., 1997). *Agrobacterium*-mediated transient expression, differently from viral vectors, cannot lead to the systemic spreading of the expression of the gene of interest. One advantage of this system is the possibility to clone genes larger than 2 kb to generate constructs that would be impossible to obtain with viral vectors (Voinnet et al., 2003). Furthermore, using such technique, it is possible to transform a plant with more than one transgene, such that multimeric proteins (e.g., antibodies subunits of complexed proteins) can be expressed and assembled. Furthermore, the possibility of co-expression of multiple transgenes by means of co-infiltration with different *Agrobacterium* can be taken advantage of, either by separate infiltration or using mixed cultures.

In certain embodiments, a launch vector includes sequences that allow for selection (or at least detection) in *Agrobacteria* and for selection/detection in infiltrated tissues. Furthermore, a launch vector typically includes sequences that are transcribed in a plant to yield viral RNA production, followed by generation of viral proteins. Furthermore, production of viral proteins and viral RNA yields rapid production of multiple copies of RNA encoding the pharmaceutically active protein of interest. Such production results in rapid protein production of the target of interest in a relatively short period of time. Thus, a highly efficient system for protein production can be generated.

The agroinfiltration technique utilizing viral expression vectors can be used to produce limited quantity of protein of interest in order to verify the expression levels before deciding if it is worth generating transgenic plants. Alternatively or additionally, the agroinfiltration technique utilizing viral expression vectors is useful for rapid generation of plants capable of producing huge amounts of protein as a primary production platform. Thus, this transient expression system can be used on industrial scale.

Further provided are any of a variety of different *Agrobacterial* plasmids, binary plasmids, or derivatives thereof such as pBIV, pBI1221, pGreen, etc., which can be used in these and other aspects of the invention. Numerous suitable vectors are known in the art and can be directed and/or modified according to methods known in the art, or those described herein so as to utilize in the methods described provided herein.

One particular exemplary launch vector is pBID4. This vector contains the 35S promoter of cauliflower mosaic virus (a DNA plant virus) that drives initial transcription of the recombinant viral genome following introduction into plants, and the nos terminator, the transcriptional terminator of *Agrobacterium* nopaline sunthase. The vector further contains sequences of the tobacco mosaic virus genome including genes for virus replication (126/183K) and cell-t-cell movement (MP). The vector further contains a gene encoding a polypeptide of interest, inserted into a unique cloning site within the tobacco mosaic virus genome sequences and under the transcriptional control of the coat protein subgenomic mRNA promoter. Because this "target gene" (i.e., gene encoding a protein or polypeptide of interest) replaces coding sequences for the TMV coat protein, the resultant viral vector is naked self-replicating RNA that is less subject to recombination than CP-containing vectors, and that cannot effectively spread and survive in the environment. Left and right border sequences (LB and RB) delimit the region of the launch vector that is transferred into plant cells following infiltration of plants with recombinant *Agrobacterium* carrying the vector. Upon introduction of *agrobacteria* carrying this vector into plant tissue (typically by agroinfiltration but alternatively by injection or other means), multiple single-stranded DNA (ssDNA) copies of sequence between LB and RB are generated and released in a matter of minutes. These introduced sequences are then amplified by viral replication. Translation of the target gene results in accumulation of large amounts of target protein or polypeptide in a short period of time.

In some embodiments of the invention, *Agrobacterium*-mediated transient expression produces up to about 5 g or more of target protein per kg of plant tissue. For example, in some embodiments, up to about 4, 3, 2, 1, or 0.5 g of target protein is produced per kg of plant tissue. In some embodiments, at least about 20-500 mg, or about 50-500 of target protein, or about 50-200, or about 50, 60, 70, 80, 90, 100, 110, 120, 130, 140, 150, 160, 170, 180, 190, or about 200, 250, 300, 350, 400, 450, 500, 550, 600, 650 700, 750, 800, 850, 900, 950, 1000, 1500, 1750, 2000, 2500, 3000 mg or more of protein per kg of plant tissue is produced.

In some embodiments of the invention, these expression levels are achieved within about 6, 5, 4, 3, or 2 weeks from infiltration. In some embodiments, these expression levels are achieved within about 10, 7, 5, 4, 3, 2 days, or even 1 day, from introduction of the expression construct. Thus, the time from introduction (e.g., infiltration) to harvest is typically less than about 2 weeks, 10 days, 1 week or less. Furthermore, one very attractive aspect of this embodiment of the invention is that it allows production of protein within about 8 weeks or less from the selection of amino acid sequence (even including time for "preliminary" expression studies). Also, each batch of protein can typically be produced within about 8 weeks, 6, weeks, 5 weeks, or less. Those of ordinary skill in the art will appreciate that these numbers may vary somewhat depending on the type of plant used. Most sprouts, including peas, will fall within the numbers given. *Nicotiana benthamiana*, however, may be grown longer, particularly prior to infiltration, as they are slower growing (from a much smaller seed). Other expected adjustments will be clear to those of ordinary skill in the art based on biology of the particular plants utilized. In some embodiments, certain pea varieties including for example, marrowfat pea, bill jump pea, yellow trapper pea, speckled pea, and green pea are particularly useful.

The inventors have also found that various *Nicotiana* plants are particularly useful in the practice of this aspect of the invention, including in particular *Nicotiana benthamiana*. In general, in the practice of this embodiment of the invention, *Nicotiana benthamiana* plants are grown for a time sufficient to allow development of an appropriate amount of biomass prior to infiltration (i.e., to delivery of *agrobacteria* containing the launch vector). Typically, plants are grown for a period of more than about 3 weeks, more typically more than about 4 weeks, or between about 5-6 weeks to accumulate biomass prior to infiltration.

The present inventors have further surprisingly found that, although both TMV and AlMV sequences can prove effective in such launch vector constructs, in some embodiments, AlMV sequences are particularly efficient at ensuring high level production of delivered protein or polypeptides.

Thus, in certain particular embodiments of the present invention, proteins or polypeptides of interest are produced in plants (e.g., *Nicotiana benthamiana*) from a launch vector that directs production of AlMV sequences carrying the gene of interest.

*Trypanosoma* Polypeptide Fusions with Thermostable Proteins

In certain aspects of the invention, provided are *Trypanosoma* antigen(s) comprising fusion polypeptides which comprise a *Trypanosoma* protein (or a fragment or variant thereof) operably linked to a thermostable protein (e.g., LicB, LicKM, etc., and described in further detail below). Inventive fusion polypeptides can be produced in any available expression system known in the art (including, but not limited to, launch vector technology). In certain embodiments, inventive fusion proteins are produced in a plant or portion thereof (e.g., plant, plant cell, root, sprout, etc.).

Enzymes or other proteins which are not found naturally in humans or animal cells are particularly appropriate for use in fusion polypeptides of the present invention. Thermostable proteins that, when fused, confer thermostability to a fusion product are useful. Thermostability allows produced protein to maintain conformation, and maintain produced protein at room temperature. This feature facilitates easy, time efficient and cost effective recovery of a fusion polypeptide. A representative family of thermostable enzymes useful in accordance with the invention is the glucanohydrolase family. These enzymes specifically cleave 1,4-β glucosidic bonds that are adjacent to 1,3-β linkages in mixed linked polysaccharides (Hahn et al., 1994 *Proc. Natl. Acad. Sci., USA*, 91:10417). Such enzymes are found in cereals, such as oat and barley, and are also found in a number of fungal and bacterial species, including *C. thermocellum* (Goldenkova et al., 2002, *Mol. Biol.* 36:698). Thus, desirable thermostable proteins for use in fusion polypeptides of the present invention include glycosidase enzymes. Exemplary thermostable glycosidase proteins include those represented by GenBank accession numbers selected from those set forth in Table 4, the contents of each of which are incorporated herein by reference by entire incorporation of the GenBank accession information for each referenced number. Exemplary thermostable enzymes of use in fusion proteins of the invention include *Clostridium thermocellum* P29716, *Brevibacillus brevis* P37073, and *Rhodthermus marinus* P45798, each of which are incorporated herein by reference to their GenBank accession numbers. Representative fusion proteins illustrated in the Examples utilize modified thermostable enzyme isolated from *Clostridium thermocellum*, however, any thermostable protein may be similarly utilized in accordance with the present invention.

TABLE 4

Thermostable Glycosidase Proteins

| | |
|---|---|
| P29716 | (Beta-glucanase *Clostridium thermocellum*) |
| P37073 | (Beta-glucanase *Brevibacillus brevis*) |
| 1MVE_A | (Beta-glucanase *Fibrobacter succinogenes*) |
| P07883 | (Extracellular agarase *Streptomyces coelicolor*) |
| P23903 | (Glucan endo-13-beta-glucosidase A1 *Bacillus circulans*) |
| P27051 | (Beta-glucanase *Bacillus licheniformis*) |
| P45797 | (Beta-glucanase *Paenibacillus polymyxa* (*Bacillus polymyxa*)) |
| P37073 | (Beta-glucanase *Brevibacillus brevis*) |
| P45798 | (Beta-glucanase *Rhodothermus marinus*) |
| P38645 | (Beta-glucosidase *Thermobispora bispora*) |
| P40942 | (Celloxylanase *Clostridium stercorarium*) |
| P14002 | (Beta-glucosidase *Clostridium thermocellum*) |
| O33830 | (Alpha-glucosidase *Thermotoga maritima*) |
| O43097 | (Xylanase *Thermomyces lanuginosus*) |
| P54583 | (Endo-glucanase E1 *Acidothermus cellulolyticus*) |
| P14288 | (Beta-galactosidase *Sulfolobus acidocaldarius*) |
| O52629 | (Beta-galactosidase *Pyrococcus woesei*) |
| P29094 | (Oligo-16-glucosidase *eobacillus thermoglucosidasius*) |
| P49067 | (Alpha-amylase *Pyrococcus furiosus*) |
| JC7532 | (Cellulase *Bacillus* species) |
| Q60037 | (Xylanase A *Thermotoga maritima*) |
| P33558 | (Xylanase A *Clostridium stercorarium*) |
| P05117 | (Polygalacturonase-2 precursor *Solanum lycopersicum*) |
| P04954 | (Cellulase D *Clostridium thermocellum*) |
| Q4J929 | (N-glycosylase *Sulfolobus acidocaldarius*) |
| O33833 | (Beta-fructosidase *Thermotoga maritima*) |
| P49425 | (Endo-14-beta-mannosidase *Rhodothermus marinus*) |
| P06279 | (Alpha-amylase *Geobacillus stearothermophilus*) |
| P45702 P45703 P40943 | (Xylanase *Geobacillus stearothermophilus*) |
| P09961 | (Alpha-amylase 1 *Dictyoglomus thermophilum*) |
| Q60042 | (Xylanase A *Thermotoga neapolitana*) |
| AAN05438 AAN05439 | (Beta-glycosidase *Thermus thermophilus*) |
| AAN05437 | (Sugar permease *Thermus thermophilus*) |
| AAN05440 | (Beta-glycosidase *Thermus filiformis*) |
| AAD43138 | (Beta-glycosidase *Thermosphaera aggregans*) |

When designing fusion proteins and polypeptides in accordance with the invention, it is desirable, of course, to preserve immunogenicity of the antigen. Still further, it is desirable in certain aspects of the invention to provide constructs which provide thermostability of a fusion protein. This feature facilitates easy, time efficient and cost effective recovery of a target antigen. In certain aspects, antigen fusion partners may be selected which provide additional advantages, including enhancement of immunogenicity, potential to incorporate multiple vaccine determinants, yet lack prior immunogenic exposure to vaccination subjects. Further beneficial qualities of fusion peptides of interest include proteins which provide ease of manipulation for incorporation of one or more antigens, as well as proteins which have potential to confer ease of production, purification, and/or formulation for vaccine preparations. One of ordinary skill in the art will appreciate that three dimensional presentation can affect each of these beneficial characteristics. Preservation of immunity or preferential qualities therefore may affect, for example, choice of fusion partner and/or choice of fusion location (e.g., N-terminus, C-terminus, internal, combinations thereof). Alternatively or additionally, preferences may affects length of segment selected for fusion, whether it be length of antigen, or length of fusion partner selected.

The present inventors have demonstrated successful fusion of a variety of antigens with a thermostable protein. For example, the present inventors have used the thermostable carrier molecule LicB, also referred to as lichenase, for production of fusion proteins. LicB is 1,3-1, 4-β glucanase (LicB) from *Clostridium thermocellum* (GenBank accession: X63355 [gi:40697]). LicB belongs to a family of globular proteins. Based on the three dimensional structure of LicB, its N- and C-termini are situated close to each other on the surface, in close proximity to the active domain. LicB also has a loop structure exposed on the surface that is located far from the active domain. We have generated constructs such that the loop structure and N- and C-termini of protein can be used as insertion sites for *Trypanosoma* antigen polypeptides. *Trypanosoma* antigen polypeptides can be expressed as N- or C-terminal fusions or as inserts into the surface loop. Importantly, LicB maintains its enzymatic activity at low pH and at high temperature (up to 75° C.). Thus, use of LicB as a carrier molecule contributes advantages, including likely enhancement of target specific immunogenicity, potential to incorporate multiple vaccine determinants, and straightforward formulation of vaccines that may be delivered nasally, orally or parenterally. Furthermore, production of LicB fusions in plants should reduce the risk of contamination with animal or human pathogens. See examples provided herein.

Fusion proteins of the invention comprising *Trypanosoma* antigen may be produced in any of a variety of expression systems, including both in vitro and in vivo systems. One skilled in the art will readily appreciate that optimization of nucleic acid sequences for a particular expression system is often desirable. For example, in the exemplification provided herein, optimized sequence for expression of *Trypanosoma* antigen-LicKM fusions in plants is provided (see Example 1). Thus, any relevant nucleic acid encoding *Trypanosoma* antigen(s) fusion protein(s) and fragments thereof in accordance with the invention is intended to be encompassed within nucleic acid constructs of the invention.

For production in plant systems, transgenic plants expressing *Trypanosoma* antigen(s) (e.g., *Trypanosoma* protein(s) or fragments or fusions thereof) may be utilized. Alternatively or additionally, transgenic plants may be produced using methods well known in the art to generate stable production crops. Additionally, plants utilizing transient expression systems may be utilized for production of *Trypanosoma* antigen(s). When utilizing plant expression systems, whether transgenic or transient expression in plants is utilized, any of nuclear expression, chloroplast expression, mitochondrial expression, or viral expression may be taken advantage of according to the applicability of the system to antigen desired. Furthermore, additional expression systems for production of antigens and fusion proteins in accordance with the present invention may be utilized. For example, mammalian expression systems (e.g., mammalian cell lines (e.g., CHO, etc.)), bacterial expression systems (e.g., *E. coli*), insect expression systems (e.g., baculovirus), yeast expression systems, and in vitro expression systems (e.g., reticulate lysates) may be used for expression of antigens and fusion proteins of the invention.

Production and Isolation of Antigen

In general, standard methods known in the art may be used for culturing or growing plants, plant cells, and/or plant tissues of the invention (e.g., clonal plants, clonal plant cells, clonal roots, clonal root lines, sprouts, sprouted seedlings, plants, etc.) for production of antigen(s). A wide variety of culture media and bioreactors have been employed to culture hairy root cells, root cell lines, and plant cells (see, for example, Giri et al., 2000, *Biotechnol. Adv.*, 18: 1; Rao et al., 2002, *Biotechnol. Adv.*, 20: 101; and references in both of the foregoing, all of which are incorporated herein by reference). Clonal plants may be grown in any suitable manner.

In a certain embodiments, *Trypanosoma* antigens of the invention may be produced by any known method. In some embodiments, a *Trypanosoma* antigen is expressed in a plant or portion thereof. Proteins are isolated and purified in accordance with conventional conditions and techniques known in the art. These include methods such as extraction, precipitation, chromatography, affinity chromatography, electrophoresis, and the like. The present invention involves purification and affordable scaling up of production of *Trypanosoma* antigen(s) using any of a variety of plant expression systems known in the art and provided herein, including viral plant expression systems described herein.

In many embodiments of the present invention, it will be desirable to isolate *Trypanosoma* antigen(s) for vaccine products. Where a protein of the invention is produced from plant tissue(s) or a portion thereof, e.g., roots, root cells, plants, plant cells, that express them, methods described in further detail herein, or any applicable methods known in the art may be used for any of partial or complete isolation from plant material. Where it is desirable to isolate the expression product from some or all of plant cells or tissues that express it, any available purification techniques may be employed. Those of ordinary skill in the art are familiar with a wide range of fractionation and separation procedures (see, for example, Scopes et al., Protein Purification Principles and Practice, 3$^{rd}$ Ed., Janson et al., 1993; *Protein Purification: Principles, High Resolution Methods, and Applications*, Wiley-VCH, 1998; Springer-Verlag, NY, 1993; and Roe, *Protein Purification Techniques*, Oxford University Press, 2001; each of which is incorporated herein by reference). Often, it will be desirable to render the product more than about 50%, 60%, 70%, 80%, 85%, 90%, 91%, 92%, 93%, 94%, 95%, 96%, 97%, 98%, or 99% pure. See, e.g., U.S. Pat. Nos. 6,740,740 and 6,841,659 (each of which is incorporated herein by reference) for discussion of certain methods useful for purifying substances from plant tissues or fluids.

Those skilled in the art will appreciate that a method of obtaining desired *Trypanosoma* antigen(s) product(s) is by extraction. Plant material (e.g., roots, leaves, etc.) may be extracted to remove desired products from residual biomass, thereby increasing the concentration and purity of product. Plants may be extracted in a buffered solution. For example, plant material may be transferred into an amount of ice-cold water at a ratio of one to one by weight that has been buffered with, e.g., phosphate buffer. Protease inhibitors can be added as required. The plant material can be disrupted by vigorous blending or grinding while suspended in buffer solution and extracted biomass removed by filtration or centrifugation. The product carried in solution can be further purified by additional steps or converted to a dry powder by freeze-drying or precipitation. Extraction can be carried out by pressing. Plants or roots can be extracted by pressing in a press or by being crushed as they are passed through closely spaced rollers. Fluids expressed from crushed plants or roots are collected and processed according to methods well known in the art. Extraction by pressing allows release of products in a more concentrated form. However, overall yield of product may be lower than if product were extracted in solution.

Vaccines

The present invention provides pharmaceutical antigen proteins for therapeutic use, such as *Trypanosoma* (e.g. *T. brucei*) antigen(s) (e.g., *Trypanosoma* protein(s) or an immunogenic portion(s) thereof, or fusion proteins comprising *Trypanosoma* protein(s) or an immunogenic portion(s) thereof) active as a vaccine for therapeutic and/or prophylactic treatment of *Trypanosoma* infection. Further, the invention provides veterinary use, as such *Trypanosoma* antigen is active in veterinary applications. In certain embodiments, *Trypanosoma* antigen(s) may be produced by plant(s) or portion thereof (e.g., root, cell, sprout, cell line, plant, etc.) of the invention. In certain embodiments, provided *Trypanosoma* antigens are expressed in plants, plant cells, and/or plant tissues (e.g., sprouts, sprouted seedlings, roots, root culture, clonal cells, clonal cell lines, clonal plants, etc.), and can be used directly from plant or partially purified or purified in preparation for pharmaceutical administration to a subject.

The present invention provides plants, plant cells, and plant tissues expressing *Trypanosoma* antigen(s) that maintains pharmaceutical activity when administered to a subject in need thereof. Exemplary subjects include vertebrates (e.g., mammals such as humans). According to the present invention, subjects include veterinary subjects such as bovines, ovines, canines, felines, etc. In certain aspects, an edible plant or portion thereof (e.g., sprout, root) is administered orally to a subject in a therapeutically effective amount. In some aspects one or more *Trypanosoma* antigen(s) is provided in a pharmaceutical preparation, as described herein.

Vaccine compositions of the invention comprise one or more *Trypanosoma* antigens. In certain embodiments, at least two *Trypanosoma* antigens of the invention are included in an administered vaccine composition.

According to the present invention, treatment of a subject with a *Trypanosoma* antigen vaccine is intended to elicit a physiological effect. A vaccine protein may have healing curative or palliative properties against a disorder or disease and can be administered to ameliorate relieve, alleviate, delay onset of, reverse or lessen symptoms or severity of a disease or disorder. A vaccine comprising a *Trypanosoma* antigen may have prophylactic properties and can be used to prevent or delay the onset of a disease or to lessen the severity of such disease, disorder, or pathological condition when it does emerge. A physiological effect elicited by treatment of a subject with antigen according to the present invention can include an effective immune response such that infection by an organism is thwarted.

In some embodiments, inventive vaccines are delivered by oral and/or mucosal routes. Oral and/or mucosal delivery has the potential to prevent infection of mucosal tissues, the primary gateway of infection for many pathogens. Oral and/or mucosal delivery can prime systemic immune response. There has been considerable progress in the development of heterologous expression systems for oral administration of antigens that stimulate the mucosal-immune system and can prime systemic immunity. Previous efforts at delivery of oral vaccine however, have demonstrated a requirement for considerable quantities of antigen in achieving efficacy. Thus, economical production of large quantities of target antigens is a prerequisite for creation of effective oral vaccines. The development of plants expressing antigens, including thermostable antigens, represents a more realistic approach to such difficulties.

The pharmaceutical preparations of the present invention can be administered in a wide variety of ways to a subject, such as, for example, orally, nasally, enterally, parenterally, intramuscularly or intravenously, rectally, vaginally, topically, ocularly, pulmonarily, or by contact application. In certain embodiments, a *Trypanosoma* antigen expressed in a plant or portion thereof is administered to a subject orally by direct administration of a plant to a subject. In some aspects a vaccine protein expressed in a plant or portion thereof is extracted and/or purified, and used for the preparation of a pharmaceutical composition. It may be desirable to formulate such isolated products for their intended use (e.g., as a pharmaceutical agent, vaccine composition, etc.). In some embodiments, it will be desirable to formulate products together with some or all of plant tissues that express them.

Where it is desirable to formulate product together with the plant material, it will often be desirable to have utilized a plant that is not toxic to the relevant recipient (e.g., a human or other animal). Relevant plant tissue (e.g., cells, roots, leaves) may simply be harvested and processed according to techniques known in the art, with due consideration to maintaining activity of the expressed product. In certain embodiments of the invention, it is desirable to have expressed *Trypanosoma* antigen in an edible plant (and, specifically in edible portions of the plant) so that the material can subsequently be eaten. For instance, where vaccine antigen is active after oral delivery (when properly formulated), it may be desirable to produce antigen protein in an edible plant portion, and to formulate expressed *Trypanosoma* antigen for oral delivery together with some or all of the plant material with which the protein was expressed.

Vaccine antigens (i.e., *Trypanosoma* antigens of the invention) provided may be formulated according to known techniques. For example, an effective amount of a vaccine product can be formulated together with one or more organic or inorganic, liquid or solid, pharmaceutically suitable carrier materials. A vaccine antigen produced according to the present invention may be employed in dosage forms such as tablets, capsules, troches, dispersions, suspensions, solutions, gelcaps, pills, caplets, creams, ointments, aerosols, powder packets, liquid solutions, solvents, diluents, surface active agents, isotonic agents, thickening or emulsifying agents, preservatives, and solid bindings, as long as the biological activity of the protein is not destroyed by such dosage form.

In general, compositions may comprise any of a variety of different pharmaceutically acceptable carrier(s), adjuvant(s), or vehicle(s), or a combination of one or more such carrier(s), adjuvant(s), or vehicle(s). As used herein the language "pharmaceutically acceptable carrier, adjuvant, or vehicle" includes solvents, dispersion media, coatings, antibacterial and antifungal agents, isotonic and absorption delaying agents, and the like, compatible with pharmaceutical administration. Materials that can serve as pharmaceutically acceptable carriers include, but are not limited to sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening agents, flavoring agents, and perfuming agents, preservatives, and antioxidants can be present in the composition, according to the judgment of the formulator (see also *Remington's Pharmaceutical Sciences*, Fifteenth Edition, E. W. Martin, Mack Publishing Co., Easton, Pa., 1975). For example, vaccine antigen product may be provided as a pharmaceutical composition by means of conventional mixing granulating dragee-making, dissolving, lyophilizing, or similar processes.

Additional Vaccine Components

Inventive vaccines may include additionally any suitable adjuvant to enhance the immunogenicity of the vaccine when administered to a subject. For example, such adjuvant(s) may include, without limitation, extracts of *Quillaja saponaria* (QS), including purified subfractions of food grade QS such as Quil A and QS-21, alum, aluminum hydroxide, aluminum phosphate, MF59, Malp2, incomplete Freund's adjuvant; complete freund's adjuvant, alhydrogel, 3 De-O-acylated monophosphoryl lipid A (3D-MPL). Further adjuvants include immunomodulatory oligonucleotides, for example unmethylated CpG sequences as disclosed in WO 96/02555. Combinations of different adjuvants, such as those mentioned hereinabove, are contemplated as providing an adjuvant which is a preferential stimulator of TH1 cell response. For example, QS21 can be formulated together with 3D-MPL. The ratio of QS21:3 D-MPL will typically be in the order of 1:10 to 10:1; 1:5 to 5:1; and often substantially 1:1. The desired range for optimal synergy may be 2.5:1 to 1:1 3D-MPL: QS21. Doses of purified QS extracts suitable for use in a human vaccine formulation are from 0.01 mg to 10 mg per kilogram of bodyweight.

It should be noted that certain thermostable proteins (e.g., lichenase) may themselves demonstrate immunoresponse potentiating activity, such that use of such protein whether in a fusion with a *Trypanosoma* antigen or separately may be considered use of an adjuvant. Thus, inventive vaccine compositions may further comprise one or more adjuvants. Certain vaccine compositions may comprise two or more adjuvants. Furthermore, depending on formulation and routes of administration, certain adjuvants may be desired in particular formulations and/or combinations.

In certain situations, it may be desirable to prolong the effect of an inventive vaccine by slowing the absorption of one or more components of the vaccine product (e.g., protein) that is subcutaneously or intramuscularly injected. This may be accomplished by use of a liquid suspension of crystalline or amorphous material with poor water solubility. The rate of absorption of product then depends upon its rate of dissolution, which in turn, may depend upon size and form. Alternatively or additionally, delayed absorption of a parenterally administered product is accomplished by dissolving or suspending the product in an oil vehicle. Injectable depot forms are made by forming microcapsule matrices of protein in biodegradable polymers such as polylactide-polyglycolide. Depending upon the ratio of product to polymer and the nature of the particular polymer employed, rate of release can be controlled. Examples of biodegradable polymers include poly(orthoesters) and poly(anhydrides). Depot injectable formulations may be prepared by entrapping product in liposomes or microemulsions, which are compatible with body tissues. Alternative polymeric delivery vehicles can be used for oral formulations. For example, biodegradable, biocompatible polymers such as ethylene vinyl acetate, polyanhydrides, polyglycolic acid, collagen, polyorthoesters, and polylactic acid, etc., can be used. Antigen(s) or an immunogenic portions thereof may be formulated as microparticles, e.g., in combination with a polymeric delivery vehicle.

Enterally administered preparations of vaccine antigens may be introduced in solid, semi-solid, suspension or emulsion form and may be compounded with any pharmaceutically acceptable carriers, such as water, suspending agents, and emulsifying agents. Antigens may be administered by means of pumps or sustained-release forms, especially when administered as a preventive measure, so as to prevent the development of disease in a subject or to ameliorate or delay an already established disease. Supplementary active compounds, e.g., compounds independently active against the disease or clinical condition to be treated, or compounds that enhance activity of an inventive compound, can be incorporated into or administered with compositions. Flavorants and coloring agents can be used.

Inventive vaccine products, optionally together with plant tissue, are particularly well suited for oral administration as pharmaceutical compositions. Oral liquid formulations can be used and may be of particular utility for pediatric populations. Harvested plant material may be processed in any of a variety of ways (e.g., air drying, freeze drying, extraction etc.), depending on the properties of the desired therapeutic product and its desired form. Such compositions as described above may be ingested orally alone or ingested together with food or feed or a beverage. Compositions for oral administration include plants; extractions of plants, and proteins purified from infected plants provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any plant biomass that has been dried, for example, freeze dried, air dried, or spray dried. For example, plants may be air dried by placing them in a commercial air dryer at about 120 degrees Fahrenheit until biomass contains less than 5% moisture by weight. The dried plants may be stored for further processing as bulk solids or further processed by grinding to a desired mesh sized powder. Alternatively or additionally, freeze-drying may be used for products that are sensitive to air-drying. Products may be freeze dried by placing them into a vacuum drier and dried frozen under a vacuum until the biomass contains less than about 5% moisture by weight. Dried material can be further processed as described herein.

Plant-derived material may be administered as or together with one or more herbal preparations. Useful herbal preparations include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, liquid dosage, etc. Those skilled in the art will appreciate the various formulations and modalities of delivery of herbal preparations that may be applied to the present invention.

Inventive root lines, cell lines, plants, extractions, powders, dried preparations and purified protein or nucleic acid products, etc., can be in encapsulated form with or without one or more excipients as noted above. Solid dosage forms such as tablets, dragees, capsules, pills, and granules can be prepared with coatings and shells such as enteric coatings, release controlling coatings and other coatings well known in the pharmaceutical formulating art. In such solid dosage forms active agent may be mixed with at least one inert diluent such as sucrose, lactose or starch. Such dosage forms may comprise, as is normal practice, additional substances other than inert diluents, e.g., tableting lubricants and other tableting aids such as magnesium stearate and microcrystalline cellulose. In the case of capsules, tablets and pills, the dosage forms may comprise buffering agents. They may optionally contain opacifying agents and can be of a composition that they release the active ingredient(s) only, or preferentially, in a certain part of the intestinal tract, and/or in a delayed manner. Examples of embedding compositions that can be used include polymeric substances and waxes.

In some methods, a plant or portion thereof expressing a *Trypanosoma* antigen according to the present invention, or biomass thereof, is administered orally as medicinal food. Such edible compositions are typically consumed by eating raw, if in a solid form, or by drinking, if in liquid form. The plant material can be directly ingested without a prior processing step or after minimal culinary preparation. For example, the vaccine protein may be expressed in a sprout which can be eaten directly. For instance, vaccine antigens expressed in an alfalfa sprout, mung bean sprout, or spinach or lettuce leaf sprout, etc. In one embodiment, plant biomass may be processed and the material recovered after the processing step is ingested.

Processing methods useful in accordance with the present invention are methods commonly used in the food or feed industry. The final products of such methods typically include a substantial amount of an expressed antigen and can be conveniently eaten or drunk. The final product may be mixed with other food or feed forms, such as salts, carriers, favor enhancers, antibiotics, and the like, and consumed in solid, semi-solid, suspension, emulsion, or liquid form. Such methods can include a conservation step, such as, e.g., pasteurization, cooking, or addition of conservation and preservation agents. Any plant may be used and processed in the present invention to produce edible or drinkable plant matter. The amount of *Trypanosoma* antigen in a plant-derived preparation may be tested by methods standard in the art, e.g., gel electrophoresis, ELISA, or Western blot analysis, using a probe or antibody specific for product. This determination may be used to standardize the amount of vaccine antigen protein ingested. For example, the amount of vaccine antigen may be determined and regulated, for example, by mixing batches of product having different levels of product so that the quantity of material to be drunk or eaten to ingest a single dose can be standardized. The contained, regulatable environment of the present invention, however, should minimize the need to carry out such standardization procedures.

A vaccine protein produced in a plant cell or tissue and eaten by a subject may be preferably absorbed by the digestive system. One advantage of the ingestion of plant tissue that has been only minimally processed is to provide encapsulation or sequestration of the protein in cells of the plant. Thus, product may receive at least some protection from digestion in the upper digestive tract before reaching the gut or intestine and a higher proportion of active product would be available for uptake.

Pharmaceutical compositions of the present invention can be administered therapeutically or prophylactically. The compositions may be used to treat or prevent a disease. For example, any individual who suffers from a disease or who is at risk of developing a disease may be treated. It will be appreciated that an individual can be considered at risk for developing a disease without having been diagnosed with any symptoms of the disease. For example, if the individual is known to have been, or to be intended to be, in situations with relatively high risk of exposure to *Trypanosoma* infection, that individual will be considered at risk for developing the disease. Similarly, if members of an individual's family or friends have been diagnosed with *Trypanosoma* infection, the individual may be considered to be at risk for developing the disease.

Liquid dosage forms for oral administration include, but are not limited to, pharmaceutically acceptable emulsions, microemulsions, solutions, suspensions, syrups, and elixirs. In addition to active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents.

Compositions for rectal or vaginal administration may be suppositories or retention enemas, which can be prepared by mixing the compositions of this invention with suitable non-irritating excipients or carriers such as cocoa butter, polyethylene glycol or a suppository wax which are solid at ambient temperature but liquid at body temperature and therefore melt in the rectum or vaginal cavity and release the active protein.

Dosage forms for topical, transmucosal or transdermal administration of a vaccine composition of this invention include ointments, pastes, creams, lotions, gels, powders, solutions, sprays, inhalants or patches. The active agent, or preparation thereof, is admixed under sterile conditions with a pharmaceutically acceptable carrier and any needed preservatives or buffers as may be required. For transmucosal or transdermal administration, penetrants appropriate to the barrier to be permeated may be used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, antigen or a immunogenic portion thereof may be formulated into ointments, salves, gels, or creams as generally known in the art. Ophthalmic formulation, eardrops, and eye drops are contemplated as being within the scope of this invention. Additionally, the present invention contemplates the use of transdermal patches, which have the added advantage of providing controlled delivery of a vaccine protein to the body. Such dosage forms can be made by suspending or dispensing the vaccine product in the proper medium. Absorption enhancers can be used to increase the flux of the vaccine protein across the skin. The rate can be controlled by either providing a rate controlling membrane or by dispersing the vaccine protein in a polymer matrix or gel.

Inventive compositions are administered in such amounts and for such time as is necessary to achieve the desired result. In certain embodiments of the present invention a "therapeutically effective amount" of a pharmaceutical composition is that amount effective for treating, attenuating, or preventing a disease in a subject. Thus, the "amount effective to treat, attenuate, or prevent disease," as used herein, refers to a nontoxic but sufficient amount of the pharmaceutical composition to treat, attenuate, or prevent disease in any subject. For example, the "therapeutically effective amount" can be an amount to treat, attenuate, or prevent infection (e.g., viral infection, *Trypanosoma* infection), etc.

The exact amount required may vary from subject to subject, depending on the species, age, and general condition of the subject, the stage of the disease, the particular pharmaceutical mixture, its mode of administration, and the like. *Trypanosoma* antigens of the invention, including plants expressing antigen(s) and/or preparations thereof may be formulated in dosage unit form for ease of administration and uniformity of dosage. The expression "dosage unit form," as used herein, refers to a physically discrete unit of vaccine composition appropriate for the patient to be treated. It will be understood, however, that the total daily usage of the compositions of the present invention is typically decided by an attending physician within the scope of sound medical judgment. The specific therapeutically effective dose level for any particular patient or organism may depend upon a variety of factors including the severity or risk of infection; the activity of the specific compound employed; the specific composition employed; the age, body weight, general health, sex of the patient, diet of the patient, pharmacokinetic condition of the patient, the time of administration, route of administration, and rate of excretion of the specific antigen(s) employed; the duration of the treatment; drugs used in combination or coincidental with the vaccine composition employed; and like factors well known in the medical arts.

It will be appreciated that vaccine compositions of the present invention can be employed in combination therapies (e.g., combination vaccine therapies), that is, pharmaceutical compositions can be administered concurrently with, prior to, or subsequent to, one or more other desired pharmaceutical and/or vaccination procedures. The particular combination of therapies (e.g., vaccines, therapeutic treatment of *Trypanosoma* infection) to employ in a combination regimen will generally take into account compatibility of the desired therapeutics and/or procedures and the desired therapeutic effect to be achieved. It will be appreciated that the therapies and/or vaccines employed may achieve a desired effect for the same disorder (for example, an inventive antigen may be administered concurrently with another *Trypanosoma* vaccine), or they may achieve different effects.

In certain embodiments, vaccine compositions comprise at least two *Trypanosoma* antigens. For example, certain vaccine compositions can comprise at least two *Trypanosoma* antigens of the invention (e.g., a HA domain and an NA domain containing antigen of the invention). In some aspects such combination vaccines may include one thermostable fusion protein comprising *Trypanosoma* antigen; in some aspects, two or more thermostable fusion proteins comprising *Trypanosoma* antigen are provided.

Where combination vaccines are utilized, it will be understood that any combination of *Trypanosoma* antigens may be used for such combinations. Compositions may include multiple *Trypanosoma* antigens, including multiple antigens provided herein. Furthermore, compositions may include one or more antigens provided herein with one or more additional antigens. Combinations of *Trypanosoma* antigens include *Trypanosoma* antigens derived from one or more various subtypes or strains such that immunization confers immune response against more than one infection type. Combinations of *Trypanosoma* antigen may include at least one, at least two, at least three, at least four or more antigens derived from different subtypes or strains. In some combinations, at least two or at least three antigens from different subtypes are combined in one vaccine composition. Furthermore, combination vaccines may utilize *Trypanosoma* antigen and antigen from one or more unique infectious agents.

Kits

In some embodiments, the present invention provides pharmaceutical packs or kits including *Trypanosoma* (e.g. *T. brucei*) antigens according to the present invention. In certain embodiments, pharmaceutical packs or kits include live sprouted seedlings, clonal entity or plant producing a *Trypanosoma* antigen according to the present invention, or preparations, extracts, or pharmaceutical compositions containing vaccine in one or more containers filled with optionally one or more additional ingredients of pharmaceutical compositions of the invention. In some embodiments, pharmaceutical packs or kits include pharmaceutical compositions comprising purified *Trypanosoma* antigen according to the present invention, in one or more containers optionally filled with one or more additional ingredients of pharmaceutical compositions of the invention. In certain embodiments, the pharmaceutical pack or kit includes an additional approved therapeutic agent (e.g., *Trypanosoma* antigen, *Trypanosoma* vaccine) for use as a combination therapy. Optionally associated with such container(s) can be a notice in the form prescribed by a governmental agency regulating the manufacture, use or sale of pharmaceutical products, which notice reflects approval by the agency of manufacture, use, or sale for human administration.

Kits are provided that include therapeutic reagents. As but one non-limiting example, *Trypanosoma* vaccine can be provided as oral formulations and administered as therapy. Alternatively or additionally, *Trypanosoma* vaccine can be provided in an injectable formulation for administration. In some embodiments, *Trypanosoma* vaccine can be provided in an inhalable formulation for administration. Pharmaceutical doses or instructions therefor may be provided in the kit for administration to an individual suffering from or at risk for *Trypanosoma* infection.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain information, exemplification and guidance, which can be adapted to the practice of this invention in its various embodiments and the equivalents thereof.

EXEMPLIFICATION

Example 1

Generation of Vaccine Candidate Constructs

Generation of AlMV Coat Protein (CP) Fusions to Antigen Sequences from *T. brucei* Alpha Tubulin, Beta Tubulin, and MAP15

DNA sequences of target peptides were synthesized and cloned as in-frame N-terminal fusions with Alfalfa mosaic virus coat protein (AlMV CP), which is expressed by the AlMV-based RNA3 vector. The AlMV-based RNA 3 vector requires the replicase proteins P1 and P2 for replication of RNA3. Recombinant AlMV CP is expressed from RNA3 via subgenomic messenger RNA4. During multiplication of the AlMV system in tobacco plants, the recombinant AlMV CP assembles into virions that display multiple copies of the target peptide on their surfaces (FIG. 2).

A non-template-based PCR approach was taken to engineer the alpha tubulin, beta tubulin, and MAP15 peptides. DNA fragments encoding each target peptide were synthesized using primers containing 16-20 complementary nucleotides that served as templates for each other. The 5' primers included the KpnI restriction enzyme recognition site followed by the ATG start codon and the codon for amino acid serine, while the 3' primers for each construct contained a SalI restriction enzyme recognition site. The PCR products were cloned as KpnI-SalI fragments into a cDNA clone of AlMV RNA3-based transient expression vector, so that the resulting peptide sequence was in-frame with the AlMV CP amino acid sequence (SEQ ID NO. 28; KpnI and SalI restriction sites are boldfaced and underlined):

<u>GGTACC</u>ATGAGT<u>GTCGAC</u>AGTTCTTCACAAAAGAAAGCTGGTGGGAAAG

CTGGTAAACCTACTAAACGTTCTCAGAACTATGCTGCCTTACGCAAAGCT

CAACTGCCGAAGCCTCCGGCGTTGAAAGTCCCGGTTGTAAAACCGACGAA

TACTATACTGCCACAGACGGGCTGCGTGTGGCAAAGCCTCGGGACCCCTC

TGAGTCTGAGCTCTTTTAATGGGCTCGGCGTGAGATTCCTCTACAGTTTT

CTGAAGGATTTCGCGGGACCTCGGATCCTCGAAGAGGATCTGATTTACAG

GATGGTGTTTTCCATAACACCGTCCTATGCCGGCACCTTTTGTCTCACTG

ATGACGTGACGACTGAGGATGGTAGGGCCGTTGCGCATGGTAATCCCATG

CAAGAATTTCCTCATGGCGCGTTTCACGCTAATGAGAAGTTCGGGTTTGA

GTTGGTCTTCACAGCTCCTACCCATGCGGGAATGCAAAACCAAAATTTCA

AGCATTCCTATGCCGTAGCCCTCTGTCTGGACTTCGACGCGCAGCCTGAG

GGATCTAAAAATCCCTCATACCGATTCAACGAAGTTTGGGTCGAGAGAAA

GGCGTTCCCGCGAGCAGGGCCCCTCCGCAGTTTGATTACTGTGGGGCTGC

TCGACGAAGCTGACGATCTTGATCGTCATTGA

In particular, nucleotide sequences encoding eight target peptides from alpha tubulin that were not fully homologous with sequences from *H. sapiens* and *B. taurus* (shown in Table 1); nucleotide sequences encoding eleven target peptides from beta tubulin that were not fully homologous with sequences from *H. sapiens* and *B. taurus* (shown in Table 2); and nucleotide sequences encoding five target peptides from MAP15 representing two or more repetitive motifs (shown in Table 3) were all produced according to this method.

Generation of Thermostable Carrier Constructs

Alpha tubulin polytopes and beta tubulin polytopes were generated by joining multiple peptides together in a single construct. Specifically, the sequences shown in Table 1 were joined together to generate the alpha tubulin polytope ("Atub"), and the sequences shown in Table 2 were joined together to generate the beta tubulin polytope ("Btub"). The sequences shown in Table 3 could be joined together to generate a MAP15 polytope ("MAP15"). These polytopes can be used for multiple purposes. For example, the polytopes can be used to immunize rabbits to obtain sera that is useful for characterization of recombinant particles containing individual peptides. Alternatively or additionally, they can be produced in *E. coli*, purified, and used in ELISA assays to screen for antibodies that recognize the multiple antigens contained within the polytopes. Finally, the polytopes can be engineered as fusions with a thermostable carrier protein (e.g. lichenase), as described in the following paragraphs.

Full length native *C. thermocellum* lichenase, LicB, consists sequentially of a leader peptide (Lp), an N-terminal portion (A), a surface loop (1), a C-terminal portion (C), a Pro-Thr box, and a cellulosome-binding domain (C-BD). The Lp, Pro-Thr box and C-BD encoding sequences were removed from the LicB encoding gene, circularly permutated the molecule to invert the N- and C-termini (Musiychuk et al., 2007, *Influenza and Other Respiratory Viruses*, 1:1), and incorporated unique restriction endonuclease sites for cloning target sequences at the N- and C-termini as well as into the surface loop (1). The resulting engineered carrier molecule sequence was verified, and is designated LicKM:

SEQ ID NO.: 29:
GGATCCTTAATTAAAATGGGAGGTTCTTATCCATATAAGTCTGGTGAGTA

TAGAACTAAGTCTTTCTTTGGATATGGTTATTATGAAGTTAGGATGAAGG

CTGCAAAGAACGTTGGAATTGTTTCTTCTTTCTTTACTTATACTGGACCA

TCTGATAACAACCCATGGGATGAGATTGATATTGAGTTTCTTGGAAAGGA

TACTACTAAGGTTCAATTCAACTGGTATAAGAATGGTGTTGGTGGAAACG

AGTATCTTCATAACCTTGGATTTGATGCTTCTCAAGATTTTCATACTTAT

GGTTTTGAGTGGAGACCAGATTATATTGATTTTTATGTTGATGGAAAGAA

GGTTTATAGAGGTACTAGAAACATTCCAGTTACTCCTGGAAAGATTATGA

TGAATCTTTGGCCAGGAATTGGTGTTGATGAATGGCTTGGTAGATATGAT

GGAAGAACTCCACTTCAAGCTGAGTATGAGTATGTTAAGTATTATCCAAA

CGGTAGATCTGAATTCAAGCTTGTTGTTAATACTCCATTTGTTGCTGTTT

TCTCTAACTTTGATTCTTCTCAATGGGAAAAGGCTGATTGGGCTAACGGT

TCTGTTTTTAACTGTGTTTGGAAGCCATCTCAAGTTACTTTTTCTAACGG

AAAGATGATTCTTACTTTGGATAGAGAGTATGTCGACCATCATCATCATC

ATCATTGACTCGAGCTC

SEQ ID NO.: 30
(Histidine tag is boldfaced and underlined):
MGGSYPYKSGEYRTKSFFGYGYYEVRMKAAKNVGIVSSFFTYTGPSDNNP

WDEIDIEFLGKDTTKVQFNWYKNGVGGNEYLHNLGFDASQDFHTYGFEWR

PDYIDFYVDGKKVYRGTRNIPVTPGKIMMNLWPGIGVDEWLGRYDGRTPL

QAEYEYVKYYPNGRSEFKLVVNTPFVAVFSNFDSSQWEKADWANGSVFNC

VWKPSQVTFSNGKMILTLDREYVDHHHHHH

For certain constructs, a signal peptide (e.g., PR-1A; "Pathogen-Related protein 1 A") and an endoplasmic reticulum retention sequence (e.g., KDEL sequence) were engineered at the N- and C-termini, respectively, of LicKM. The nucleic acid and amino acid sequences of these constructs are shown in SEQ ID NO.: 31 and SEQ ID NO.: 32:

SEQ ID NO.: 31:
GGATCCTTAATTAAAATGGGATTTGTTCTCTTTTCACAATTGCCTTCATT

TCTTCTTGTCTCTACACTTCTCTTATTCCTAGTAATATCCCACTCTTGCC

GTGCCCAAAATGGAGGTTCTTATCCATATAAGTCTGGTGAGTATAGAACT

AAGTCTTTCTTTGGATATGGTTATTATGAAGTTAGGATGAAGGCTGCAAA

GAACGTTGGAATTGTTTCTTCTTTCTTTACTTATACTGGACCATCTGATA

ACAACCCATGGGATGAGATTGATATTGAGTTTCTTGGAAAGGATACTACT

AAGGTTCAATTCAACTGGTATAAGAATGGTGTTGGTGGAAACGAGTATCT

TCATAACCTTGGATTTGATGCTTCTCAAGATTTTCATACTTATGGTTTTG

AGTGGAGACCAGATTATATTGATTTTTATGTTGATGGAAAGAAGGTTTAT

AGAGGTACTAGAAACATTCCAGTTACTCCTGGAAAGATTATGATGAATCT

TTGGCCAGGAATTGGTGTTGATGAATGGCTTGGTAGATATGATGGAAGAA

CTCCACTTCAAGCTGAGTATGAGTATGTTAAGTATTATCCAAACGGTAGA

TCTGAATTCAAGCTTGTTGTTAATACTCCATTTGTTGCTGTTTTCTCTAA

CTTTGATTCTTCTCAATGGGAAAAGGCTGATTGGGCTAACGGTTCTGTTT

TTAACTGTGTTTGGAAGCCATCTCAAGTTACTTTTTCTAACGGAAAGATG

ATTCTTACTTTGGATAGAGAGTATGTCGACCATCATCATCATCATCATAA

GGATGAACTTTGACTCGAGCTC

SEQ ID NO.: 32:
MGFVLFSQLPSFLLVSTLLLFLVISHSCRAQNGGSYPYKSGEYRTKSFFG

YGYYEVRMKAAKNVGIVSSFFTYTGPSDNNPWDEIDIEFLGKDTTKVQFN

WYKNGVGGNEYLHNLGFDASQDFHTYGFEWRPDYIDFYVDGKKVYRGTRN

IPVTPGKIMMNLWPGIGVDEWLGRYDGRTPLQAEYEYVKYYPNGRSEFKL

VVNTPFVAVFSNFDSSQWEKADWANGSVFNCVWKPSQVTFSNGKMILTLD

REYVDHHHHHHKDEL pET expression vectors, derived from pBR322 plasmid, were engineered to take advantage of the features of the T7 bacteriophage gene 10 that promote high-level transcription and translation. The bacteriophage encoded RNA polymerase is highly specific for the T7 promoter sequences, which are rarely encountered in genomes other than T7 phage genome. pET-32 was used for fusing the alpha tubulin polytope ("Atub"), beta tubulin polytope ("Btub"), and full-length MAP15 ("MAP15") constructs into the loop region of a modified lichenase sequence that had been cloned in this vector. The catalytic domain of the lichenase gene with the upstream sequence PR-1A, with a KDEL sequence and a downstream $His_6$ tag were cloned between the BamHI and HindIII sites in a modified pET-32 vector (in which the region between the T7 promoter and the T7 terminator had been excised). In this way the pET-Atub-LicKM-KDEL, pET-Btub-LicKM-KDEL, pET-MAP15-LicKM-KDEL were obtained. Note that a vacuolar retaining sequence (VAC) could be used instead of the KDEL sequence.

DNA fragments of alpha tubulin, beta tubulin, and/or MAP15 were subcloned into the loop (1) portion of LicKM to give a fusion in the correct reading frame for translation. LicKM-Atub, LicKM-Btub, and LicKM-MAP15 fusions were constructed. The DNA fragment of Atub, Btub, or MAP15 was subcloned into the loop of LicKM using BamHI and HindIII sites to give a fusion in the correct reading frame for translation.

Target antigen constructs LicKM-Atub, LicKM-Btub, or LicKM-MAP15 were individually subcloned into the chosen viral vector (pBI-D4). pBI-D4 is a pBI121-derived binary vector in which the reporter gene coding for the *E. coli* β-D-glucuronidase (GUS) has been replaced by a "polylinker" where, between the XbaI and SacI sites, a TMV-derived vector has been cloned and is known as a "launch vector," as described herein. pBI-D4 is a TMV-based construct in which a foreign gene to be expressed (e.g., target antigen, such as LicKM-Atub, LicKM-Btub, LicKM-MAP15 replaces the coat protein (CP) gene of TMV. The virus retains the TMV 126/183 kDa gene, the movement protein (MP) gene, and the CP subgenomic mRNA promoter (sgp), which extends into the CP open reading frame (ORF). The start codon for CP has been mutated. The virus lacks CP and therefore cannot move throughout the host plant via phloem. However, cell-to-cell movement of viral infection remains functional, and the virus can move slowly to the upper leaves in this manner. A multiple cloning site (PacI-PmeI-AgeI-XhoI) has been engineered at the end of sgp for expression of foreign genes, and is followed by the TMV 3' non-translated region (NTR). The 35S promoter is fused at the 5' end of the viral sequence. The vector sequence is positioned between the BamHI and SacI sites of pBI121. The hammerhead ribozyme is placed 3' of the viral sequence (Chen et al., 2003, *Mol. Breed.*, 11:287). These constructs include fusions of sequences encoding LicKM-Atub, LicKM-Btub, or LicKM-MAP15 to sequences encoding the signal peptide from tobacco PR-1a protein, a 6×His tag and the ER-retention anchor sequence KDEL or vacuolar sequence. For constructs that contain sequence encoding PR-LicKM-Atub-KDEL, PR-LicKM-Btub-KDEL, and PR-LicKM-MAP15-KDEL, the coding DNA was introduced as PacI-XhoI fragments into pBI-D4. Nucleotide sequence was subsequently verified spanning the subcloning junctions of the final expression constructs.

Example 2

Generation of Plants and Antigen Production

Innoculation of Plants

Figure 3:
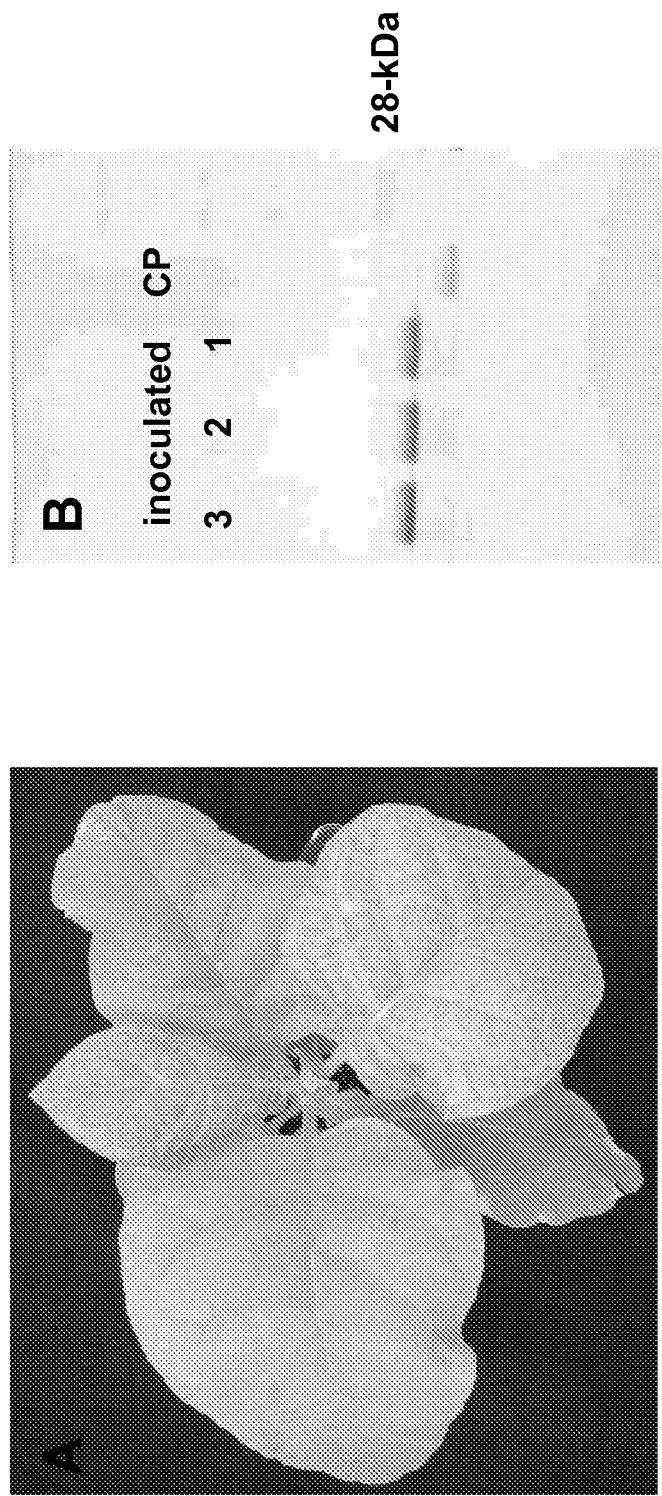
FIG. 3. Expression of chimeric AlMV CP containing target peptides. (A) Phenotype of an infected tobacco plant. (B) Western blot analysis of chimeric AlMV CP. Tobacco plants were inoculated with the AlMV-based RNA 3 vector. Stable expression of chimeric AlMV CP was observed in different inoculated leaves of tobacco plants. Samples were prepared in 5×SDS loading buffer, boiled for 8 minutes and centrifuged at 13,000 rpm before loading of 10 μl onto a 10% SDS PAGE gel. After separation of virus protein, gels were blotted to nitrocellulose membranes. Membranes were processed using polyclonal antisera against the AlMV coat protein as primary antibody and alkaline-phosphatase-labeled antibody as secondary antibody. CP: wild-type AlMV coat protein. Inoculated leaves 1-3: AlMV CP with target peptide.

Healthy leaves of transgenic *N. benthamiana* plants expressing modified AlMV P1 and P2 proteins were inoculated with RNA3 transcripts containing sequences encoding alpha tubulin-CP, beta tubulin-CP, and/or MAP15-CP fusion proteins. In vitro transcription reactions were performed following standard reaction protocols (see, for example, Lewandowski and Dawson, 1998, Virology, 251:427-437; and Ausubel et al., 1987, *Current Protocols in Molecular Biology*, Greene & Wiley, New York). Transcripts were diluted in 50% DEPC-treated water, 25% FES buffer, and 25% GP buffer and rubbed mechanically onto leaves that were dusted with carborundum, according to standard procedures (see, for example, Dawson et al., 1986, *Proc. Natl. Acad. Sci., USA*, 83:1832; and Knapp et al., 2001, *J. Virol.*, 75:5518). Inoculated leaves were harvested 4-7 days (e.g., 6 days) post-infiltration. Plants were screened for the presence of target antigen expression by SDS PAGE followed by Western blotting (FIG. 3).

*Agrobacterium* Infiltration of Plants

*Agrobacterium*-mediated transient expression system achieved by *Agrobacterium* infiltration was utilized (Turpen et al., 1993, *J. Virol. Methods*, 42:227) in accordance with the present invention. Healthy leaves of *N. benthamiana* were infiltrated with *A. rhizogenes* or *A. tumefaciens* (GV3101) containing viral vectors engineered to express LicKM-Atub, LicKM-Btub, and/or LicKM-MAP15 fusion proteins.

The *A. tumefaciens* strain GV3101 was transformed with the constructs pBI-D4-LicKM-Atub, pBI-D4-LicKM-Btub, pBI-D4-LicKM-MAP15, PR-LicKM-Atub-KDEL, PR-LicKM-Btub-KDEL, or PR-LicKM-MAP15-KDEL. *Agrobacterium* cultures were grown and induced as described by Kapila et al. (1997, *Plant Sci.*, 122: 101). A 2 ml starter-culture (picked from a fresh colony) was grown overnight in YEB (5 g/l beef extract, 1 g/l yeast extract, 5 g/l peptone, 5 g/l sucrose, 2 mM MgSO$_4$) with 25 µg/ml kanamycin at 28° C. The starter culture was diluted 1:500 into 500 ml of YEB with 25 µg/ml kanamycin, 10 mM 2-4(-morpholino)ethanesulfonic acid (MES) pH 5.6, 2 mM additional MgSO$_4$ and 20 µM acetosyringone. The diluted culture was then grown overnight to an O.D.$_{600}$ of approximately 1.7 at 28° C. The cells were centrifuged at 3,000×g for 15 minutes and re-suspended in MMA medium (MS salts, 10 mM MES pH 5.6, 20 g/l sucrose, 200 µM acetosyringone) to an O.D.$_{600}$ of 2.4, kept for 1-3 hours at room temperature, and used for *Agrobacterium*-infiltration. *N. benthamiana* leaves were injected with the *Agrobacterium*-suspension using a disposable syringe without a needle. Infiltrated leaves were harvested 4-7 days (e.g., 6 days) post-infiltration. Plants were screened for the presence of target antigen expression by SDS PAGE followed by Western blotting.

Example 3

Production of Vaccine Candidate

Purification of Virus Particles Expressing AlMV CP Fusion Proteins 100 mg samples of *N. benthamiana* infiltrated leaf material were harvested at 4, 5, 6 and 7 days post-infection. The fresh tissue was analysed for protein expression right after being harvested or collected at −80° C. for the preparation of subsequent crude plants extracts or for fusion protein purification. Plant material was kept on dry ice until grinding.

Plant tissue was ground in 3 volumes of extraction buffer (0.1 M NaPO$_4$, pH 7.1; 0.33 M sorbitol; 2.5 mM EDTA; and 2.5 mM DEDTC added immediately before use) for 2 minutes. Homogenate was spun for 30 minutes at 5,000×g, and supernatant (40 µl) and pellet samples were taken. The supernatant was filtered through Miracloth, and re-spun for 1-1.5 hours at 15,000×g (JLA 8100 rotor). A 40 µl sample of supernatant was isolated, and 10 µl of 1×SDS loading buffer was added. The solution was boiled, and 10 µl was loaded onto an SDS PAGE gel, which was subsequently stained with Coomassie brilliant blue. The purified supernatant was precipitated with 5%-10% PEG 20,000 for 1 hour at 4° C. After PEG is dissolved, the solution was stirred for 2-3 hours, and then spun for 30 minutes at 15,000×g. The supernatant was removed, and the pellet was resuspended in 30 ml of resuspension buffer (100 mM Na$_2$HPO$_4$, pH=7.1; 2.5 mM EDTA, pH 8) and frozen overnight at −20° C. The tubes were defrosted on ice and spun for 30 minutes at 15,000×g, followed by ultracentrifugation for 30 minutes at 30,000×g. The final solution was concentrated to 1 mg/ml. The protein concentration of the supernatant was measured and analyzed by SDS PAGE followed by Western blotting (FIG. 4).

Purification of Lichenase Fusion Proteins

For purification of PR-LicKM-Atub-KDEL, PR-LicKM-Btub-KDEL, and PR-LicKM-MAP15-KDEL from *N. benthamiana* leaf tissues, 100 g leaves were mixed with 250 ml 6 M guanidine; 50 mM sodium phosphate, pH 7.5; 100 mM NaCl. 10 mM β-Mercaptoethanol and 10 mM imidazole were added to the solution, and the solution was spun at 10,000 rpm for 30 minutes at 4° C. The supernatant was filtered through Miracloth, and spun again at 20,000 rpm for 30 minutes at 4° C. The supernatant was filtered through Miracloth and passed over 2 ml Ni-NTA beads by gravity flow. The beads were washed with 20 ml 6 M guanidine in PBS, then with 10 ml 25 mM imidazole and 6 M guanidine in PBS. Proteins were eluted with 10 ml 250 mM imidazole and 6 M guanidine in PBS. Beads were washed with 10 ml 1 M imidazole and 6 M guanidine in PBS. A solution of 1 mM DTT and 10 mM EDTA was added to the 250 mM imidazole fraction, and the sample was heated for 10 minutes. A 2× volume of 10 mM sodium carbonate, pH 9.5, and 500 mM NaCl was added, and the solution was heated for 5 minutes. The sample was incubated at room temperature for 4 hours to overnight. The resulting precipitate was spun down and dialyzed in 10 mM sodium carbonate, pH 9.5, and 250 mM NaCl overnight. The precipitate was spun down and concentrated to 1 mg/ml.

Alternatively or additionally, leaves from plants infiltrated with recombinant *Agrobacterium tumefaciens* containing the pBID4-LicKM-Atub-KDEL, pBID4-LicKM-Btub-KDEL, and pBID4-MAP15-KDEL constructs are ground by homogenization. Extraction buffer with "EDTA-free" protease inhibitors (Roche) and Triton X-100 1% is used at a ratio of 3 volumes w/v and rocked for 30 minutes at 4° C. Extracts are clarified by centrifugation at 9,000×g per 10 minutes at 4° C. The supernatant is sequentially filtered through Miracloth, centrifugated at 20,000×g for 30 minutes at 4° C., and filtered through 0.45-μm filter, before chromatographic purification.

Resulting extract is cut using ammonium sulfate precipitation. Briefly, $(NH_4)_2SO_4$ is added to extract to 20% saturation, incubated on ice for 1 hour, and spun down at 18,000×g for 15 minutes. Pellet is discarded and $(NH_4)_2SO_4$ is added slowly to 60% saturation, incubated on ice for 1 hour, and spun down at 18,000×g for 15 minutes. Supernatant is discarded, and resulting pellet is resuspended in buffer, then maintained on ice for 20 minutes, followed by centrifugation at 18,000×g for 30 minutes. Supernatant is dialyzed overnight against 10,000 volumes of washing buffer:

His-tagged LicKM-Atub-KDEL, LicKM-Btub-KDEL, and LicKM-MAP15-KDEL chimeric proteins are purified by using IMAC ("Immobilized Metal Affinity Chromatography," GE Healthcare) at room temperature under gravity. The purification is performed under non-denaturing conditions. Proteins are collected as 0.5 ml fractions, which are unified, added with 20 mM EDTA, dialyzed against 1×PBS overnight at 4° C., and analyzed by SDS-PAGE.

Alternatively, fractions are then collected together added with 20 mM EDTA, dialyzed against $NaH_2PO_4$ 10 mM overnight at 4° C., and purified by Anion Exchange Chromatography. For LicKM-Atub-KDEL, LicKM-Btub-KDEL, and LicKM-MAP15-KDEL purification, anion exchange column Q Sepharose Fast Flow (Amersham Pharmacia Biosciences) is used. Samples of the LicKM-Atub-KDEL, LicKM-Btub-KDEL, and LicKM-MAP15-KDEL affinity or ion-exchange purified chimeric proteins are separated on 12% polyacrylamide gels followed by Coomassie staining. Separated proteins are also electrophoretically transferred onto PDVF membranes for Western blot analysis using polyclonal anti-lichenase antibody and successively with anti-rabbit IgG horseradish peroxidase-conjugated antibody.

Collected fractions after dialysis are analyzed by immunoblotting using both the pAb α-lichenase and the pAb α-$His_6$. The His-tag is maintained by the expressed chimeric proteins and the final concentration of the purified protein is evaluated by software.

Example 4

Mouse Immunogenicity and Challenge Studies

Immunogenicity studies were conducted to determine whether plant-produced antigen fusion-based vaccines could protect mice against *Trypanosoma* (i.e. *T. brucei*) infection. The antigens utilized in these studies are purified virus particles expressing alpha tubulin-CP, beta tubulin-CP, and MAP15-CP fusion proteins, as described above.

Mouse Immunogenicity and Challenge Study #1

In the first immunogenicity study, ten groups of Swiss Webster mice (8 weeks old; 10 mice per group) were injected intraperitoneally with pools of recombinant virus particles, with each recombinant particle at 100 μg for the first dose and 50 μg for the second and third doses. The first dose was administered at day 0 with complete Freund's adjuvant, the second dose was administered at day 14 with incomplete Freund's adjuvant, and the third dose was administered at day 28 without adjuvant. The immunization schedule is summarized in Table 5:

TABLE 5

Immunization Schedule for First Mouse Immunogenicity Study

| Group | Antigen | Dose (μg) at day 0 | Dose (μg) at day 14 | Dose (μg) at day 28 |
|---|---|---|---|---|
| 1 | AlMV CP | 400 | 200 | 200 |
| 2 | Atub (1-4) | 400 | 200 | 200 |
| 3 | Atub (5-8) | 400 | 200 | 200 |
| 4 | Btub (1-4) | 400 | 200 | 200 |
| 5 | Btub (5-8) | 400 | 200 | 200 |
| 6 | MAP15 | 200 | 100 | 100 |
| 7 | MAP15 + Atub (1-4) | 600 | 300 | 300 |
| 8 | MAP15 + Atub (5-8) | 600 | 300 | 300 |
| 9 | MAP15 + Btub (1-4) | 600 | 300 | 300 |
| 10 | MAP15 + Btub (5-8) | 600 | 300 | 300 |
| 11 | Native tubulin | 40 | 20 | 20 |
| 12 | Adjuvant alone | 0 | 0 | 0 |

Mice in all groups were challenged 15 days after the third dose with $10^2$ *T. brucei* strain UTRO 010291B. Mice were monitored daily for parasitemia from the third to seventh day after challenge. After the first week, monitoring for parasitemia was done weekly up to day 60 post-challenge. The composition of the pools and the results of the study are presented in Table 6:

TABLE 6

Summary of First Mouse Immunogenicity Study

| Antigen Used | % Animals Surviving Challenge |
|---|---|
| Atub (1-4) | 60 |
| Atub (5-8) | 70 |
| Btub (1-4) | 90 |
| Btub (5-8) | 90 |
| AlMV | 0 |
| MAP15 | 0 |
| MAP15 + Atub (1-4) | 0 |
| MAP15 + Atub (5-8) | 0 |
| MAP15 + Btub (1-4) | 0 |
| MAP15 + Btub (5-8) | 0 |
| Native tubulin | 0 |
| Adjuvant alone | 0 |

In Table 6, "Atub (1-4)" is a mixture of recombinant particles containing alpha tubulin peptides 1-10, 2-13, 6-19, and 7-29 (SEQ ID NOs.: 4, 5, 9, and 10, respectively); "Atub (5-8)" is a mixture of recombinant particles containing alpha tubulin peptides 3-17, 4-11, and 8-21 (SEQ ID NOs.: 6, 7, and 11, respectively); "Btub (1-4)" is a mixture of recombinant particles containing beta tubulin peptides 2-4, 3-24, 5-14, and 11-31 (SEQ ID NOs.: 13, 14, 16, and 22, respectively); and "Btub (5-8)" is a mixture of recombinant particles containing beta tubulin peptides 1-1, 7-19, 8-22, and 9-25 (SEQ ID NOs.: 12, 18, 19, and 20, respectively); see Table 7 for peptide sequences. Four groups were also administered recombinant particles containing peptides from MAP15.

Four candidate vaccines provided significant protection against challenge infection with at least 60% of the animals surviving the challenge: Atub (1-4) and Atub (5-8) provided 60%-70% protection, whereas, Btub (1-4) and Btub (5-8) provided 90% protection. None of the animals in the negative control group that received wild type AlMV particles survived the challenge. Groups that received MAP15 were not protected. Therefore, MAP15 was not included in further compositions.

In addition, ELISA assays were performed to determine whether immunized mice had produced antibodies that recognize *T. brucei* antigens. In these experiments, serum was obtained from mice 3 days prior to immunization and challenge. Briefly, blood obtained from mice was coagulated on ice for 30 minutes. Blood was centrifuged at 8000 rpm for 5 minutes. Serum was aspirated into a new tube. The centrifugation step was repeated to avoid contamination with red blood cells. Serum was stored at −80° C.

ELISAs were carried out essentially as follows. Plates were coated overnight with 100 ng of either tubulin purified from *T. b. brucei*, α-tubulin polytope, β-tubulin polytope, synthesized β-tubulin 2-4, or β-tubulin 5-14 peptides conjugated to KLH (Keyhole Limpet Hemocyanin). Coated plates were blocked for 2 hours at room temperature. Sera were serially diluted in I-Block (5 g I-Block powder/l) and 50 µl were added per well. Plates were incubated on a shaker for 2 hours at room temperature and then washed in wash buffer (phosphate buffered saline; 0.05% Tween-20). Horseradish peroxidase (HRP) conjugated secondary antibody α-mouse IgG or IgG subtype) was diluted in I-Block (at 1:10,000) and 50 µl were added per well. Plates were incubated for 1 hour at room temperature on a shaker and then washed in wash buffer. 90 µl of OPD substrate (1 OPD buffer tablet and 1 OPD substrate tablet per 20 ml water) was added to each well. Plates were incubated in the dark until optimal color developed (about 10 minutes). 10 µl of 5 M $H_2SO_4$ were added to each well to stop the reaction, and absorbance was read at 490 nm.

Figure 5A:
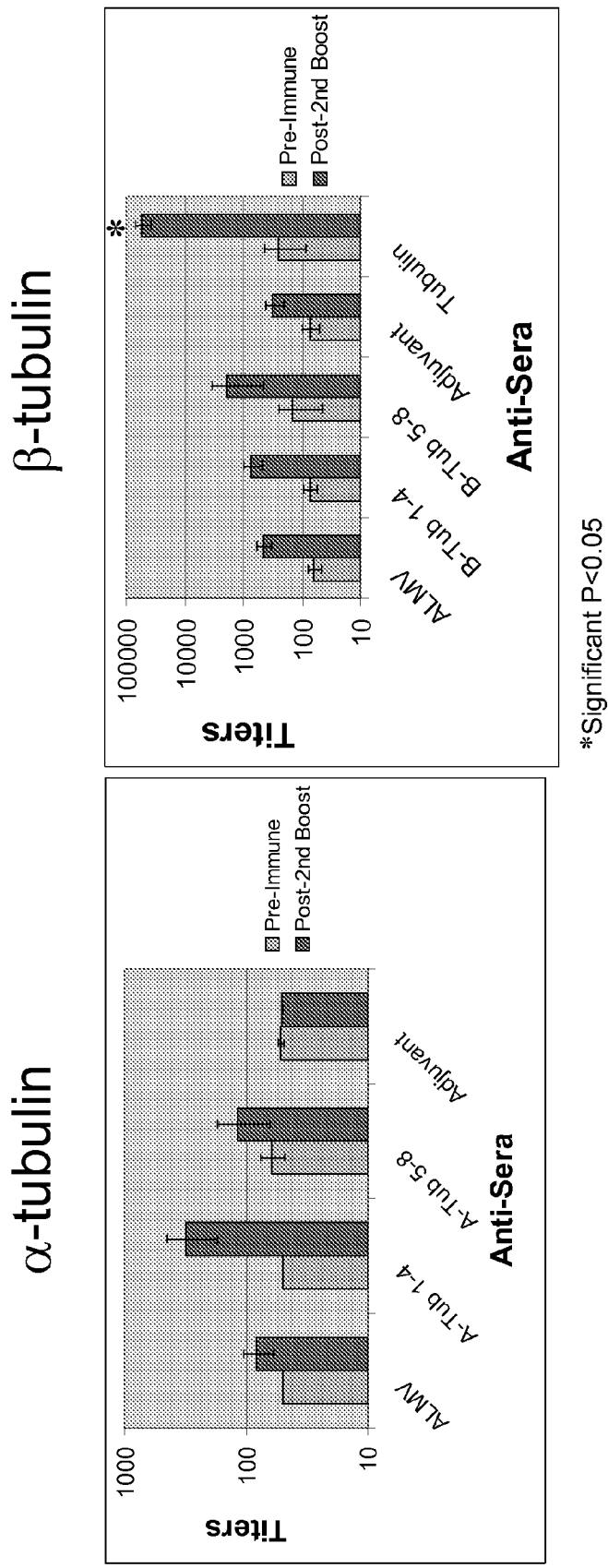
FIG. 5. Analysis of serum for antibodies that recognize *T. brucei* antigens: mouse study #1. ELISA assays were performed to determine whether immunized mice had produced antibodies that recognize *T. brucei* antigens. Tubulin peptide-specific IgGs were detected in mouse sera obtained after the third immunization. Total IgG titers of the α-tubulin (Atub (1-4), Atub (5-8)) or β-tubulin (Btub (1-4), Btub (5-8)) test groups were higher than those from the control groups (adjuvant or wild-type virus particles), albeit not significantly. Mice immunized with purified *T. b. brucei* tubulin had significant IgG titers (FIG. 5A). Analysis of IgG subtypes revealed that all test groups had elevated IgG1 titers, which were significant for groups Atub (1-4), Atub (5-8), Btub (1-4), full-length tubulin, but not Btub (5-8) when compared to the control groups. IgG2a and IgG2b titers of all test groups did not differ significantly from control groups, with the exception of those that were induced against full-length tubulin (FIG. 5B). * indicates statistically significant results ($p<0.05$).
Figure 5B:
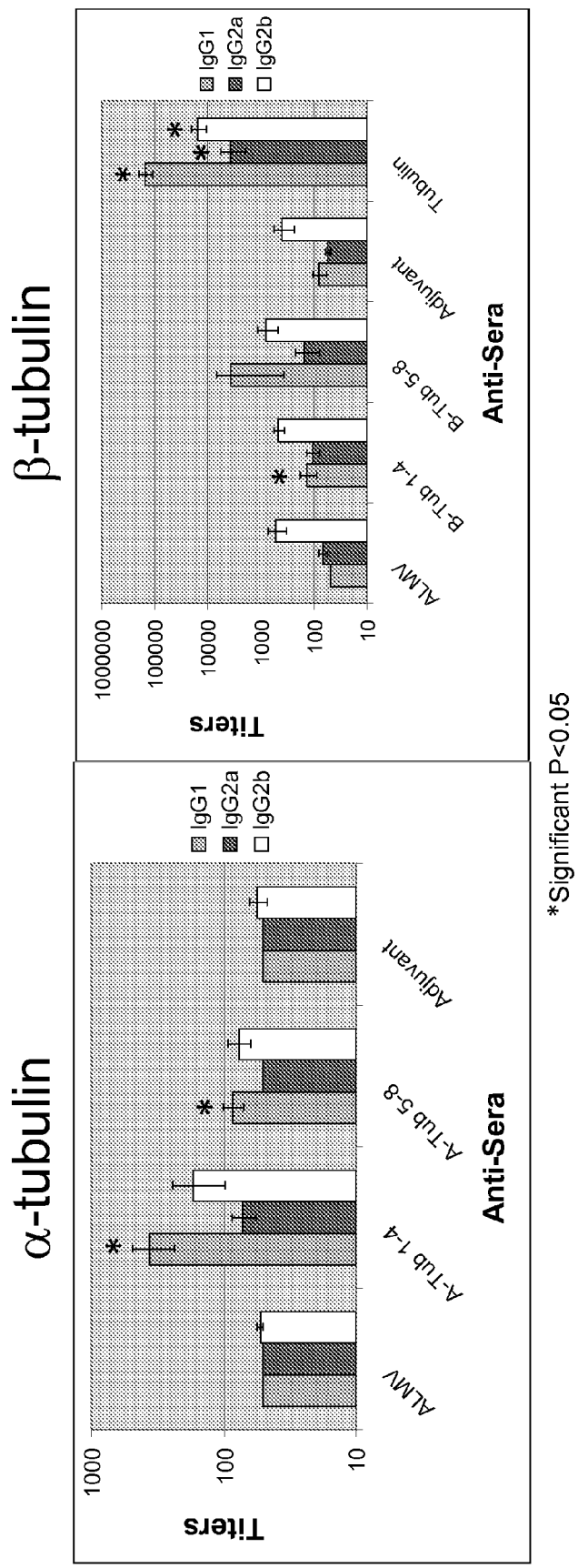
Figure 6A:
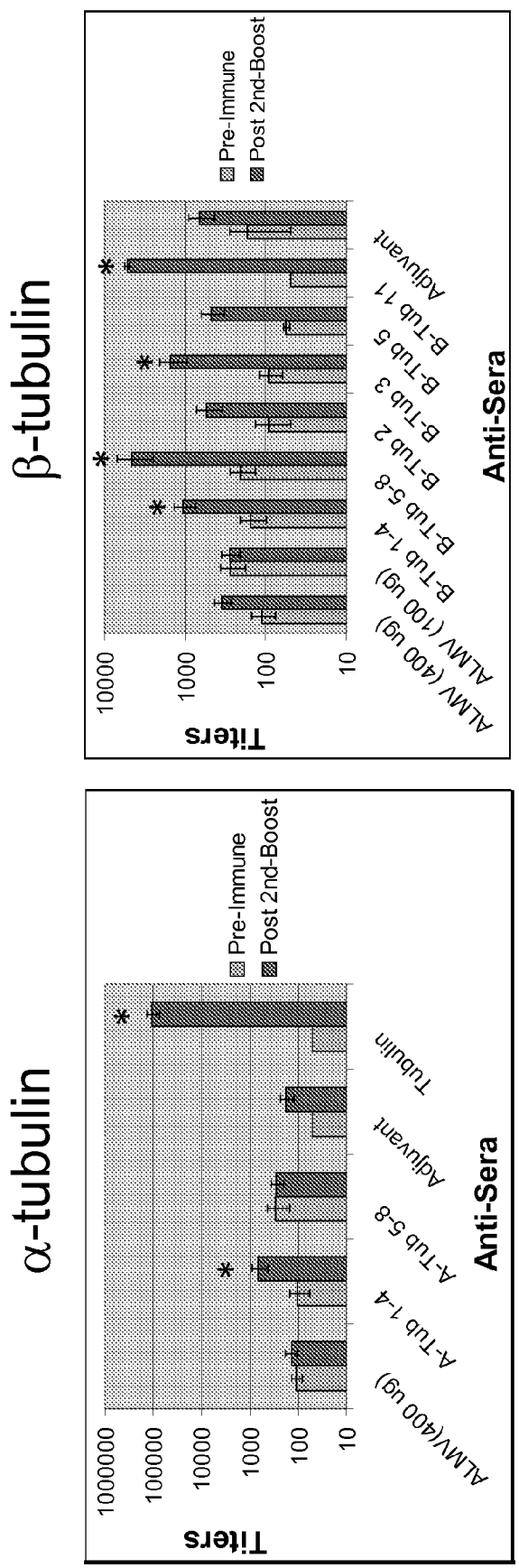
FIG. 6. Analysis of serum for antibodies that recognize *T. brucei* antigens: mouse study #2. ELISA assays were performed to determine whether immunized mice had produced antibodies that recognize *T. brucei* antigens. All sera obtained after the $3^{rd}$ immunization had elevated total IgG titers compared to the corresponding pre-immune sera, with the exception of sera from Atub (5-8). Compared to control groups (e.g., adjuvant or wild-type virus particles) total IgG titers were significant for Atub (1-4), recombinant full-length α-tubulin, Btub (1-4), Btub (5-8), Btub 3, Btub 11, purified tubulin, and recombinant full-length β-tubulin (FIG. 6A). The IgG subtype pattern of Atub (1-4), Btub (1-4), Btub (5-8), and tubulin was similar to that observed in Mouse Study #1 in that IgG1 was the dominant subtype. None of the subtype antibody titers of the groups that tested individual tubulin peptides (Btub 2-4, Btub 3-24, Btub 5-14) were statistically significant with the exception of Btub 11-31 that had high IgG1 followed by IgG2a and IgG2b (FIG. 6B). * indicates statistically significant results ($p<0.05$).
Figure 6B:
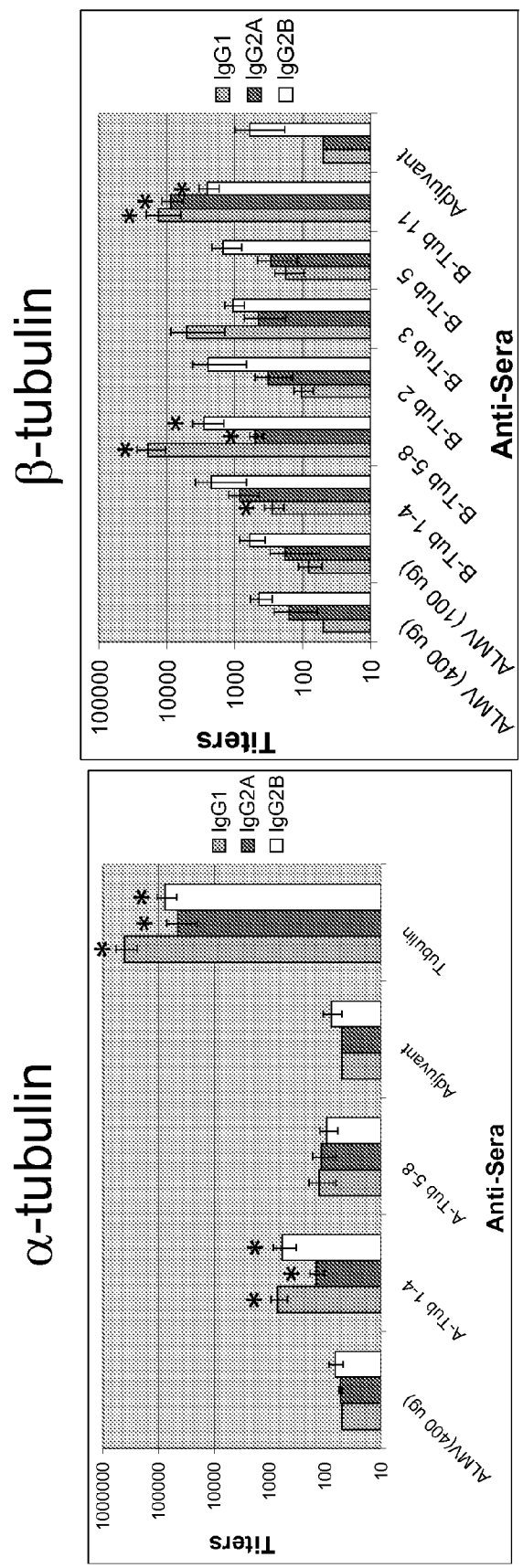

Results of these experiments are presented in FIG. 5A-B. Tubulin peptide-specific IgGs were detected in mouse sera obtained after the third immunization. Total IgG titers of the α-tubulin (Atub 1-4, Atub 5-8) or β-tubulin (Btub 1-4, Btub 5-8) test groups were higher than those from the control groups (adjuvant or wild-type virus particles), albeit not significantly. Mice immunized with purified *T. b. brucei* tubulin had significant IgG titers (FIG. 5A). Analysis of IgG subtypes revealed that all test groups had elevated IgG1 titers, which were significant for groups Atub 1-4, Atub 5-8, Btub 1-4, full-length tubulin, but not Btub 5-8 when compared to the control groups. IgG2a and IgG2b titers of all test groups did not differ significantly from control groups, with the exception of those that were induced against full-length tubulin (FIG. 5B).

Antibody titers and survival rates did not necessarily correlate well. Thus, the present invention encompasses the recognition that protection may not solely be based on humoral immune responses, but might also involve cell-mediated immune mechanisms. Alternatively or additionally, antibodies generated against one or more of the vaccine candidates might not be recognized by the coating reagents used in ELISA.

Collectively, these data suggest that peptides from alpha and beta tubulin have potential for vaccine development, and thus were selected for further characterization and evaluation (see Table 7).

TABLE 7

Peptides from alpha and beta tubulin selected for further evaluation

| Target Peptide | Amino Acid Sequence | Position of Peptide |
|---|---|---|
| Alpha tubulin | | |
| 1-10 (18 aa) | REAICIHIGQAGCQVGNA (SEQ ID NO.: 4) | 2-19 |
| 2-13 (14 aa) | TGSGLGALLLERLS (SEQ ID NO.: 5) | 145-158 |

TABLE 7-continued

Peptides from alpha and beta tubulin selected for further evaluation

| Target Peptide | Amino Acid Sequence | Position of Peptide |
|---|---|---|
| 3-17 (24 aa) | YNSVLSTHSLLEHTDVAAMLDNEA (SEQ ID NO.: 6) | 185-208 |
| 4-11 (15aa) | NRLIGQVVSSLTASL (SEQ ID NO.: 7) | 228-242 |
| 5-18 (14aa) | IHFVLTSYAPVISA (SEQ ID NO.: 8) | 265-278 |
| 6-19 (21 aa) | LSVSEISNAVFEPASMMTKCD (SEQ ID NO.: 9) | 286-306 |
| 7-29 (18aa) | DVNAAVATIKTKRTIQFV (SEQ ID NO.: 10) | 327-344 |
| 8-21 (20aa) | VCMIANSTAIAEVFARIDHK (SEQ ID NO.: 11) | 375-394 |
| Beta tubulin | | |
| 1-1 (18aa) | DEHGVDPTGTYQGDSDLQ (SEQ ID NO.: 12) | 26-43 |
| 2-4 (9aa) | PRSVLIDLE (SEQ ID NO.: 13) | 61-69 |
| 3-24 (13 aa) | SVRAGPYGQIFRP (SEQ ID NO.: 14) | 75-89 |
| 4-12 (23aa) | LLISKLREQYPDRIMMTFSIIPS (SEQ ID NO.: 15) | 150-172 |
| 5-14 (14 aa) | HQLVENSDESMCID (SEQ ID NO.: 16) | 190-203 |
| 6-18 (12aa) | VSAVVSGVTCCL (SEQ ID NO.: 17) | 229-240 |
| 7-19 (11aa) | QYRGLSVPELT (SEQ ID NO.: 18) | 280-290 |
| 8-22 (17aa) | SYFIEWIPNNIKSSVCD (SEQ ID NO.: 19) | 339-355 |
| 9-25 (12aa) | PPKGLKMAVTFI (SEQ ID NO.: 20) | 357-368 |
| 10-28 (20aa) | NTCIQEMFRRVGEQFTLMFR (SEQ ID NO.: 21) | 371-390 |
| 11-31 (15aa) | DATIEEEGEFDEEEQ (SEQ ID NO.: 22) | 427-441 |

Mouse Immunogenicity and Challenge Study #2

Selected peptides were purified and evaluated in a second trial of the mouse challenge model. Peptides were combined into four pools identical to those in the first immunogenicity study, and four peptides (Btub 2-4, 3-24, 5-14, and 11-31) were also assessed individually. The immunization and challenge schedule for the second immunogenicity study was identical to that of the first immunogenicity study, except that 15 mice were included per group, the challenge was delayed, and mice were administered a third booster dose on day 65, prior to challenge on day 86. The immunization schedule is presented in Table 8:

TABLE 8

| Immunization Schedule for Second Mouse Immunogenicity Study | | | | | |
|---|---|---|---|---|---|
| Group | Antigen | Dose (μg) at day 0 | Dose (μg) at day 14 | Dose (μg) at day 28 | Dose (μg) at day 65 |
| 1 | AlMV CP | 400 | 200 | 200 | 200 |
| 2 | AlMV CP | 100 | 50 | 50 | 50 |
| 3 | Atub (1-4) | 400 | 200 | 200 | 200 |
| 4 | Atub (5-8) | 400 | 200 | 200 | 200 |
| 5 | Btub (1-4) | 400 | 200 | 200 | 200 |
| 6 | Btub (5-8) | 400 | 200 | 200 | 200 |
| 7 | Btub 2-4 | 100 | 50 | 50 | 50 |
| 8 | Btub 3-24 | 100 | 50 | 50 | 50 |
| 9 | Btub 5-14 | 100 | 50 | 50 | 50 |
| 10 | Btub 11-31 | 100 | 50 | 50 | 50 |
| 11 | tubulin | 40 | 20 | 20 | 20 |
| 12 | adjuvant | 0 | 0 | 0 | 0 |

The results of the second immunogenicity study are presented in Table 9:

TABLE 9

| Summary of Second Mouse Immunogenicity Study | |
|---|---|
| Antigen Used | % Animals Surviving Challenge |
| AlMV (400 μg) | 13 |
| AlMV (100 μg) | 20 |
| Atub (1-4) | 40 |
| Atub (5-8) | 40 |
| Btub (1-4) | 53 |
| Btub (5-8) | 100 |
| Btub 2-4 | 100 |
| Btub 3-24 | 0 |
| Btub 5-14 | 100 |
| Btub 11-31 | 40 |
| Native tubulin | 27 |
| Adjuvant alone | 13 |
| Atub (recomb. full length) | 27 |
| Btub (recomb. full length) | 33 |
| Untreated | 0 |

The results of the second study confirmed the results of the first study. Atub (1-4) and (5-8) provided 40% protection which is comparable to results from the first study (see Table 6, 60-70% protection), and Btub (5-8) provided 100% protection, which confirmed results of the first study (90% protection). Btub (1-4), on the other hand, provided 53% protection in this study, whereas in the first study, this pool provided 90% protection. However, analysis of the contribution of individual components of this pool showed that 2 components of the pool, Btub 2-4 and 5-14, provided 100% protection against challenge, while Btub 11-31 provided 40% protection, and Btub 3-24 did not provide any protection. Full-length alpha tubulin or beta tubulin produced in *E. coli* provided only 27-33% protection to immunized animals, and control groups that received wild type AlMV particles plus adjuvant or adjuvant alone showed only 13% survival.

In addition, ELISA assays were performed to determine whether immunized mice had produced antibodies that recognize *T. brucei* antigens. These experiments were performed substantially as described for Mouse Immunogenicity and Challenge Study #1.

Results of these experiments are presented in FIGS. 6A-B. All sera obtained after the 3$^{rd}$ immunization had elevated total IgG titers compared to the corresponding pre-immune sera, with the exception of sera from Atub 5-8. Compared to control groups (e.g., adjuvant or wild-type virus particles) total IgG titers were significant for Atub 1-4, recombinant full-length α-tubulin, Btub 1-4, Btub 5-8, Btub 3, Btub 11, purified tubulin, and recombinant full-length β-tubulin (FIG. 6A). The IgG subtype pattern of Atub 1-4, Btub 1-4, Btub 5-8, and tubulin was similar to that observed in Mouse Study #1 in that IgG1 was the dominant subtype. None of the subtype antibody titers of the groups that tested individual tubulin peptides (Btub2, Btub3, Btub5) were statistically significant with the exception of Btub 11 that had high IgG1 followed by IgG2a and IgG2b (FIG. 6B).

Antibody titers and survival rates did not necessarily correlate well. Thus, the present invention encompasses the recognition that protection may not solely be based on humoral immune responses, but might also involve cell-mediated immune mechanisms.

Mouse Immunogenicity and Challenge Study #3

A third mouse immunogenicity study is performed in order to determine the contribution of each individual peptide to protection. The outline for this study is shown in Table 10:

TABLE 10

| Immunization Schedule for Third Mouse Immunogenicity Study | | | | | |
|---|---|---|---|---|---|
| Group | Vaccine (intraperitoneally) | Adjuvant | 1$^{st}$ Dose (μg/dose) | 2$^{nd}$ Dose (μg/dose) | 3$^{rd}$ Dose (μg/dose) |
| 1 | AlMV | CFA | 600 | 300 | 300 |
| 2 | AlMV | CFA | 100 | 50 | 50 |
| 3 | Atub (1-4) | CFA | 400 | 200 | 200 |
| 4 | Atub (5-8) | CFA | 300 | 150 | 150 |
| 5 | Atub 1-10 | CFA | 100 | 50 | 50 |
| 6 | Atub 2-13 | CFA | 100 | 50 | 50 |
| 7 | Atub 3-17 | CFA | 100 | 50 | 50 |
| 8 | Atub 4-11 | CFA | 100 | 50 | 50 |
| 9 | Atub 6-19 | CFA | 100 | 50 | 50 |
| 10 | Atub 7-29 | CFA | 100 | 50 | 50 |
| 11 | Btub (1-4) | CFA | 400 | 200 | 200 |
| 12 | Btub (5-8) + Btub 2-4 + Btub 5-14 | CFA | 600 | 300 | 300 |
| 13 | Btub 2-4 | CFA | 100 | 50 | 50 |
| 14 | Btub 5-14 | CFA | 100 | 50 | 50 |
| 15 | Btub 11-31 | CFA | 100 | 50 | 50 |
| 16 | Btub 1-1 | CFA | 100 | 50 | 50 |
| 17 | Btub 7-19 | CFA | 100 | 50 | 50 |
| 18 | Btub 8-22 | CFA | 100 | 50 | 50 |
| 19 | Btub 9-25 | CFA | 100 | 50 | 50 |
| 20 | Btub 5-14 | Alhydrogel | 100 | 50 | 50 |
| 21 | Btub 2-4 | Alhydrogel | 100 | 50 | 50 |
| 22 | Btub 5-14 | — | 100 | 50 | 50 |
| 23 | Btub 2-4 | — | 100 | 50 | 50 |
| 24 | Adjuvant | Alhydrogel | 0 | 0 | 0 |
| 25 | Adjuvant | CFA | 0 | 0 | 0 |

The dosing and challenge regimen is similar to that used for the first immunogenicity study, but there are 10 animals per group. All animals except those in groups 20 to 25 receive the vaccine candidate in the presence of complete Freund's adjuvant (CFA; dose 1) and incomplete Freund's adjuvant (dose 2). Animals in groups 20 and 21 receive Btub 2 or Btub 5, respectively, in the presence of Alhydrogel provided by the sponsor (dose 1 and 2), and animals in groups 22 and 23 receive Btub 2 or Btub5, respectively, in the absence of any adjuvant. Alhydrogel is used as adjuvant in the cattle studies, and therefore it is included in three of the groups in this mouse study, two experimental and one control, to assess its contribution to inducing protective immunity. Mice in all study groups are challenged at day 38 with 500 parasites (*T. brucei*).

Mouse Immunogenicity and Challenge Study #4

A fourth mouse immunogenicity study is performed in order to determine the contribution of each individual peptide to protection. In the fourth immunogenicity study, eight groups of Swiss Webster mice (8-9 weeks old; 10 mice per group) were injected subcutaneously between the shoulder blades with vaccine candidate(s) at 200 μl/dose plus 10 μl of 1 mg/ml QuilA. Administration is performed on Study Days 0, 14, and 28 according to the dosage schedule shown in Table 11:

TABLE 11

Immunization Schedule for Fourth Mouse Immunogenicity Study

| Group | Vaccine | $1^{st}$ Dose (μg/dose) | $2^{nd}$ Dose (μg/dose) | $3^{rd}$ Dose (μg/dose) | Challenge *T. b brucei* UTRO 010291B |
|---|---|---|---|---|---|
| 1 | AlMV | 100 | 50 | 50 | $10^2$ |
| 2 | Btub (5-8) | 400 | 200 | 200 | $10^2$ |
| 3 | Btub 1-1 | 100 | 50 | 50 | $10^2$ |
| 4 | Btub 7-19 | 100 | 50 | 50 | $10^2$ |
| 5 | Btub 8-22 | 100 | 50 | 50 | $10^2$ |
| 6 | Btub 9-25 | 100 | 50 | 50 | $10^2$ |
| 7 | No vaccine | — | — | — | $10^2$ |
| 8 | clean | — | — | — | $10^2$ |

Serum is collected 3 days prior to the first dose, 9 days after the second dose, and 7 days after the third dose. Mice in all groups are challenged 10 days after the third dose with $10^2$ *T. b brucei* strain UTRO 010291B.

Mouse Immunogenicity and Challenge Study #5

A fifth mouse immunogenicity study was performed in order to select peptides from pools, that provided protection against *Trypanosoma brucei*, and to test them individually for their contribution to the overall protection rate observed in earlier trials. In addition, LicKM-AtubPolytope and LicKM-BtubPolytope antigens were tested for protective efficacy against *T. b. brucei*. The polytopes contained all alpha or beta tubulin peptides, respectively, fused in tandem. They were expressed as polypeptides from within the surface loop of lichenase, which acts as a thermostable carrier protein. The AlMV and LicKM (lichenase) groups served as negative controls. Btub2 and Btub5 each gave 100% protection in Mouse Study #2 and were thus included as reference groups (Table 12):

TABLE 12

Immunization Schedule for Fifth Mouse Immunogenicity Study

| Group | Vaccine | Adjuvant | $1^{st}$ Dose (μg/dose) | $2^{nd}$ Dose (μg/dose) | $3^{rd}$ Dose (μg/dose) |
|---|---|---|---|---|---|
| 1 | AlMV | QuilA | 100 | 50 | 50 |
| 2 | Atub 1-10 | QuilA | 100 | 50 | 50 |
| 3 | Atub 4-11 | QuilA | 100 | 50 | 50 |
| 4 | Btub 2-4 | QuilA | 100 | 50 | 50 |
| 5 | Btub 5-14 | QuilA | 100 | 50 | 50 |
| 6 | LicKM | QuilA | 140 | 70 | 70 |
| 7 | LicKM-AtubPolytope | QuilA | 200 | 100 | 100 |
| 8 | LicKM-BtubPolytope | QuilA | 200 | 100 | 100 |
| 9 | No vaccine | QuilA | — | — | — |
| 10 | clean | — | — | — | — |

Female Swiss Webster mice (7-8 weeks old), 7 per group, were vaccinated subcutaneously between the shoulder blades. The volume of vaccine candidate was 200 μl per dose plus 10 μl of QuilA (1 mg/ml). Dose administration was performed on Study Days 0, 14 and 28. Challenge was scheduled 10 days after the third dose, however several mice had died at this time point due to unknown causes. Challenge was performed 19 days after the third dose, once the number of animals had stabilized. Mice were challenged with $5\times10^2$ *T. brucei brucei* strain UTRO 010291B. This challenge dose was 2.5-fold higher than the one used in Mouse Study #2 reflecting an ongoing effort to standardize parasitological methods.

The number of animals per group that survived the challenge is given in Table 13.

TABLE 13

Surviving Mice in Mouse Study #5

| Group | Vaccine | Surviving Animals/ Total |
|---|---|---|
| 1 | AlMV | 2/6 |
| 2 | Atub 1-10 | 1/4 |
| 3 | Atub 4-11 | 0/7 |
| 4 | Btub 2-4 | 3/5 |
| 5 | Btub 5-14 | 4/7 |
| 6 | LicKM | 1/7 |
| 7 | LicKM-AtubPolytope | 0/6 |
| 8 | LicKM-BtubPolytope | 0/6 |
| 9 | Adjuvant alone | 1/7 |
| 10 | Clean | 0/5 |
| 11 | Clean/clean | 5/5 |

[a]Number of surviving animals per total number of animals within each group

Atub 1-10, Atub 4-11, LicKM-AtubPolytope, LicKM-BtubPolytope, ALMV control, and adjuvant control groups were not protective. Most animals immunized with Btub 2-4 or Btub 5-14 survived the challenge. Survivors were completely protected as they did not show parasites in their blood post challenge. The Btub 2 and Btub 5 results are consistent with the previous protection observed in Mouse Study #2.

Example 5

Model System of *T. brucei* Vaccination

Cattle Reconstruction Study #1

This study defines experimental conditions for cattle, including the challenge dose of parasite for subsequent cattle studies. Details of the cattle reconstruction study are shown in Table 14:

TABLE 14

Experimental Design of Cattle Reconstruction Study #1

| Group | Vaccine (Intramuscular) | 1st Dose (μg/dose) | 2nd Dose (μg/dose) | 3rd Dose (μg/dose) | Challenge T. brucei brucei strain UTRO 010291B intramuscular |
|---|---|---|---|---|---|
| 1 | AlMV + Alhydrogel | 1000 | 3000 | 3000 | $5 \times 10^3$ |
| 2 | AlMV + Alhydrogel | 1000 | 3000 | 3000 | $5 \times 10^6$ |
| 3 | Btub 2-4 + Btub 5-14 + Alhydrogel | 500 + 500 | 1500 + 1500 | 1500 + 1500 | $5 \times 10^3$ |
| 4 | Btub 2-4 + Btub 5-14 + Alhydrogel | 500 + 500 | 1500 + 1500 | 1500 + 1500 | $5 \times 10^6$ |
| 5 | Btub 2-4 + Btub 5-14 | 500 + 500 | 1500 + 1500 | 1500 + 1500 | $5 \times 10^3$ |
| 6 | Untreated animals | — | — | — | $5 \times 10^3$ |

Female Ankole cattle (approximately 18 months old), four in each group, were immunized at days 0, 14 and 28. Serum samples (10 ml) were collected prior to each immunization and before challenge on day 39 for immunogenicity analyses. Samples of blood were collected to monitor for parasitemia, to determine packed cell volume (PCV), and to obtain sera for immunogenicity assays. Parasitemia and PCV were monitored until 45 days post challenge.

500 μg of Btub 2 and 500 μg of Btub5 were separately administered intramuscularly at two different injection sites. Second and third immunizations were done similarly with 1500 μg each. In the case of AlMV, 1000 μg of particles were split between two injection sites with 500 μg/site. All animals except those in Group 5 received vaccine candidate in the presence of alhydrogel (2%). Animals in Group 6 did not receive any immunization treatment, but were challenged at day 39. In this study, two challenge doses of parasite ($5 \times 10^3$ and $5 \times 10^6$) were examined to determine the optimal dose for subsequent cattle studies.

Animals in groups immunized with wild-type or recombinant particles that received a challenge dose of $5 \times 10^3$ parasites per animal did not show any parasitemia after 17 days. On the other hand, animals that were challenged with $5 \times 10^6$ parasites showed parasitemia. Specifically, groups of animals that received wild-type AlMV particles (control) showed parasitemia 7 days post challenge, whereas groups of animals receiving recombinant AlMV particles did not have parasitemia until day 17 post challenge, suggesting that the target peptides conferred significant protection. A challenge dose of $5 \times 10^6$ parasites per animal was chosen for subsequent cattle experiments.

Cattle Reconstruction Study #2

This study was performed to determine whether $5 \times 10^4$ or $5 \times 10^5$ parasites per animal can establish an infection in Ankole cattle.

TABLE 15

Parasitemia in Cattle Post-Challenge

| Groups | cow | -4 | 7 | 10 | 12 | 14 | 17 | 40 Pa | 40 AI | 45 Pa | 45 AI | 45 PCR | 45 ELISA |
|---|---|---|---|---|---|---|---|---|---|---|---|---|---|
| 1 AlMV $5 \times 10^3$ | 1 | − | − | − | − | − | − | − | − | − | − | + | − |
| | 2 | − | − | − | − | − | − | − | − | − | − | + | − |
| | 3 | − | − | − | − | − | − | − | − | − | − | + | − |
| | 4 | − | − | − | − | − | − | − | − | − | − | + | − |
| 2 AlMV $5 \times 10^6$ | 1 | − | − | − | + | + | + | − | + | − | + | + | + |
| | 2 | − | + | + | + | + | + | − | + | − | + | + | + |
| | 3 | − | + | + | + | + | + | − | + | − | + | + | + |
| | 4 | − | + | + | + | + | + | − | + | − | + | + | + |
| 3 Btub 2-4 + Btub 5-14 $5 \times 10^3$ | 1 | − | − | − | − | − | − | − | − | − | − | + | − |
| | 2 | − | − | − | − | − | − | − | − | − | − | − | − |
| | 3 | − | − | − | − | − | − | − | − | − | − | + | − |
| | 4 | − | − | − | − | − | − | − | − | − | − | + | − |
| 4 Btub 2-4 + Btub 5-14 $5 \times 10^6$ | 1 | − | − | − | − | − | + | − | + | − | + | + | + |
| | 2 | − | − | − | − | − | + | − | + | − | + | + | + |
| | 3 | − | − | − | − | − | + | − | + | − | + | + | + |
| | 4 | − | − | − | − | − | + | − | + | − | + | + | + |
| 5 Btub 2-4 + Btub 5-14 $5 \times 10^3$ No adjuvant | 1 | − | − | − | − | − | − | − | − | − | − | − | − |
| | 2 | − | − | − | − | − | − | − | − | − | − | + | − |
| | 3 | − | − | − | − | − | − | − | − | − | − | + | − |
| | 4 | − | − | − | − | − | − | − | − | − | − | + | − |

AI = animal inoculation (inoculation of cattle blood into mice);
ELISA = enzyme linked immunosorbent assay;
Pa = Parasitemia monitored with the haematocrit centrifugation technique;
PCR = polymerase chain reaction

TABLE 16

Experimental Design of Cattle Reconstruction Study #2

| Group | Challenge T. brucei brucei Strain UTRO 010297B |
|---|---|
| 1 | $5 \times 10^3$ |
| 2 | $5 \times 10^4$ |
| 3 | $5 \times 10^5$ |
| 4 | $5 \times 10^6$ |

Sixteen female Ankole cattle without previous exposure to trypanosomes were divided into 4 experimental groups. Animals were challenged intravenously via the jugular vein with the doses outlined in Table 16. Blood samples were taken before and after challenge. Parasitemia and PCV were determined using the haematocrit centrifugation technique (HCT). Rectal temperature, general body condition, and behavior of animals were observed every other day.

TABLE 17

Parasitemia and symptoms in challenged Ankole cattle

| Group | Dose | 7-14 days post Challenge Parasitemia | Clinical symptoms |
|---|---|---|---|
| 1 | $5 \times 10^3$ | All animals negative | |
| 2 | $5 \times 10^4$ | 2 animals positive ($<10^5$ parasites/ml blood) | |
| 3 | $5 \times 10^5$ | All animals negative | |
| 4 | $5 \times 10^6$ | All animals positive ($7.9 \times 10^6$ to $6.3 \times 10^7$ parasites/ml blood) | Fever (39.3° C. to 40.7° C.) |

All animals including those that were HCT-negative (groups 1, 2, and 3) showed signs of illness such as weakness, occasional diarrhea and reduction of PCV to below pre-challenge values. The study was terminated 14 days post challenge.

Sporadic T. b. brucei infections were observed with a challenge dose of $5 \times 10^4$, but not with $5 \times 10^3$ or $5 \times 10^5$. The Trypanosoma brucei challenge dose of $5 \times 10^6$ infected all animals within the experimental group. With a challenge dose of $5 \times 10^6$, the results observed in Cattle Reconstruction Study #1 were reproduced. Thus, the present inventors demonstrated that this is a sufficient challenge dose for Ankole cattle to obtain a readout in short experimental trials.

Cattle Immunogenicity Studies

Cattle challenge studies are utilized to identify and establish final antigenic vaccine compositions. 50 mg quantities of each target antigen selected from challenge studies in mice are produced. Cattle challenge studies are conducted to determine the optimum combination and dose of targets that constitute the final vaccine candidate. Surviving cattle from this study will be further monitored, throughout the entire project, for potential adverse affects including autoimmune responses.

Cattle Immunogenicity Study #1

Batches of N. benthamiana plants grown as described herein are inoculated with each construct separately and recombinant virus particles (about 50 mg) representing each target antigen are purified independently. Target antigens are evaluated in cattle challenge studies in pools (Table 18). Pool 1 comprises all selected antigens and is evaluated at different concentrations. Pool 2 comprises target antigens that provided 50% and higher protection during challenge. Pool 3 comprises antigens that provided less than 50% protection upon challenge. Pool 4 comprises peptides that have less than 40% identity to any human tubulin sequences.

TABLE 18

| Cattle Immunogenicity Study #1 | | | |
|---|---|---|---|
| Group | Vaccine (Intramuscular) | Vaccine Dose (μg/dose) | Challenge *T. b. brucei* Strain UTRO 010291B |
| 1 | AlMV | 1000 | $10^6$ |
| 2 | PBS + Adjuvant | — | $10^6$ |
| 3 | Pool1 | 2000 of each | $10^6$ |
| 4 | Pool1 | 1000 of each | $10^6$ |
| 5 | Pool1 | 500 of each | $10^6$ |
| 6 | Pool1 | 250 of each | $10^6$ |
| 7 | Pool2 | 1000 of each | $10^6$ |
| 8 | Pool3 | 1000 of each | $10^6$ |
| 9 | Pool4 | 1000 of each | $10^6$ |
| 10 | Untreated animals | | $10^6$ |

Female Ankole cattle, six in each group, are immunized intramuscularly at day 0, 14 and 28. Serum samples are collected prior to each immunization and before challenge on day 38 for immunogenicity analyses. Samples of blood are also collected for 10 days post challenge to monitor for parasitemia. Animals in Group 8 do not receive any immunization treatment, but are challenged intramuscularly at day 38. Although individual peptides have been shown to provide 100% protection in mice, a single target is not necessarily sufficient for inducing fully protective immunity in cattle. Thus, peptides are evaluated in pools. As an outcome of this study, peptides are identified that are included in final vaccine formulations. The selection may be based on minimum number of peptides with highest protected efficacy.

In addition to efficacy evaluation, cattle from Cattle Immunogenicity Study #1 are kept throughout the entire project and monitored for any potential long-term adverse effects, including autoimmune responses. Serum and milk from these animals are tested in small animal studies for potential immune responses, allergic, reactions, and/or autoimmune reactions.

Cattle Immunogenicity Study #2

Studies are conducted to determine content and/or dose of each target antigen in final vaccine compositions. Additional studies will be conducted to determine suitable adjuvant content and assure safety of the formulations. To conduct these studies, 500 mg quantities of each of the selected targets are prepared.

500 mg of recombinant particles, representing each target identified in Cattle Immunogenicity Study #1 as protective, are purified. Purified particles are pooled in different buffers and analyzed for particle integrity using electron microscopy of virus particles, agarose gel electrophoresis of virus particles, and RT-PCR of viral RNA using primers specific to each target peptide. Formulations are tested for storability and long-term stability in frozen and lyophilized states. Formulations with desirable characteristics are evaluated in cattle in the presence of Alhydrogel in combination with Monophosphoryl Lipid A (MPL) or other adjuvant. Design of study is summarized in Table 19.

TABLE 19

Cattle Immunogenicity Study #2

| Group | Vaccine (Intramuscular) | Challenge T. b. brucei Strain UTRO 010291B intramuscular |
|---|---|---|
| 1 | AlMV | $10^6$ |
| 2 | PBS + Adjuvant | $10^6$ |
| 3 | Formulation 1 | $10^6$ |
| 4 | Formulation 2 | $10^6$ |
| 5 | Formulation 3 | $10^6$ |
| 6 | Formulation 4 | $10^6$ |
| 7 | Formulation 5 | $10^6$ |
| 8 | Formulation 6 | $10^6$ |
| 9 | Untreated animals | $10^6$ |

Female Ankole cattle, six in each group, are immunized intramuscularly at day 0, 14 and 28. Serum samples are collected prior to each immunization and before intramuscular challenge on day 38 for immunogenicity analyses. Samples of blood are also collected for 10 days post challenge to monitor for parasitemia. Animals in Group 9 do not receive any immunization treatment, but are challenged at day 38. The objective of this study is to identify effective vaccine formulations. This study also establishes optimal dosage of each individual target in vaccine formulations.

Cattle Immunogenicity Study #3

In this study, antigen production is optimized, and efficacy of final vaccine formulations against homologous and heterologous variants of African trypanosomiasis is evaluated in cattle challenge studies. 500 mg quantities of each of the selected targets are produced, formulated, and tested for protective efficacy in cattle. Portions of prepared formulations are used to study and establish conditions for storage and distribution.

Following infiltration of plants and target protein accumulation, preliminary bench-top experiments for protein purification are performed at the 5 kg (biomass) scale. Base procedures for recovery of target proteins are established. Several separation techniques are investigated to determine the combination that will permit the highest recovery of product (at least 70%) with the greatest purity (at least 90%). General separation techniques, such as size exclusion chromatography, are used along with specific techniques that are dependent on the target protein. Further optimization may be performed with the following goals in mind: reduce the time of processing, increase process reliability, increase target accumulation and recovery, decrease cost, and minimize environmental and health hazards. Knowledge gained during process development and optimization is utilized for production of kilogram quantities of target antigens. This includes reviewing and adjusting scale-up assumptions, as well as detailing equipment requirements for the production that facilitate rapid, cost-effective scale-up from the laboratory to commercial scale.

Once the target antigens are ready, a formulation that is shown to provide high protection is prepared and evaluated against challenge with homologous and heterologous variants of parasite (Table 20). In addition, protective efficacy of vaccine is tested at different dose regimens (Table 20).

TABLE 20

| Cattle Immunogenicity Study #3 | | | | | |
|---|---|---|---|---|---|
| Group | Vaccine | 1st Dose | 2nd Dose | 3rd Dose | Challenge |
| 1 | AlMV + Alhydrogel | + | + | + | homo |
| 2 | AlMV + Alhydrogel | + | + | + | hetero |
| 3 | PBS + Alhydrogel | + | + | + | homo |
| 4 | Formulation X | + | + | + | homo |
| 5 | Formulation X | + | + | + | hetero |
| 6 | Formulation X | − | + | + | homo |
| 7 | Formulation X | − | − | + | homo |
| 8 | Untreated animals | | | | homo |
| 9 | Untreated animals | | | | homo |

Female Ankole cattle, six in each group, are immunized intramuscularly at day 0, 14 and 28. Serum samples are collected prior to each immunization and before challenge on day 38 for immunogenicity analyses. Samples of blood are also collected for 10 days post challenge to monitor for parasitemia. Animals in Group 9 do not receive any immunization treatment, but are challenged at day 38. The outcome of this study is to establish optimal dose regimens and to determine if vaccines protect against both homologous and heterologous pathogen variants. In addition, processes and methodologies established for bench-scale production (up to 5 kg) are utilized for large-scale (up to 50 kg) production.

Cattle Immunogenicity Study #4

Eighty female Ankole cattle were obtained that have no prior history of exposure to *T. brucei*. Cattle were screened by ELISA against previous exposure to trypanosomes (*T. brucei* and/or *T. congolense*). Negative animals were placed into quarantine at the animal facilities of Makerere University for one month prior to the start of the study.

Female Ankole cattle (approximately 18 months old), six in each group, were immunized at days 0, 14, and 42. All vaccine candidates were administered subcutaneously (1 ml) at two different injection sites in the presence of 100 μl (1 mg/ml) QuilA as adjuvant. The second and third immunization was done similarly (Table 21):

TABLE 21

| Cattle Immunogenicity Study #4 | | | | | |
|---|---|---|---|---|---|
| Group | Vaccine (Subcutaneous) | Injection site nr. | $1^{st}$ Dose (μg/dose) | $2^{nd}$ Dose (μg/dose) | $3^{rd}$ Dose (μg/dose) |
| 1 | AlMV | 1 | 2250 | 2250 | 2250 |
| | AlMV | 2 | 2250 | 2250 | 2250 |
| 2 | Btub2 + | 1 | 750 | 750 | 750 |
| | Btub5 + | | 750 | 750 | 750 |
| | Btub11 | | 750 | 750 | 750 |
| | Btub2 + | 2 | 750 | 750 | 750 |
| | Btub5 + | | 750 | 750 | 750 |
| | Btub11 | | 750 | 750 | 750 |
| 3 | Btub2 | 1 | 1500 | 1500 | 1500 |
| | Btub5 | 2 | 1500 | 1500 | 1500 |
| 4 | Btub2 | 1 | 1500 | 1500 | 1500 |
| | Btub2 | 2 | 1500 | 1500 | 1500 |
| 5 | Btub5 | 1 | 1500 | 1500 | 1500 |
| | Btub5 | 2 | 1500 | 1500 | 1500 |
| 6 | Btub11 | 1 | 1500 | 1500 | 1500 |
| | Btub11 | 2 | 1500 | 1500 | 1500 |
| 7 | Btub1 | 1 | 1500 | 1500 | 1500 |
| | Btub1 | 2 | 1500 | 1500 | 1500 |
| 8 | Btub7 | 1 | 1500 | 1500 | 1500 |
| | Btub7 | 2 | 1500 | 1500 | 1500 |
| 9 | Atub3 | 1 | 1500 | 1500 | 1500 |
| | Atub3 | 2 | 1500 | 1500 | 1500 |
| 10* | clean | | | | |
| 11** | clean | | | | |

*cattle were not vaccinated but challenged

**cattle were neither vaccinated nor challenged

Blood samples (10 ml) were collected via the jugular vein prior to each immunization and before challenge on day 53 and post challenge. Blood samples were used to monitor for parasitaemia, to determine the packed cell volume (PCV), and to obtain sera for immunogenicity assays.

Cattle in groups 1-10 were challenged with $5\times10^6$ *Trypanosoma brucei brucei* parasite (strain UTRO 010291B). Group 11 was not challenged.

The onset of parasitemia and its progression were monitored by the haematocrit centrifugation technique (HCT) (Woo, 1970, *Acta Tropica,* 27:384; incorporated herein by reference) followed by evaluation of the parasite numbers in the buffy coat by the matching method (Herbert and Lumsden, 1976, *Exp. Parasitol.*, 40:427; incorporated herein by reference). Results are presented in Table 22:

TABLE 22

Cattle Immunogenicity Study #4: Average Parasitaemia

| Group | Vaccine | 7 | 11 | 39 | 45 | 52 |
|---|---|---|---|---|---|---|
| | | \multicolumn{5}{c}{Days post challenge} | | | | |
| 1 | AlMV | 1.9* | 6.4 | 4.9 | 0 | 1.7 |
| 2 | Btub2 + 5 + 11 | 2.5 | 7 | 2.3 | 3.3 | 1.2 |
| 3 | Btub2 + 5 | 1.4 | 6 | 3 | 0 | 2.6 |
| 4 | Btub2 | 3.9 | 6 | 2.4 | 1.4 | 0 |
| 5 | Btub5 | 0 | 6.6 | 0 | 0 | 0 |
| 6 | Btub11 | 3.9 | 6.5 | 0 | 0 | 0 |
| 7 | Btub1 | 3 | 6.4 | 4.6 | 1.3 | 0 |
| 8 | Btub7 | 0 | 7.1 | 5 | 0 | 0 |
| 9 | Atub3 | 1 | 6.9 | 6.7 | 3.3 | 2.2 |
| 10 | Clean/Challenge | 2 | 6.1 | 5.4 | 3.9 | 2.6 |
| 11 | Clean/No challenge | 0 | 0 | 0 | 0 | 0 |

*Parasitaemia is given as average of log values at the indicated days post challenge All animals with the exception of those in the clean control (group 11) had parasites in their blood at 11 days post challenge. At 39 days post challenge, the number of cattle containing parasites in the Btub5 (group 5) and Btub11 (group 6) decreased to zero. These cattle remained negative at 45 and 52 days post challenge, suggesting that parasites, if at all present, were below $10^3$ per ml blood.

Acute Phase of Infection: Three cattle died at 11 days post challenge due to weakness that was caused by fights between the animals. Seventeen cattle died between 17 and 34 days post challenge. With the exception of Btub2+5+11, each group lost 1 to 3 animals during this stage (Table 23):

TABLE 23

Cattle Immunogenicity Study #4: Death of cattle 17 to 34 days post challenge

| | AlMV | Btub2 + 5 + 11 | Btub2 + 5 | Btub2 | Btub5 | Btub11 | Btub1 | Btub7 | Atub3 | clean/ challenge |
|---|---|---|---|---|---|---|---|---|---|---|
| Death/Total | 3/6 | 0/5[a] | 3/5[a] | 1/6 | 1/5[a] | 2/6 | 2/6 | 2/6 | 1/6 | 2/6 |

[a]animals died due internal fights

Figure 7A:
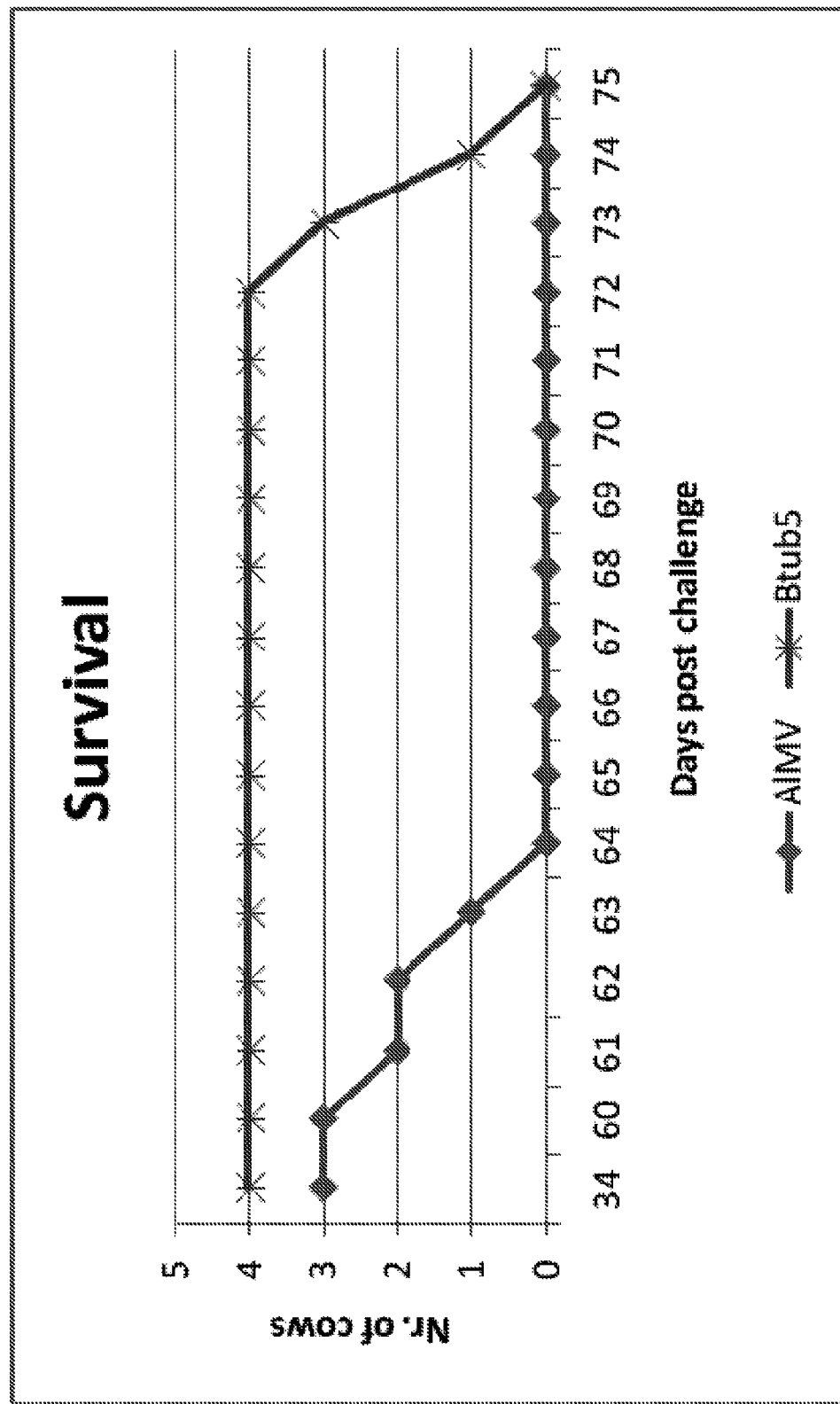
FIG. 7: Survival of tubulin antigen-immunized cattle compared to AlMV-immunized cattle. (A) All three AlMV-immunized cattle died between 61 and 64 days. In contrast, the four Btub 5-14 immunized cattle lived 9 to 11 days longer than the AlMV control. (B) Two of the Btub 2-4+5-14+11-31 immunized cattle lived 7 to 10 days longer than the AlMV control cattle. (C) One of the Btub 11-31 immunized cattle lived 10 days longer than the AlMV control cattle. (D) Two of the Atub 3-17 immunized cattle lived 10 and 11 days longer than the or less than) of the stated reference value unless otherwise stated or otherwise evident from the context (except where such number would exceed 100% of a possible value).
Figure 7B:
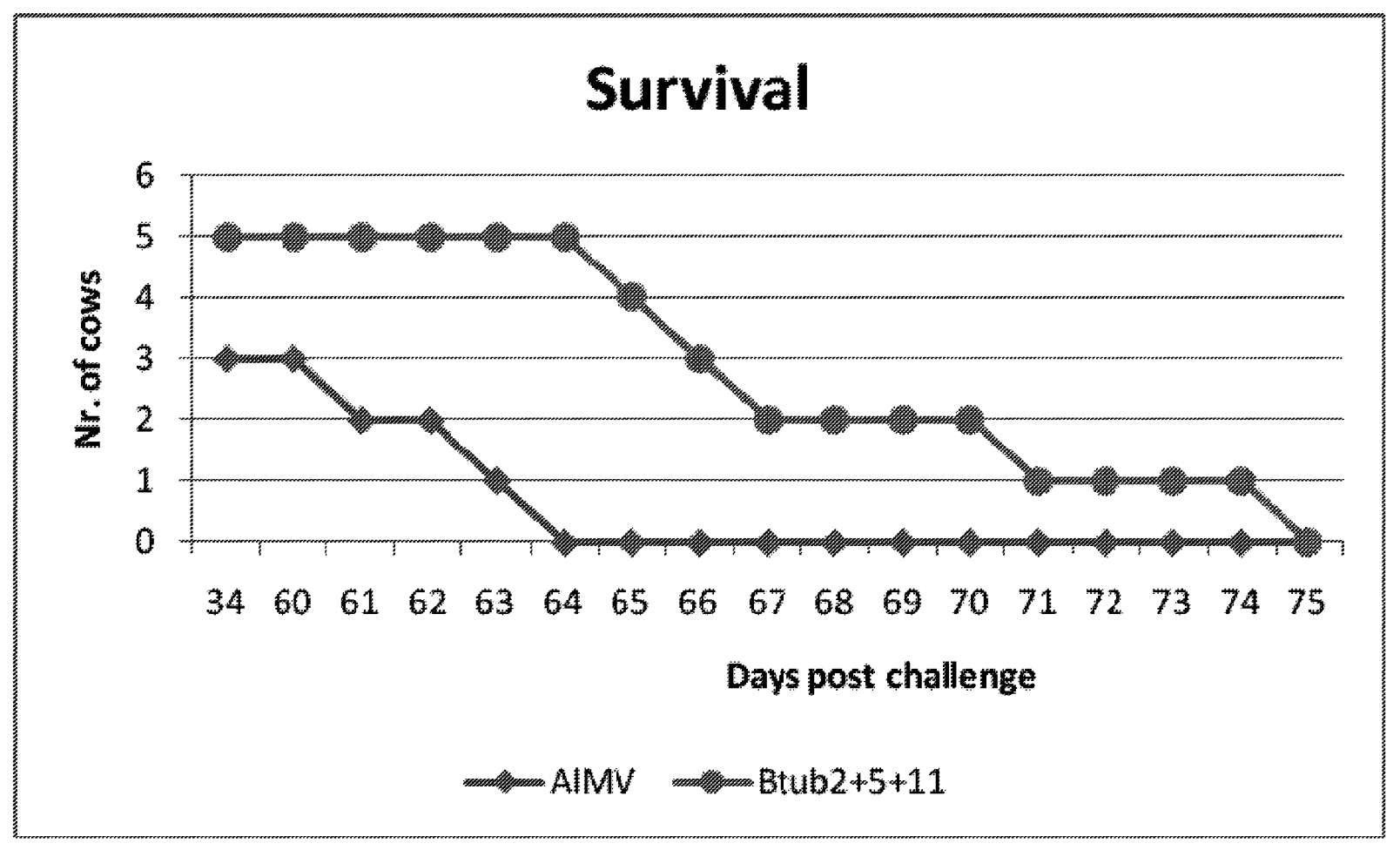
Figure 7C:
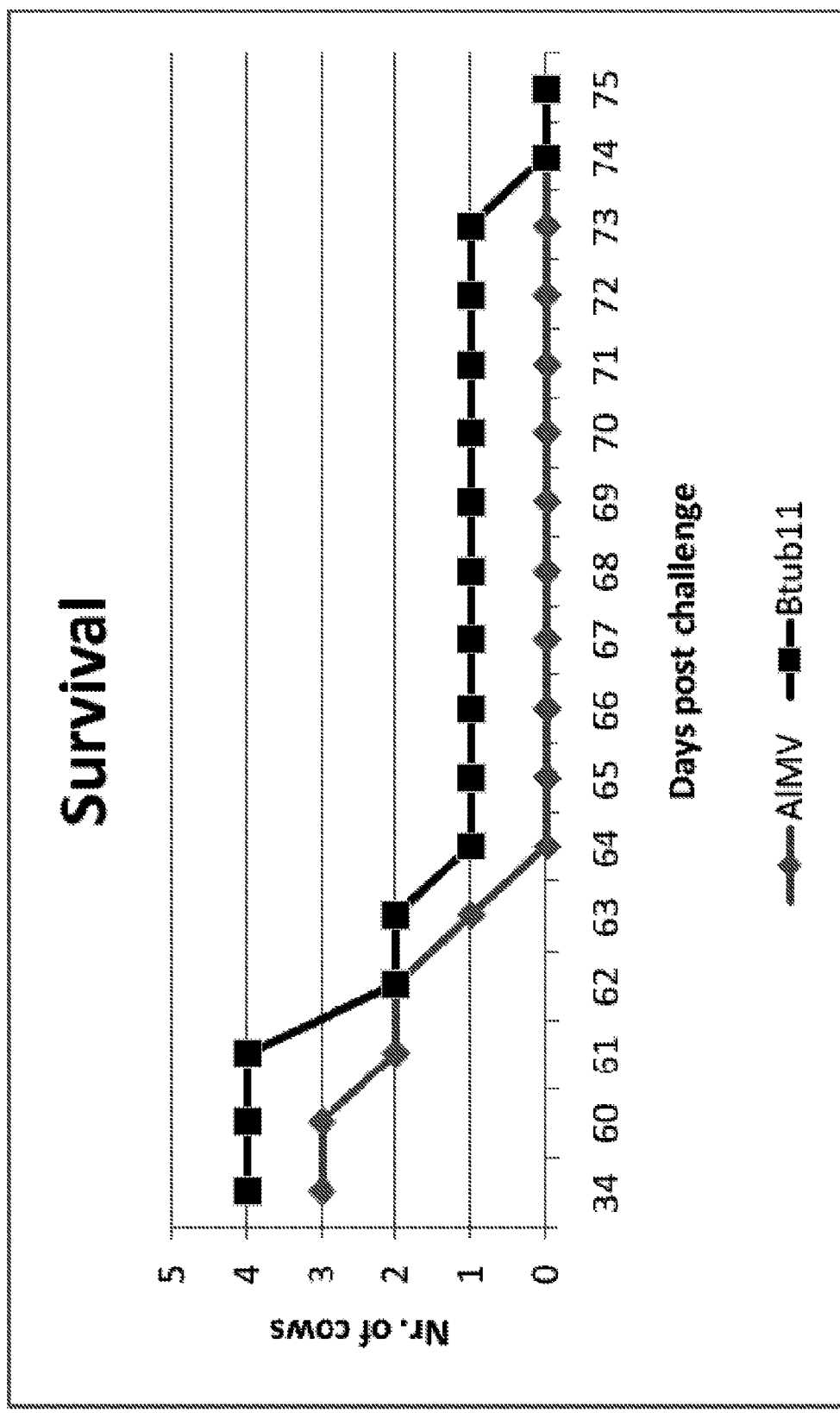
Figure 7D:
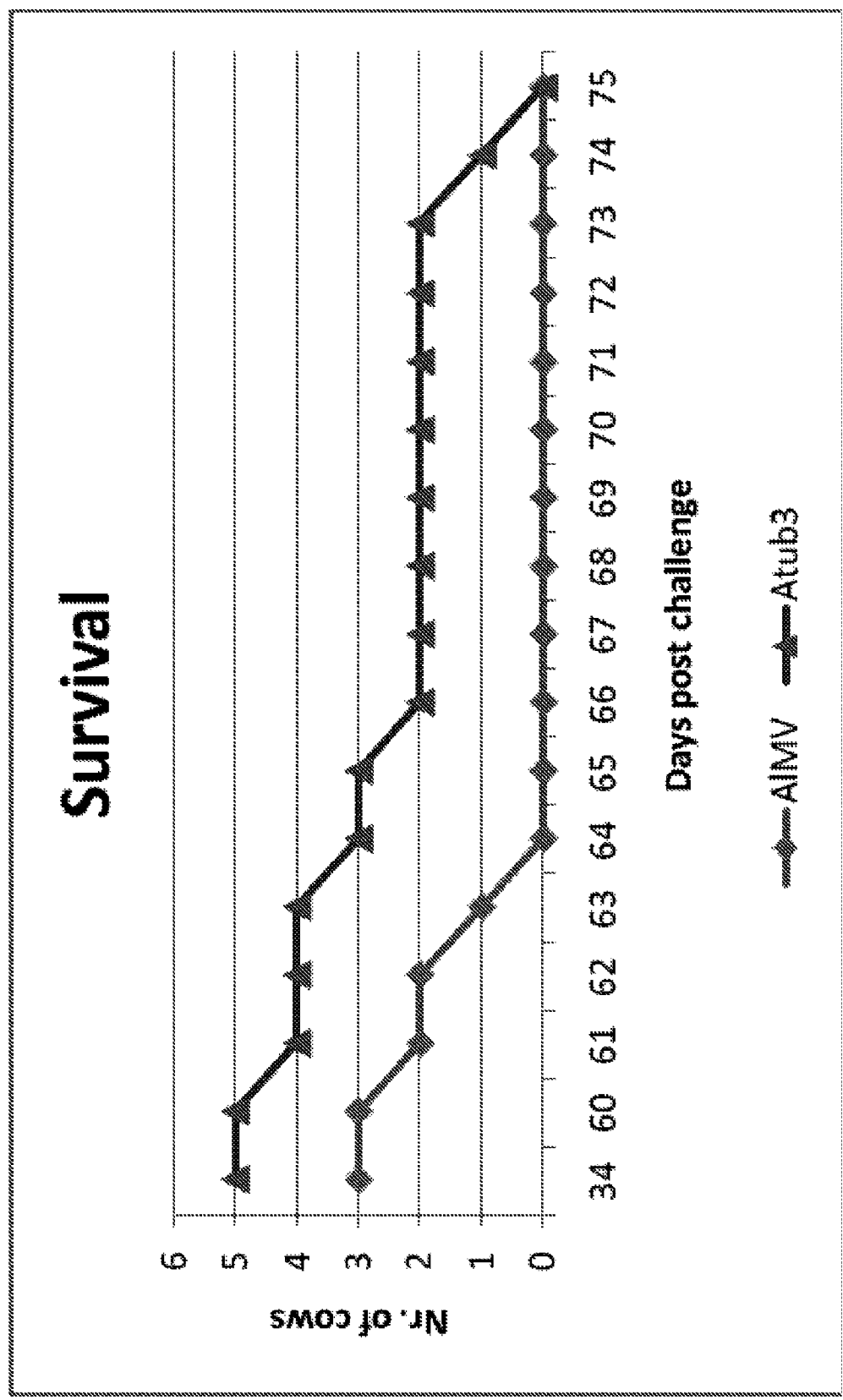

Chronic phase of infection: All AlMV control animals succumbed between 61 and 64 days post challenge. Animals from within the experimental groups also died, however, each of the experimental groups contained one or two animals that lived up to 11 days longer than the controls. Remarkably, all 4 animals immunized with Btub 5 lived 9-11 days longer compared to the AlMV-immunized controls (FIG. 7).

Parasitemia and Survival: All animals were tested at 59 days post challenge for parasitemia in AI (transfer of blood from cattle to mice). The detection limit of AI is 100 Trypanosomes/ml blood. The number of cattle that tested negative in AI is given in Table 24:

TABLE 24

Cattle Immunogenicity Study #4: Parasitemia status in cattle at 59 days post challenge

| | AlMV | Btub2 + 5 + 11 | Btub2 + 5 | Btub2 | Btub5 | Btub11 | Btub1 | Btub7 | Atub3 | clean/ challenge |
|---|---|---|---|---|---|---|---|---|---|---|
| Negative/Total | 0/3 | 1/5 | 0/2 | 0/5 | 2/4 | 1/4 | 1/4 | 2/4 | 3/5 | 0/4 |

Animals that tested negative in AI tended to survive longer compared to those that tested positive in AI (Table 25):

TABLE 25

Cattle Immunogenicity Study #4: Average survival of cattle beyond that of controls

| | AlMV | Btub2 + 5 + 11 | Btub2 + 5 | Btub2 | Btub5 | Btub11 | Btub1 | Btub7 | Atub3 | clean/ challenge |
|---|---|---|---|---|---|---|---|---|---|---|
| Negative | 0 | 10* | 0 | 0 | 9.5 | 10 | 8 | 10.5 | 7.7 ? | 0 |
| Positive | 0 | 3.3 | 3 | 6 | 10 | 0 | 4 | 3 | 0 | 0 |

*average survival is given in days.

Without wishing to be bound by any one particular theory, death during the acute phase of the disease was possibly due to the initial high parasite load. However, parasite numbers in this study decreased faster in immunized compared to the controls animals. Death of animals during the later stages of Trypanosomiasis even in those groups that showed promising or complete recovery from parasites could have been caused by secondary damage of internal organs. *Trypanosoma* infections cause anemia resulting in lack of oxygen supply to organs and muscles. Post mortem examination of diseased animals show that internal organs, muscles and specifically the bone marrow are edematous (very watery).

The sudden death of animals at ~73 days post challenge raises the question as to whether a modification in the diet of animals might have caused additional stress. This modification was necessary because delivery of hay was delayed as a result of the political crisis in the neighbouring country Kenya. The political crisis in Kenya caused fuel shortages, frequent power outages to name only a few of the unpredictable challenges during this trial.

The present inventors observed a reduction and clearance of parasites in cattle that were vaccinated with tubulin subunit candidates but not in control groups. The majority of animals testing negative in AI survived 9-11 days longer compared to the AlMV-immunized control, that tested AI positive. Specifically, immunization with Btub5 appeared to prolong survival of challenged animals.

Cattle Immunogenicity Study #5

Under natural conditions Trypanosomes are transmitted into the host through the bite of a tsetse fly. Thus, the present invention encompasses the recognition that this natural route for *Trypanosoma* infections might be best mimicked via intradermal injection. The following experiments were performed to determine whether an intradermal route is suitable for experimental infection of cattle with trypanosomes.

Twenty-four female Ankole cattle (~15-24 months old) were screened by ELISA and PCR to ensure that there was no pre-existing exposure to Trypanosomes. Animals were randomized into 6 groups of 4 animals each and then challenged with *Trypanosome brucei brucei* (UTRO 010291B) (Table 26). Blood samples were taken prior and post challenges.

TABLE 26

Experimental design of Cattle Immunogenicity Study #5

| Group | Parasite species | Parasite dose | Challenge Route |
|---|---|---|---|
| 1 | T. b. brucei | $10^3$ | Intradermal |
| 2 | T. b. brucei | $10^4$ | Intradermal |
| 3 | T. b. brucei | $10^5$ | Intradermal |
| 4 | T. b. brucei | $10^6$ | Intradermal |
| 5 | T. b. brucei | $10^6$ | Intravenous |
| 6 | T. b. brucei | $10^3$ | Intravenous |

Challenge doses were delivered in a final volume of 800 µl/animal either intravenously via the jugular vein or intradermally into the neck region. Animals were monitored daily for parasitemia development beginning on day 5 post challenge.

Blood samples were subjected to the haematocrit centrifugation technique (HCT) followed by parasite counts after Murray which is a modified darkground/buffy coat procedure (Akol and Murray, 1983, *Exp. Parasitol.*, 55:386; incorporated herein by reference; Table 27). Briefly, the buffy coat zone is recovered from the micro haematocrit capillary tube by cutting the capillary tube to incorporate 1 mm of erythrocytes and 1 mm of plasma. The contents were spread on a glass slide and covered with a 22×22 mm coverslip and examined under a microscope equipped with background illumination.

TABLE 27

Scoring of parasitemia with the Modified Buffy Coat Technique after Murray

| Number of Trypanosomes | Trypanosomes/ml blood | Score |
|---|---|---|
| Swarming > 100 per field | >$10^6$ | 6+ |
| >10 per field | >$10^5$ | 5+ |
| 1-10 per field | $10^4$ to $5 \times 10^5$ | 4+ |
| 1 per 2 fields-1 per 10 fields | $5 \times 10^3$ to $5 \times 10^4$ | 3+ |
| 1-10 per preparation | $10^3$-$10^4$ | 2+ |
| 1 per preparation | $10^2$-$10^3$ | 1+ |

All animals but one in group 1 ($10^3$ *T. b. brucei*/intradermal) showed parasites on day 7 post challenge. Most animals developed fever (rectal temperature>39° C.). PCV values dropped but remained in the normal range of >24%. The experiment was terminated after 14 days.

TABLE 28

Parsitaemia in challenged Ankole cattle

| Group | *Trypanosoma* species | Dose | Route | Cattle # | Days post-challenge | | | |
|---|---|---|---|---|---|---|---|---|
| | | | | | 5 | 6 | 7 | 12[c] |
| 1 | *T. b. brucei* | $10^3$ | Intradermal | A026 | —[a] | — | — | — |
| | | | | A029 | — | — | 4+[b] | 4+ |
| | | | | A003 | — | 1+ | 1+ | 2+ |
| | | | | A025 | — | — | 4+ | 4+ |
| 2 | *T. b. brucei* | $10^4$ | Intradermal | A011 | 1+ | 1+ | 2+ | 2+ |
| | | | | A015 | 1+ | 4+ | 4+ | 4+ |
| | | | | A014 | — | 2+ | 2+ | 2+ |
| | | | | A024 | — | — | 5+ | 5+ |
| 3 | *T. b. brucei* | $10^5$ | Intradermal | A032 | — | 2+ | 2+ | 2+ |
| | | | | A028 | 2+ | 4+ | 4+ | 5+ |
| | | | | A021 | 1+ | 2+ | 2+ | 2+ |
| | | | | A023 | 2+ | 2+ | 2+ | 3+ |
| 4 | *T. b. brucei* | $10^6$ | Intradermal | A031 | 5+ | 5+ | 5+ | 4+ |
| | | | | A027 | 4+ | 5+ | 5+ | 5+ |
| | | | | A020 | 1+ | 1+ | 1+ | 2+ |
| | | | | A002 | 2+ | 2+ | 2+ | 2+ |
| 5 | *T. b. brucei* | $10^6$ | Intravenous | A009 | — | 4+ | 4+ | 4+ |
| | | | | A017 | — | — | 3+ | 3+ |
| | | | | A016 | 5+ | 5+ | 5+ | 4+ |
| | | | | A010 | 5+ | 5+ | 4+ | 5+ |
| 6 | *T. b. brucei* | $10^3$ | Intravenous | A012 | 4+ | 4+ | 5+ | 4+ |
| | | | | A004 | 1+ | 2+ | 3+ | 2+ |
| | | | | A008 | — | — | 4+ | 4+ |
| | | | | A018 | 2+ | 5+ | 4+ | 4+ |

[a] no parasites detected by Buffy coat examinations
[b] For interpretation of Scorings refer to Table 2
[c] Days between 7 and 11 were omitted from the Table because no significant changes occurred during this time

TABLE 29

Average parasitemia 12 days post challenge

| Group | *Trypanosoma* species | Dose | Route | Cattle | 12 days post challenge |
|---|---|---|---|---|---|
| 1 | *T. b. brucei* | $10^3$ | Intradermal | 4 | 3.3+ |
| 2 | *T. b. brucei* | $10^4$ | Intradermal | 4 | 3.25+ |
| 3 | *T. b. brucei* | $10^5$ | Intradermal | 4 | 3+ |
| 4 | *T. b. brucei* | $10^6$ | Intradermal | 4 | 3.25+ |
| 5 | *T. b. brucei* | $10^6$ | Intravenous | 4 | 4+ |
| 6 | *T. b. brucei* | $10^3$ | Intravenous | 4 | 3.5+ |

Blood samples from earlier studies are tested with the improved parasitological method after Murray et al. (1983) to judge on increase in sensitivity.

Cattle Immunogenicity Study #5 demonstrated that intradermal administration of challenge doses was as effective as intravenous administration.

Cattle Immunogenicity Study #6

Another immunogenicity study is performed according to the experimental plan presented in Table 30:

TABLE 30

Experimental Plan for Sixth Cattle Immunogenicity Study

| Groups | Ankole female | Vaccine Subcutaneous | Injection sites | 1st Dose (μg/dose) | 2nd Dose (μg/dose) | 3rd Dose (μg/dose) | Challenge *T. brucei brucei* strain UTRO 010291B intravenous |
|---|---|---|---|---|---|---|---|
| 1 | 10 | Btub5 + QuilA | Leg 1 | 1500 | 1500 | 1500 | $5 \times 10^3$ |
| | | Btub5 + QuilA | Leg 2 | 1500 | 1500 | 1500 | |
| 2 | 10 | Btub5 + QuilA | Leg 1 | 1500 | 1500 | 1500 | $5 \times 10^4$ |
| | | Btub5 + QuilA | Leg 2 | 1500 | 1500 | 1500 | |
| 3 | 10 | Btub5 + QuilA | Leg 1 | 1500 | 1500 | 1500 | $5 \times 10^5$ |
| | | Btub5 + QuilA | Leg 2 | 1500 | 1500 | 1500 | |
| 4 | 10 | Btub5 + QuilA + Alhydrogel | Leg 1 | 1500 | 1500 | 1500 | $5 \times 10^3$ |
| | | Btub5 + QuilA + Alhydrogel | Leg 2 | 1500 | 1500 | 1500 | |
| 5 | 10 | Btub5 + QuilA + Alhydrogel | Leg 1 | 1500 | 1500 | 1500 | $5 \times 10^4$ |
| | | Btub5 + QuilA + Alhydrogel | Leg 2 | 1500 | 1500 | 1500 | |
| 6 | 10 | clean | Leg 1 | Buffer | Buffer | Buffer | $5 \times 10^3$ |
| | | clean | Leg 2 | Buffer | Buffer | Buffer | |
| 7 | 10 | clean | Leg 1 | Buffer | Buffer | Buffer | $5 \times 10^4$ |
| | | clean | Leg 2 | Buffer | Buffer | Buffer | |
| 8 | 10 | clean | Leg 1 | Buffer | Buffer | Buffer | $5 \times 10^5$ |
| | | clean | Leg 2 | Buffer | Buffer | Buffer | |
| 9 | 6 | Clean | | | | | No challenge |
| | | Clean | | | | | |

Total volume per injection is 1 ml of immunogen plus 100 μl QuilA (1 mg/ml). Compositions with Alhydrogel alone (i.e., not in the presence of QuilA) are also tested.

TABLE 31

Vaccination schedule and collection of sera for cattle study #6

| 1st Bleed | 1st Dose | 2nd Bleed | 2nd Dose | 3rd Bleed | 3rd Dose | 4th Bleed | Challenge |
|---|---|---|---|---|---|---|---|
| −4 days | Day 0 | Day 10 | Day 14 | Day 24 | Day 28 | Day 34 | Day 38 |

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any *Trypanosoma* species or strain; any *Trypanosoma* protein; any fusion protein; any expression system; any plant production system; any method of administration; etc.) can be excluded from any one or more claims, for any reason, whether or not related to the existence of prior art.

What is claimed is:

1. An isolated antigen comprising a component of a *Trypanosoma* protein fused to alfalfa mosaic virus (AlMV) coat protein;
wherein the *Trypanosoma* protein component is a fragment of alpha tubulin or a fragment of beta tubulin consisting of one or more amino acid sequences selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20.

2. The isolated antigen of claim 1, wherein the *Trypanosoma* protein component is a polytope.

3. The isolated antigen of claim 1, wherein the *Trypanosoma* protein component consists of at least two sequences selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20.

4. The isolated antigen of claim 3, wherein the *Trypanosoma* protein component consists of a portion of alpha tubulin selected from the group consisting of SEQ ID NO:4, SEQ ID NO:5, SEQ ID NO:6, SEQ ID NO:7, SEQ ID NO:9, SEQ ID NO:10, and SEQ ID NO:11 and a portion of beta tubulin selected from the group consisting of SEQ ID NO:12, SEQ ID NO:13, SEQ ID NO:14, SEQ ID NO:16, SEQ ID NO:18, SEQ ID NO:19, and SEQ ID NO:20,
 a plurality of portions of alpha tubulin selected from the group consisting of SEQ ID NO:4, SEQ ID NO:5, SEQ ID NO:6, SEQ ID NO:7, SEQ ID NO:9, SEQ ID NO:10, and SEQ ID NO:11, or
 a plurality of portions of beta tubulin selected from the group consisting of SEQ ID NO:12, SEQ ID NO:13, SEQ ID NO:14, SEQ ID NO:16, SEQ ID NO:18, SEQ ID NO:19, and SEQ ID NO:20.

5. A composition comprising a pharmaceutically acceptable carrier and a first antigen comprising a component of a *Trypanosoma* protein fused to AlMV coat protein;
 wherein the *Trypanosoma* protein component is a fragment of alpha tubulin or a fragment of beta tubulin consisting of one or more amino acid sequences selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20; and
 wherein the composition is capable of eliciting an immune response upon administration to a subject.

6. The composition of claim 5, wherein the *Trypanosoma* protein component consists of at least two domains selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20.

7. The composition of claim 6, wherein the *Trypanosoma* protein component consists of at least one portion of alpha tubulin selected from the group consisting of SEQ ID NO:4, SEQ ID NO:5, SEQ ID NO:6, SEQ ID NO:7, SEQ ID NO:9, SEQ ID NO:10, and SEQ ID NO:11 and at least one portion of beta tubulin selected from the group consisting of SEQ ID NO:12, SEQ ID NO:13, SEQ ID NO:14, SEQ ID NO:16, SEQ ID NO:18, SEQ ID NO:19, and SEQ ID NO:20,
 a plurality of portions of alpha tubulin selected from the group consisting of SEQ ID NO:4, SEQ ID NO:5, SEQ ID NO:6, SEQ ID NO:7, SEQ ID NO:9, SEQ ID NO:10, and SEQ ID NO:11, or
 a plurality of portions of beta tubulin selected from the group consisting of SEQ ID NO:12, SEQ ID NO:13, SEQ ID NO:14, SEQ ID NO:16, SEQ ID NO:18, SEQ ID NO:19, and SEQ ID NO:20.

8. The composition of claim 5, further comprising a second antigen, wherein the second antigen comprises a component of a *Trypanosoma* protein fused to a thermostable protein or fused to AlMV coat protein,
 wherein the *Trypanosoma* protein component of the second antigen is distinct from the first antigen and is selected from the group consisting of a fragment of alpha tubulin having the sequence set forth in SEQ ID NO:4, SEQ ID NO:5, SEQ ID NO:6, SEQ ID NO:7, SEQ ID NO:9, SEQ ID NO:10, or SEQ ID NO:11 and a fragment of beta tubulin having the sequence set forth in SEQ ID NO:12, SEQ ID NO:13, SEQ ID NO:14, SEQ ID NO:16, SEQ ID NO:18, SEQ ID NO:19, or SEQ ID NO:20; and
 wherein the composition is capable of eliciting an immune response upon administration to a subject.

9. The composition of claim 5, wherein the antigen is produced in a plant selected from a transgenic plant and a plant transiently expressing the antigen.

10. The composition of claim 5, wherein the composition comprises antigen which is purified, partially purified, or unpurified from plant cells, a plant, seeds, fruit, or an extract thereof.

11. A composition comprising at least two antigens, each of which comprises a component of a *Trypanosoma* protein, wherein the *Trypanosoma* protein components each consist of an amino acid sequence selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20;
 wherein at least one of the antigens is fused to AlMV coat protein;
 wherein the composition comprises a pharmaceutically acceptable carrier; and
 wherein the composition is capable of eliciting an immune response upon administration to a subject.

12. A method for inducing an immune response against *Trypanosoma* infection in a subject comprising administering to a subject an effective amount of an anti-*Trypanosoma* composition, wherein the administration is sufficient to stimulate production of antigen specific antibodies or stimulate a cellular immune response by the subject; thereby inducing an immune response;
 wherein the composition comprises an antigen comprising a component of a *Trypanosoma* protein fused to AlMV coat protein; and
 wherein the *Trypanosoma* protein component is a fragment of alpha tubulin or a fragment of beta tubulin consisting of one or more amino acid sequences selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20.

13. An isolated antigen comprising a component of a *Trypanosoma* protein fused to a thermostable protein;
 wherein the *Trypanosoma* protein component is a fragment of alpha tubulin or a fragment of beta tubulin consisting of an amino acid sequence selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20.

14. The isolated antigen of claim 13, wherein the *Trypanosoma* protein component is a polytope.

15. The isolated antigen of claim 13, wherein the *Trypanosoma* protein component consists of at least two sequences selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20.

16. The isolated antigen of claim 15, wherein the *Trypanosoma* protein component consists of a portion of alpha tubulin selected from the group consisting of SEQ ID NO:4, SEQ ID NO:5, SEQ ID NO:6, SEQ ID NO:7, SEQ ID NO:9, SEQ ID NO:10, and SEQ ID NO:11 and a portion of beta tubulin selected from the group consisting of SEQ ID NO:12, SEQ ID NO:13, SEQ ID NO:14, SEQ ID NO:16, SEQ ID NO:18, SEQ ID NO:19, and SEQ ID NO:20,
   a plurality of portions of alpha tubulin selected from the group consisting of SEQ ID NO:4, SEQ ID NO:5, SEQ ID NO:6, SEQ ID NO:7, SEQ ID NO:9, SEQ ID NO:10, and SEQ ID NO:11, or
   a plurality of portions of beta tubulin selected from the group consisting of SEQ ID NO:12, SEQ ID NO:13, SEQ ID NO:14, SEQ ID NO:16, SEQ ID NO:18, SEQ ID NO:19, and SEQ ID NO:20.

17. A composition comprising a pharmaceutically acceptable carrier and a first antigen comprising a component of a *Trypanosoma* protein fused to a thermostable protein;
   wherein the *Trypanosoma* protein component consists of one or more fragments of alpha tubulin or beta tubulin selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20; and
   wherein the composition is capable of eliciting an immune response upon administration to a subject.

18. The composition of claim 17, wherein the *Trypanosoma* protein component consists of at least two domains selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20.

19. The composition of claim 18, wherein the *Trypanosoma* protein component consists of at least one portion of alpha tubulin selected from the group consisting of SEQ ID NO:4, SEQ ID NO:5, SEQ ID NO:6, SEQ ID NO:7, SEQ ID NO:9, SEQ ID NO:10, and SEQ ID NO:11 and at least one portion of beta tubulin selected from the group consisting of SEQ ID NO:12, SEQ ID NO:13, SEQ ID NO:14, SEQ ID NO:16, SEQ ID NO:18, SEQ ID NO:19, and SEQ ID NO:20,
   a plurality of portions of alpha tubulin selected from the group consisting of SEQ ID NO:4, SEQ ID NO:5, SEQ ID NO:6, SEQ ID NO:7, SEQ ID NO:9, SEQ ID NO:10, and SEQ ID NO:11, or
   a plurality of portions of beta tubulin selected from the group consisting of SEQ ID NO:12, SEQ ID NO:13, SEQ ID NO:14, SEQ ID NO:16, SEQ ID NO:18, SEQ ID NO:19, and SEQ ID NO:20.

20. The composition of claim 17, further comprising a second antigen, wherein the second antigen comprises a component of a *Trypanosoma* protein fused to a thermostable protein or fused to AlMV coat protein and a pharmaceutically acceptable carrier;
   wherein the *Trypanosoma* protein component of the second antigen is distinct from the first antigen and is selected from the group consisting of a fragment of alpha tubulin having the sequence set forth in SEQ ID NO:4, SEQ ID NO:5, SEQ ID NO:6, SEQ ID NO:7, SEQ ID NO:9, SEQ ID NO:10, or SEQ ID NO:11 and a fragment of beta tubulin having the sequence set forth in SEQ ID NO:12, SEQ ID NO:13, SEQ ID NO:14, SEQ ID NO:16, SEQ ID NO:18, SEQ ID NO:19, or SEQ ID NO:20; and
   wherein the composition is capable of eliciting an immune response upon administration to a subject.

21. The composition of claim 17, wherein the antigen is produced in a plant selected from a transgenic plant and a plant transiently expressing the antigen.

22. The composition of claim 17, wherein the composition comprises antigen which is purified, partially purified, or unpurified from plant cells, a plant, seeds, fruit, or an extract thereof.

23. A method for inducing an immune response against *Trypanosoma* infection in a subject comprising administering to a subject an effective amount of an anti-*Trypanosoma* composition, wherein the administration is sufficient to stimulate production of antigen specific antibodies or stimulate a cellular immune response by the subject; thereby inducing an immune response;
   wherein the composition comprises an antigen comprising a component of a *Trypanosoma* protein fused to a thermostable protein; and
   wherein the *Trypanosoma* protein component is a fragment of alpha tubulin or a fragment of beta tubulin consisting of an amino acid sequence selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:16, SEQ ID NO:18, SEQ ID NO:19, and SEQ ID NO:20.

* * * * *

UNITED STATES PATENT AND TRADEMARK OFFICE
CERTIFICATE OF CORRECTION

| | |
|---|---|
| PATENT NO. | : 8,778,348 B2 |
| APPLICATION NO. | : 12/110877 |
| DATED | : July 15, 2014 |
| INVENTOR(S) | : Elisabeth Knapp et al. |

It is certified that error appears in the above-identified patent and that said Letters Patent is hereby corrected as shown below:

In the Specification:

Column 1, line 9, delete "2008 2007" and insert -- 2007 --, therefor.

Signed and Sealed this
Seventeenth Day of May, 2016

Michelle K. Lee
*Director of the United States Patent and Trademark Office*

SEQUENCE LISTING

```
<160> NUMBER OF SEQ ID NOS: 42

<210> SEQ ID NO 1
<211> LENGTH: 451
<212> TYPE: PRT
<213> ORGANISM: Trypanosoma brucei

<400> SEQUENCE: 1

Met Arg Glu Ala Ile Cys Ile His Ile Gly Gln Ala Gly Cys Gln Val
 1               5                  10                  15

Gly Asn Ala Cys Trp Glu Leu Phe Cys Leu Glu His Gly Ile Gln Pro
            20                  25                  30

Asp Gly Ala Met Pro Ser Asp Lys Thr Ile Gly Val Glu Asp Asp Ala
        35                  40                  45

Phe Asn Thr Phe Phe Ser Glu Thr Gly Ala Gly Lys His Val Pro Arg
    50                  55                  60
```

```
Ala Val Phe Leu Asp Leu Glu Pro Thr Val Asp Glu Val Arg Thr
 65                  70                  75                  80

Gly Thr Tyr Arg Gln Leu Phe His Pro Glu Gln Leu Ile Ser Gly Lys
             85                  90                  95

Glu Asp Ala Ala Asn Asn Tyr Ala Arg Gly His Tyr Thr Ile Gly Lys
            100                 105                 110

Glu Ile Val Asp Leu Cys Leu Asp Arg Ile Arg Lys Leu Ala Asp Asn
        115                 120                 125

Cys Thr Gly Leu Gln Gly Phe Leu Val Tyr His Ala Val Gly Gly Gly
    130                 135                 140

Thr Gly Ser Gly Leu Gly Ala Leu Leu Leu Glu Arg Leu Ser Val Asp
145                 150                 155                 160

Tyr Gly Lys Lys Ser Lys Leu Gly Tyr Thr Val Tyr Pro Ser Pro Gln
                165                 170                 175

Val Ser Thr Ala Val Val Glu Pro Tyr Asn Ser Val Leu Ser Thr His
            180                 185                 190

Ser Leu Leu Glu His Thr Asp Val Ala Ala Met Leu Asp Asn Glu Ala
        195                 200                 205

Ile Tyr Asp Leu Thr Arg Arg Asn Leu Asp Ile Glu Arg Pro Thr Tyr
    210                 215                 220

Thr Asn Leu Asn Arg Leu Ile Gly Gln Val Val Ser Ser Leu Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Val Leu Thr Ser Tyr
            260                 265                 270

Ala Pro Val Ile Ser Ala Glu Lys Ala Tyr His Glu Gln Leu Ser Val
        275                 280                 285

Ser Glu Ile Ser Asn Ala Val Phe Glu Pro Ala Ser Met Met Thr Lys
    290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
                325                 330                 335

Thr Lys Arg Thr Ile Gln Phe Val Asp Trp Ser Pro Thr Gly Phe Lys
            340                 345                 350

Cys Gly Ile Asn Tyr Gln Pro Pro Thr Val Val Pro Gly Gly Asp Leu
        355                 360                 365

Ala Lys Val Gln Arg Ala Val Cys Met Ile Ala Asn Ser Thr Ala Ile
    370                 375                 380

Ala Glu Val Phe Ala Arg Ile Asp His Lys Phe Asp Leu Met Tyr Ser
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
            420                 425                 430

Glu Glu Val Gly Ala Glu Ser Ala Asp Met Asp Gly Glu Glu Asp Val
    435                 440                 445

Glu Glu Tyr
    450

<210> SEQ ID NO 2
<211> LENGTH: 442
```

<212> TYPE: PRT
<213> ORGANISM: Trypanosoma brucei

<400> SEQUENCE: 2

Met Arg Glu Ile Val Cys Val Gln Ala Gly Gln Cys Gly Asn Gln Ile
1               5                   10                  15

Gly Ser Lys Phe Trp Glu Val Ile Ser Asp Glu His Gly Val Asp Pro
            20                  25                  30

Thr Gly Thr Tyr Gln Gly Asp Ser Asp Leu Gln Leu Glu Arg Ile Asn
        35                  40                  45

Val Tyr Phe Asp Glu Ala Thr Gly Gly Arg Tyr Val Pro Arg Ser Val
    50                  55                  60

Leu Ile Asp Leu Glu Pro Gly Thr Met Asp Ser Val Arg Ala Gly Pro
65                  70                  75                  80

Tyr Gly Gln Ile Phe Arg Pro Asp Asn Phe Ile Phe Gly Gln Ser Gly
                85                  90                  95

Ala Gly Asn Asn Trp Ala Lys Gly His Tyr Thr Glu Gly Ala Glu Leu
            100                 105                 110

Ile Asp Ser Val Leu Asp Val Cys Cys Lys Glu Ala Glu Ser Cys Asp
        115                 120                 125

Cys Leu Gln Gly Phe Gln Ile Cys His Ser Leu Gly Gly Thr Gly
    130                 135                 140

Ser Gly Met Gly Thr Leu Leu Ile Ser Lys Leu Arg Glu Gln Tyr Pro
145                 150                 155                 160

Asp Arg Ile Met Met Thr Phe Ser Ile Ile Pro Ser Pro Lys Val Ser
                165                 170                 175

Asp Thr Val Val Glu Pro Tyr Asn Thr Thr Leu Ser Val His Gln Leu
            180                 185                 190

Val Glu Asn Ser Asp Glu Ser Met Cys Ile Asp Asn Gly Ala Leu Tyr
        195                 200                 205

Asp Ile Cys Phe Arg Thr Leu Lys Leu Thr Thr Pro Thr Phe Gly Asp
    210                 215                 220

Leu Asn His Leu Val Ser Ala Val Ser Gly Val Thr Cys Cys Leu
225                 230                 235                 240

Arg Phe Pro Gly Gln Leu Asn Ser Asp Leu Arg Lys Leu Ala Val Asn
                245                 250                 255

Leu Val Pro Phe Pro Arg Leu His Phe Phe Met Met Gly Phe Ala Pro
            260                 265                 270

Leu Thr Ser Arg Gly Ser Gln Gln Tyr Arg Gly Leu Ser Val Pro Glu
        275                 280                 285

Leu Thr Gln Gln Met Phe Asp Ala Lys Asn Met Met Gln Ala Ala Asp
    290                 295                 300

Pro Arg His Gly Arg Tyr Leu Thr Ala Ser Ala Leu Phe Arg Gly Arg
305                 310                 315                 320

Met Ser Thr Lys Glu Val Asp Glu Gln Met Leu Asn Val Gln Asn Lys
                325                 330                 335

Asn Ser Ser Tyr Phe Ile Glu Trp Ile Pro Asn Asn Ile Lys Ser Ser
            340                 345                 350

Val Cys Asp Ile Pro Pro Lys Gly Leu Lys Met Ala Val Thr Phe Ile
        355                 360                 365

Gly Asn Asn Thr Cys Ile Gln Glu Met Phe Arg Arg Val Gly Glu Gln
    370                 375                 380

Phe Thr Leu Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
            405                 410                 415

Asp Leu Val Ser Glu Tyr Gln Gln Tyr Gln Asp Ala Thr Ile Glu Glu
            420                 425                 430

Glu Gly Glu Phe Asp Glu Glu Glu Gln Tyr
        435                 440

<210> SEQ ID NO 3
<211> LENGTH: 85
<212> TYPE: PRT
<213> ORGANISM: Trypanosoma brucei

<400> SEQUENCE: 3

Ala Arg Ala Thr Ala Val Pro Lys Lys Ala Val Ala Lys Lys Ala Ala
1               5                   10                  15

Pro Lys Lys Thr Val Ala Lys Lys Ala Ala Pro Lys Lys Ala Val Ala
            20                  25                  30

Lys Lys Val Ala Pro Lys Ala Val Ala Lys Lys Val Val Ala Lys
            35                  40              45

Lys Ala Val Ala Lys Lys Val Val Ala Lys Lys Val Ala Pro Lys Lys
50                  55                  60

Val Val Ala Lys Lys Val Ala Pro Lys Lys Val Ala Gly Lys Lys Ala
65                  70                  75                  80

Ala Ala Lys Lys Ala
            85

<210> SEQ ID NO 4
<211> LENGTH: 18
<212> TYPE: PRT
<213> ORGANISM: Trypanosoma brucei

<400> SEQUENCE: 4

Arg Glu Ala Ile Cys Ile His Ile Gly Gln Ala Gly Cys Gln Val Gly
1               5                   10                  15

Asn Ala

<210> SEQ ID NO 5
<211> LENGTH: 14
<212> TYPE: PRT
<213> ORGANISM: Trypanosoma brucei

<400> SEQUENCE: 5

Thr Gly Ser Gly Leu Gly Ala Leu Leu Leu Glu Arg Leu Ser
1               5                   10

<210> SEQ ID NO 6
<211> LENGTH: 24
<212> TYPE: PRT
<213> ORGANISM: Trypanosoma brucei

<400> SEQUENCE: 6

Tyr Asn Ser Val Leu Ser Thr His Ser Leu Leu Glu His Thr Asp Val
1               5                   10                  15

Ala Ala Met Leu Asp Asn Glu Ala
            20

<210> SEQ ID NO 7
<211> LENGTH: 15
<212> TYPE: PRT
<213> ORGANISM: Trypanosoma brucei -continued

<400> SEQUENCE: 7

Asn Arg Leu Ile Gly Gln Val Val Ser Ser Leu Thr Ala Ser Leu
1               5                   10                  15

<210> SEQ ID NO 8
<211> LENGTH: 14
<212> TYPE: PRT
<213> ORGANISM: Trypanosoma brucei

<400> SEQUENCE: 8

Ile His Phe Val Leu Thr Ser Tyr Ala Pro Val Ile Ser Ala
1               5                   10

<210> SEQ ID NO 9
<211> LENGTH: 21
<212> TYPE: PRT
<213> ORGANISM: Trypanosoma brucei

<400> SEQUENCE: 9

Leu Ser Val Ser Glu Ile Ser Asn Ala Val Phe Glu Pro Ala Ser Met
1               5                   10                  15

Met Thr Lys Cys Asp
            20

<210> SEQ ID NO 10
<211> LENGTH: 18
<212> TYPE: PRT
<213> ORGANISM: Trypanosoma brucei

<400> SEQUENCE: 10

Asp Val Asn Ala Ala Val Ala Thr Ile Lys Thr Lys Arg Thr Ile Gln
1               5                   10                  15

Phe Val

<210> SEQ ID NO 11
<211> LENGTH: 20
<212> TYPE: PRT
<213> ORGANISM: Trypanosoma brucei

<400> SEQUENCE: 11

Val Cys Met Ile Ala Asn Ser Thr Ala Ile Ala Glu Val Phe Ala Arg
1               5                   10                  15

Ile Asp His Lys
            20

<210> SEQ ID NO 12
<211> LENGTH: 18
<212> TYPE: PRT
<213> ORGANISM: Trypanosoma brucei

<400> SEQUENCE: 12

Asp Glu His Gly Val Asp Pro Thr Gly Thr Tyr Gln Gly Asp Ser Asp
1               5                   10                  15

Leu Gln

<210> SEQ ID NO 13
<211> LENGTH: 9
<212> TYPE: PRT
<213> ORGANISM: Trypanosoma brucei

<400> SEQUENCE: 13

Pro Arg Ser Val Leu Ile Asp Leu Glu
1               5

<210> SEQ ID NO 14
<211> LENGTH: 13
<212> TYPE: PRT
<213> ORGANISM: Trypanosoma brucei

<400> SEQUENCE: 14

Ser Val Arg Ala Gly Pro Tyr Gly Gln Ile Phe Arg Pro
1               5                   10

<210> SEQ ID NO 15
<211> LENGTH: 23
<212> TYPE: PRT
<213> ORGANISM: Trypanosoma brucei

<400> SEQUENCE: 15

Leu Leu Ile Ser Lys Leu Arg Glu Gln Tyr Pro Asp Arg Ile Met Met
1               5                   10                  15

Thr Phe Ser Ile Ile Pro Ser
            20

<210> SEQ ID NO 16
<211> LENGTH: 14
<212> TYPE: PRT
<213> ORGANISM: Trypanosoma brucei

<400> SEQUENCE: 16

His Gln Leu Val Glu Asn Ser Asp Glu Ser Met Cys Ile Asp
1               5                   10

<210> SEQ ID NO 17
<211> LENGTH: 12
<212> TYPE: PRT
<213> ORGANISM: Trypanosoma brucei

<400> SEQUENCE: 17

Val Ser Ala Val Val Ser Gly Val Thr Cys Cys Leu
1               5                   10

<210> SEQ ID NO 18
<211> LENGTH: 11
<212> TYPE: PRT
<213> ORGANISM: Trypanosoma brucei

<400> SEQUENCE: 18

Gln Tyr Arg Gly Leu Ser Val Pro Glu Leu Thr
1               5                   10

<210> SEQ ID NO 19
<211> LENGTH: 17
<212> TYPE: PRT
<213> ORGANISM: Trypanosoma brucei

<400> SEQUENCE: 19

Ser Tyr Phe Ile Glu Trp Ile Pro Asn Asn Ile Lys Ser Ser Val Cys
1               5                   10                  15

Asp

<210> SEQ ID NO 20
<211> LENGTH: 12
<212> TYPE: PRT
<213> ORGANISM: Trypanosoma brucei

```
<400> SEQUENCE: 20

Pro Pro Lys Gly Leu Lys Met Ala Val Thr Phe Ile
1               5                   10

<210> SEQ ID NO 21
<211> LENGTH: 20
<212> TYPE: PRT
<213> ORGANISM: Trypanosoma brucei

<400> SEQUENCE: 21

Asn Thr Cys Ile Gln Glu Met Phe Arg Arg Val Gly Glu Gln Phe Thr
1               5                   10                  15

Leu Met Phe Arg
            20

<210> SEQ ID NO 22
<211> LENGTH: 15
<212> TYPE: PRT
<213> ORGANISM: Trypanosoma brucei

<400> SEQUENCE: 22

Asp Ala Thr Ile Glu Glu Glu Gly Glu Phe Asp Glu Glu Glu Gln
1               5                   10                  15

<210> SEQ ID NO 23
<211> LENGTH: 25
<212> TYPE: PRT
<213> ORGANISM: Trypanosoma brucei

<400> SEQUENCE: 23

Ala Arg Ala Thr Ala Val Pro Lys Lys Ala Val Ala Lys Lys Ala Ala
1               5                   10                  15

Pro Lys Lys Thr Val Ala Lys Lys Ala
            20                  25

<210> SEQ ID NO 24
<211> LENGTH: 31
<212> TYPE: PRT
<213> ORGANISM: Trypanosoma brucei

<400> SEQUENCE: 24

Ala Arg Ala Thr Ala Val Pro Lys Lys Ala Val Ala Lys Lys Ala Ala
1               5                   10                  15

Pro Lys Lys Thr Val Ala Lys Lys Ala Ala Pro Lys Lys Ala Val
            20                  25                  30

<210> SEQ ID NO 25
<211> LENGTH: 24
<212> TYPE: PRT
<213> ORGANISM: Trypanosoma brucei

<400> SEQUENCE: 25

Ala Lys Lys Val Ala Pro Lys Lys Ala Val Ala Lys Lys Val Val Ala
1               5                   10                  15

Lys Lys Ala Val Ala Lys Lys Val
            20

<210> SEQ ID NO 26
<211> LENGTH: 30
<212> TYPE: PRT
<213> ORGANISM: Trypanosoma brucei
```

<400> SEQUENCE: 26

Val Ala Lys Lys Val Ala Pro Lys Lys Val Val Ala Lys Lys Val Ala
1               5                   10                  15

Pro Lys Lys Val Ala Gly Lys Lys Ala Ala Ala Lys Lys Ala
            20                  25                  30

<210> SEQ ID NO 27
<211> LENGTH: 26
<212> TYPE: PRT
<213> ORGANISM: Trypanosoma brucei

<400> SEQUENCE: 27

Val Ala Pro Lys Lys Val Val Ala Lys Lys Val Ala Pro Lys Lys Val
1               5                   10                  15

Ala Gly Lys Lys Ala Ala Ala Lys Lys Ala
            20                  25

<210> SEQ ID NO 28
<211> LENGTH: 681
<212> TYPE: DNA
<213> ORGANISM: Artificial Sequence
<220> FEATURE:
<223> OTHER INFORMATION: Synthetic construct (AlMV coat protein)

<400> SEQUENCE: 28

```
ggtaccatga gtgtcgacag ttcttcacaa aagaaagctg gtgggaaagc tggtaaacct      60
actaaacgtt ctcagaacta tgctgcctta cgcaaagctc aactgccgaa gcctccggcg     120
ttgaaagtcc cggttgtaaa accgacgaat actatactgc cacagacggg ctgcgtgtgg     180
caaagcctcg ggacccctct gagtctgagc tcttttaatg ggctcggcgt gagattcctc     240
tacagttttc tgaaggattt cgcgggacct cggatcctcg aagaggatct gatttacagg     300
atggtgtttt ccataacacc gtcctatgcc ggcacctttt gtctcactga tgacgtgacg     360
actgaggatg gtagggccgt tgcgcatggt aatcccatgc aagaatttcc tcatggcgcg     420
tttcacgcta atgagaagtt cgggtttgag ttggtcttca gctcctac ccatgcggga      480
atgcaaaacc aaaatttcaa gcattcctat gccgtagccc tctgtctgga cttcgacgcg     540
cagcctgagg atctaaaaa tccctcatac cgattcaacg aagtttgggt cgagagaaag     600
gcgttcccgc gagcagggcc cctccgcagt ttgattactg tggggctgct cgacgaagct     660
gacgatcttg atcgtcattg a                                              681
```

<210> SEQ ID NO 29
<211> LENGTH: 717
<212> TYPE: DNA
<213> ORGANISM: Artificial Sequence
<220> FEATURE:
<223> OTHER INFORMATION: Synthetic construct (LicKM)

<400> SEQUENCE: 29

```
ggatccttaa ttaaaatggg aggttcttat ccatataagt ctggtgagta tagaactaag      60
tctttctttg gatatggtta ttatgaagtt aggatgaagg ctgcaaagaa cgttggaatt     120
gtttcttctt tctttactta tactggacca tctgataaca acccatggga tgagattgat     180
attgagtttc ttggaaagga tactactaag gttcaattca actggtataa gaatggtgtt     240
ggtggaaacg agtatcttca taaccttgga tttgatgctt ctcaagattt tcatacttat     300
ggttttgagt ggagaccaga ttatattgat ttttatgttg atggaaagaa ggtttataga     360
ggtactagaa acattccagt tactcctgga aagattatga tgaatctttg gccaggaatt     420
```

```
ggtgttgatg aatggcttgg tagatatgat ggaagaactc cacttcaagc tgagtatgag     480
tatgttaagt attatccaaa cggtagatct gaattcaagc ttgttgttaa tactccattt     540
gttgctgttt tctctaactt tgattcttct caatgggaaa aggctgattg ggctaacggt     600
tctgttttta actgtgtttg gaagccatct caagttactt tttctaacgg aaagatgatt     660
cttactttgg atagagagta tgtcgaccat catcatcatc atcattgact cgagctc       717
```

<210> SEQ ID NO 30
<211> LENGTH: 230
<212> TYPE: PRT
<213> ORGANISM: Artificial Sequence
<220> FEATURE:
<223> OTHER INFORMATION: Synthetic construct (LicKM with 6X His-tag)

<400> SEQUENCE: 30

```
Met Gly Gly Ser Tyr Pro Tyr Lys Ser Gly Glu Tyr Arg Thr Lys Ser
 1               5                  10                  15

Phe Phe Gly Tyr Gly Tyr Tyr Glu Val Arg Met Lys Ala Ala Lys Asn
            20                  25                  30

Val Gly Ile Val Ser Ser Phe Phe Thr Tyr Thr Gly Pro Ser Asp Asn
        35                  40                  45

Asn Pro Trp Asp Glu Ile Asp Ile Glu Phe Leu Gly Lys Asp Thr Thr
    50                  55                  60

Lys Val Gln Phe Asn Trp Tyr Lys Asn Gly Val Gly Gly Asn Glu Tyr
65                  70                  75                  80

Leu His Asn Leu Gly Phe Asp Ala Ser Gln Asp Phe His Thr Tyr Gly
                85                  90                  95

Phe Glu Trp Arg Pro Asp Tyr Ile Asp Phe Tyr Val Asp Gly Lys Lys
            100                 105                 110

Val Tyr Arg Gly Thr Arg Asn Ile Pro Val Thr Pro Gly Lys Ile Met
        115                 120                 125

Met Asn Leu Trp Pro Gly Ile Gly Val Asp Glu Trp Leu Gly Arg Tyr
    130                 135                 140

Asp Gly Arg Thr Pro Leu Gln Ala Glu Tyr Glu Tyr Val Lys Tyr Tyr
145                 150                 155                 160

Pro Asn Gly Arg Ser Glu Phe Lys Leu Val Val Asn Thr Pro Phe Val
                165                 170                 175

Ala Val Phe Ser Asn Phe Asp Ser Ser Gln Trp Glu Lys Ala Asp Trp
            180                 185                 190

Ala Asn Gly Ser Val Phe Asn Cys Val Trp Lys Pro Ser Gln Val Thr
        195                 200                 205

Phe Ser Asn Gly Lys Met Ile Leu Thr Leu Asp Arg Glu Tyr Val Asp
    210                 215                 220

His His His His His His
225                 230
```

<210> SEQ ID NO 31
<211> LENGTH: 822
<212> TYPE: DNA
<213> ORGANISM: Artificial Sequence
<220> FEATURE:
<223> OTHER INFORMATION: Synthetic construct (LicKM with 6X His-tag, PR-1A, and KDEL)

<400> SEQUENCE: 31

```
ggatccttaa ttaaaatggg atttgttctc ttttcacaat gccttcatt tcttcttgtc       60
```

-continued

```
tctacacttc tcttattcct agtaatatcc cactcttgcc gtgcccaaaa tggaggttct      120
tatccatata agtctggtga gtatagaact aagtctttct ttggatatgg ttattatgaa      180
gttaggatga aggctgcaaa gaacgttgga attgtttctt ctttctttac ttatactgga      240
ccatctgata caacccatg ggatgagatt gatattgagt tcttggaaa ggatactact       300 aaggttcaat tcaactggta taagaatggt gttggtggaa acgagtatct tcataacctt      360
ggatttgatg cttctcaaga ttttcatact tatggttttg agtggagacc agattatatt      420 gattttatg ttgatggaaa gaaggtttat agaggtacta gaaacattcc agttactcct       480
ggaaagatta tgatgaatct ttggccagga attggtgttg atgaatggct tggtagatat      540
gatggaagaa ctccacttca agctgagtat gagtatgtta agtattatcc aaacggtaga      600
tctgaattca agcttgttgt taatactcca tttgttgctg ttttctctaa ctttgattct      660
tctcaatggg aaaaggctga ttgggctaac ggttctgttt taactgtgt ttggaagcca       720 tctcaagtta cttttctaa cggaaagatg attcttactt tggatagaga gtatgtcgac       780
catcatcatc atcatcataa ggatgaactt tgactcgagc tc                         822
```

<210> SEQ ID NO 32
<211> LENGTH: 265
<212> TYPE: PRT
<213> ORGANISM: Artificial Sequence
<220> FEATURE:
<223> OTHER INFORMATION: Synthetic construct (LicKM with 6X His-tag, PR-1A, and KDEL)

<400> SEQUENCE: 32

```
Met Gly Phe Val Leu Phe Ser Gln Leu Pro Ser Phe Leu Leu Val Ser
  1               5                  10                  15

Thr Leu Leu Phe Leu Val Ile Ser His Ser Cys Arg Ala Gln Asn
             20                  25                  30

Gly Gly Ser Tyr Pro Tyr Lys Ser Gly Glu Tyr Arg Thr Lys Ser Phe
         35                  40                  45

Phe Gly Tyr Gly Tyr Tyr Glu Val Arg Met Lys Ala Ala Lys Asn Val
     50                  55                  60

Gly Ile Val Ser Ser Phe Phe Thr Tyr Thr Gly Pro Ser Asp Asn Asn
 65                  70                  75                  80

Pro Trp Asp Glu Ile Asp Ile Glu Phe Leu Gly Lys Asp Thr Thr Lys
                 85                  90                  95

Val Gln Phe Asn Trp Tyr Lys Asn Gly Val Gly Gly Asn Glu Tyr Leu
            100                 105                 110

His Asn Leu Gly Phe Asp Ala Ser Gln Asp Phe His Thr Tyr Gly Phe
        115                 120                 125

Glu Trp Arg Pro Asp Tyr Ile Asp Phe Tyr Val Asp Gly Lys Lys Val
    130                 135                 140

Tyr Arg Gly Thr Arg Asn Ile Pro Val Thr Pro Gly Lys Ile Met Met
145                 150                 155                 160

Asn Leu Trp Pro Gly Ile Gly Val Asp Glu Trp Leu Gly Arg Tyr Asp
                165                 170                 175

Gly Arg Thr Pro Leu Gln Ala Glu Tyr Glu Tyr Val Lys Tyr Tyr Pro
            180                 185                 190

Asn Gly Arg Ser Glu Phe Lys Leu Val Val Asn Thr Pro Phe Val Ala
        195                 200                 205

Val Phe Ser Asn Phe Asp Ser Ser Gln Trp Glu Lys Ala Asp Trp Ala
    210                 215                 220
```

```
Asn Gly Ser Val Phe Asn Cys Val Trp Lys Pro Ser Gln Val Thr Phe
225                 230                 235                 240

Ser Asn Gly Lys Met Ile Leu Thr Leu Asp Arg Glu Tyr Val Asp His
            245                 250                 255

His His His His Lys Asp Glu Leu
        260                 265

<210> SEQ ID NO 33
<211> LENGTH: 451
<212> TYPE: PRT
<213> ORGANISM: Bos taurus

<400> SEQUENCE: 33

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Glu Ile Thr Asn Ala Cys Phe Glu Pro Ala Asn Gln Met Val Lys
    290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335
```

```
Thr Lys Arg Ser Ile Gln Phe Val Asp Trp Cys Pro Thr Gly Phe Lys
                340                 345                 350

Val Gly Ile Asn Tyr Gln Pro Pro Thr Val Pro Gly Gly Asp Leu
            355                 360                 365

Ala Lys Val Gln Arg Ala Val Cys Met Leu Ser Asn Thr Thr Ala Ile
370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Glu Gly
            435                 440                 445

Glu Glu Tyr
    450

<210> SEQ ID NO 34
<211> LENGTH: 451
<212> TYPE: PRT
<213> ORGANISM: Homo sapiens

<400> SEQUENCE: 34

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
            210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
```

```
                        245                 250                 255
Thr Asn Leu Val Pro Tyr Pro Arg Ile His Phe Pro Leu Ala Thr Tyr
                260                 265                 270

Ala Pro Val Ile Ser Ala Glu Lys Ala Tyr His Glu Gln Leu Ser Val
            275                 280                 285

Ala Glu Ile Thr Asn Ala Cys Phe Glu Pro Ala Asn Gln Met Val Lys
        290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Ser Ile Gln Phe Val Asp Trp Cys Pro Thr Gly Phe Lys
                340                 345                 350

Val Gly Ile Asn Tyr Gln Pro Pro Thr Val Val Pro Gly Gly Asp Leu
                355                 360                 365

Ala Lys Val Gln Arg Ala Val Cys Met Leu Ser Asn Thr Thr Ala Ile
            370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Gly
                435                 440                 445

Glu Glu Tyr
        450

<210> SEQ ID NO 35
<211> LENGTH: 451
<212> TYPE: PRT
<213> ORGANISM: Trypanosoma cruzi

<400> SEQUENCE: 35

Met Arg Glu Ala Ile Cys Ile His Ile Gly Gln Ala Gly Cys Gln Val
1               5                   10                  15

Gly Asn Ala Cys Trp Glu Leu Phe Cys Leu Glu His Gly Ile Gln Pro
            20                  25                  30

Asp Gly Ala Met Pro Ser Asp Lys Thr Ile Gly Val Glu Asp Asp Ala
        35                  40                  45

Phe Asn Thr Phe Phe Ser Glu Thr Gly Ala Gly Lys His Val Pro Arg
    50                  55                  60

Ala Val Phe Leu Asp Leu Glu Pro Thr Val Val Asp Glu Ile Arg Thr
65                  70                  75                  80

Gly Thr Tyr Arg Gln Leu Phe His Pro Glu Gln Leu Ile Ser Gly Lys
                85                  90                  95

Glu Asp Ala Ala Asn Asn Tyr Ala Arg Gly His Tyr Thr Ile Gly Lys
            100                 105                 110

Glu Ile Val Asp Leu Cys Leu Asp Arg Ile Arg Lys Leu Ala Asp Asn
        115                 120                 125

Cys Thr Gly Leu Gln Gly Phe Leu Val Tyr His Ala Val Gly Gly Gly
    130                 135                 140

Thr Gly Ser Gly Leu Gly Ala Leu Leu Leu Glu Arg Leu Ser Val Asp
145                 150                 155                 160
```

Tyr Gly Lys Lys Ser Lys Leu Gly Tyr Thr Val Tyr Pro Ser Pro Gln
          165                 170                 175

Val Ser Thr Ala Val Val Glu Pro Tyr Asn Ser Val Leu Ser Thr His
          180                 185                 190

Ser Leu Leu Glu His Thr Asp Val Ala Ala Met Leu Asp Asn Glu Ala
          195                 200                 205

Ile Tyr Asp Leu Thr Arg Arg Asn Leu Asp Ile Glu Arg Pro Thr Tyr
210                 215                 220

Thr Asn Leu Asn Arg Leu Ile Gly Gln Val Val Ser Ala Leu Thr Ala
225                 230                 235                 240

Ser Leu Arg Phe Asp Gly Ala Leu Asn Val Asp Leu Thr Glu Phe Gln
          245                 250                 255

Thr Asn Leu Val Pro Tyr Pro Arg Ile His Phe Val Leu Thr Ser Tyr
          260                 265                 270

Ala Pro Val Ile Ser Ala Glu Lys Ala Tyr His Glu Gln Leu Ser Val
          275                 280                 285

Ser Glu Ile Ser Asn Ala Val Phe Glu Pro Ala Ser Met Met Thr Lys
          290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
          325                 330                 335

Thr Lys Arg Thr Ile Gln Phe Val Asp Trp Ser Pro Thr Gly Phe Lys
          340                 345                 350

Cys Gly Ile Asn Tyr Gln Pro Pro Thr Val Val Pro Gly Gly Asp Leu
          355                 360                 365

Ala Lys Val Gln Arg Ala Val Cys Met Ile Ala Asn Ser Thr Ala Ile
370                 375                 380

Ala Glu Val Phe Ala Arg Ile Asp His Lys Phe Asp Leu Met Tyr Ser
385                 390                 395                 400

Lys Arg Ala Phe Val His Trp Tyr Val Gly Glu Gly Met Glu Glu Gly
          405                 410                 415

Glu Phe Ser Glu Ala Arg Glu Asp Leu Ala Ala Leu Glu Lys Asp Tyr
          420                 425                 430

Glu Glu Val Gly Ala Glu Ser Ala Asp Met Glu Gly Glu Glu Asp Val
          435                 440                 445

Glu Glu Tyr
       450

<210> SEQ ID NO 36
<211> LENGTH: 451
<212> TYPE: PRT
<213> ORGANISM: Trypanosoma danilewskyi

<400> SEQUENCE: 36

Met Arg Glu Ala Ile Cys Ile His Ile Gly Gln Ala Gly Cys Gln Val
1               5                   10                  15

Gly Asn Ala Cys Trp Glu Leu Phe Cys Leu Glu His Gly Ile Gln Pro
            20                  25                  30

Asp Gly Ala Met Pro Ser Asp Lys Thr Ile Gly Val Glu Asp Asp Ala
        35                  40                  45

Phe Asn Thr Phe Phe Ser Glu Thr Gly Ala Gly Lys His Val Pro Arg
    50                  55                  60

Ala Val Phe Leu Asp Leu Glu Pro Thr Val Val Asp Glu Ile Arg Thr
65                  70                  75                  80

```
Gly Thr Tyr Arg Gln Leu Phe His Pro Glu Gln Leu Ile Ser Gly Lys
                85                  90                  95

Glu Asp Ala Ala Asn Asn Tyr Ala Arg Gly His Tyr Thr Ile Gly Lys
            100                 105                 110

Glu Ile Val Asp Leu Cys Leu Asp Arg Ile Arg Lys Leu Ala Asp Asn
        115                 120                 125

Cys Thr Gly Leu Gln Gly Phe Leu Val Tyr His Ala Val Gly Gly Gly
    130                 135                 140

Thr Gly Ser Gly Leu Gly Ala Leu Leu Glu Arg Leu Ser Val Asp
145                 150                 155                 160

Tyr Gly Lys Lys Ser Lys Leu Gly Tyr Thr Val Tyr Pro Ser Pro Gln
                165                 170                 175

Val Ser Thr Ala Val Val Glu Pro Tyr Asn Ser Val Leu Ser Thr His
            180                 185                 190

Ser Leu Leu Glu His Thr Asp Val Ala Ala Met Leu Asp Asn Glu Ala
        195                 200                 205

Ile Tyr Asp Leu Thr Arg Arg Asn Leu Asp Ile Glu Arg Pro Thr Tyr
    210                 215                 220

Thr Asn Leu Asn Arg Leu Ile Ala Gln Val Val Ser Ser Leu Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Val Leu Thr Ser Tyr
            260                 265                 270

Ala Pro Val Ile Ser Ala Glu Lys Ala Tyr His Glu Gln Leu Ser Val
        275                 280                 285

Ser Glu Ile Ser Asn Ala Val Phe Glu Pro Ala Ser Met Met Thr Lys
    290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
                325                 330                 335

Thr Lys Arg Thr Ile Gln Phe Val Asp Trp Ser Pro Thr Gly Phe Lys
            340                 345                 350

Cys Gly Ile Asn Tyr Gln Pro Pro Thr Val Val Pro Gly Gly Asp Leu
        355                 360                 365

Ala Lys Val Gln Arg Ala Val Cys Met Ile Ala Asn Ser Thr Ala Ile
    370                 375                 380

Ala Glu Val Phe Ala Arg Ile Asp His Lys Phe Asp Leu Met Tyr Ser
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
            420                 425                 430

Glu Glu Val Gly Ala Glu Ser Gly Asp Leu Glu Gly Glu Glu Asp Val
        435                 440                 445

Glu Glu Tyr
    450

<210> SEQ ID NO 37
<211> LENGTH: 451
<212> TYPE: PRT
<213> ORGANISM: Trypanosoma grayi
<220> FEATURE:
```

<221> NAME/KEY: VARIANT
<222> LOCATION: 326, 352
<223> OTHER INFORMATION: Xaa = Any Amino Acid

<400> SEQUENCE: 37

```
Met Arg Glu Ala Ile Cys Ile His Ile Gly Gln Ala Gly Cys Gln Val
  1               5                  10                  15

Gly Asn Ala Cys Trp Glu Leu Phe Cys Leu Glu His Gly Ile Gln Pro
             20                  25                  30

Asp Gly Ala Met Pro Ser Asp Lys Thr Ile Gly Ala Glu Asp Asp Ala
         35                  40                  45

Phe Asn Thr Phe Phe Ser Glu Thr Gly Ala Gly Lys His Val Pro Arg
 50                  55                  60

Ala Val Phe Leu Asp Leu Glu Pro Thr Val Val Asp Glu Ile Arg Thr
 65                  70                  75                  80

Gly Thr Tyr Arg Gln Leu Phe His Pro Glu Gln Leu Ile Thr Gly Lys
                 85                  90                  95

Glu Asp Ala Ala Asn Asn Tyr Ala Arg Gly His Tyr Thr Ile Gly Lys
            100                 105                 110

Glu Ile Val Asp Leu Cys Leu Asp Arg Ile Arg Lys Leu Ala Asp Asn
            115                 120                 125

Cys Thr Gly Leu Gln Gly Phe Leu Val Tyr His Ala Val Gly Gly Gly
        130                 135                 140

Thr Gly Ser Gly Leu Gly Ala Leu Leu Leu Glu Arg Leu Ser Val Asp
145                 150                 155                 160

Tyr Gly Lys Lys Ser Lys Leu Gly Tyr Thr Val Tyr Pro Ser Pro Gln
                165                 170                 175

Val Ser Thr Ala Val Val Glu Pro Tyr Asn Ser Val Leu Ser Thr His
            180                 185                 190

Ser Leu Leu Glu His Thr Asp Val Ala Ala Met Leu Asp Asn Glu Ala
        195                 200                 205

Ile Tyr Asp Leu Thr Arg Arg Asn Leu Asp Ile Glu Arg Pro Thr Tyr
    210                 215                 220

Thr Asn Leu Asn Arg Leu Ile Ala Gln Val Val Ser Ser Leu Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Val Leu Thr Ser Tyr
            260                 265                 270

Ala Pro Val Ile Ser Ala Glu Lys Ala Tyr His Glu Gln Leu Ser Val
        275                 280                 285

Ser Glu Ile Ser Asn Ala Val Phe Glu Pro Ala Ser Met Met Thr Lys
    290                 295                 300

Cys Asp Pro Arg His Gly Lys Tyr Met Ala Cys Cys Leu Met Tyr Arg
305                 310                 315                 320

Gly Asp Val Val Pro Xaa Asp Val Asn Ala Ala Val Ala Thr Ile Lys
                325                 330                 335

Thr Lys Arg Thr Ile Gln Phe Val Asp Trp Ser Pro Thr Gly Phe Xaa
            340                 345                 350

Cys Gly Ile Asn Tyr Gln Pro Pro Thr Val Val Pro Gly Gly Asp Leu
        355                 360                 365

Ala Lys Val Gln Arg Ala Val Cys Met Ile Ala Asn Ser Thr Ala Ile
    370                 375                 380

Ala Glu Val Phe Ala Arg Ile Asp His Lys Phe Asp Leu Met Tyr Ser
```

```
                385                 390                 395                 400
Lys Arg Ala Phe Val His Trp Tyr Val Gly Glu Gly Met Glu Glu Gly
                        405                 410                 415

Glu Phe Ser Glu Ala Arg Glu Asp Leu Ala Ala Leu Glu Lys Asp Tyr
                420                 425                 430

Glu Glu Val Gly Ala Glu Ser Ala Asp Met Glu Gly Glu Glu Asp Val
            435                 440                 445

Glu Glu Tyr
    450

<210> SEQ ID NO 38
<211> LENGTH: 441
<212> TYPE: PRT
<213> ORGANISM: Trypanosoma cruzi

<400> SEQUENCE: 38

Arg Glu Ile Val Cys Val Gln Ala Gly Gln Cys Gly Asn Gln Ile Gly
1               5                   10                  15

Ser Lys Phe Trp Glu Val Ile Ser Asp Glu His Gly Val Asp Pro Thr
            20                  25                  30

Gly Thr Tyr Gln Gly Asp Ser Asp Leu Gln Leu Glu Arg Ile Asn Val
        35                  40                  45

Tyr Phe Asp Glu Ala Thr Gly Gly Arg Tyr Val Pro Arg Ala Val Leu
    50                  55                  60

Ile Asp Leu Glu Pro Gly Thr Met Asp Ser Val Arg Ala Gly Pro Tyr
65                  70                  75                  80

Gly Gln Ile Phe Arg Pro Asp Asn Phe Ile Phe Gly Gln Ser Gly Ala
                85                  90                  95

Gly Asn Asn Trp Ala Lys Gly His Tyr Thr Glu Gly Ala Glu Leu Ile
            100                 105                 110

Asp Ser Val Leu Asp Val Cys Arg Lys Glu Ala Glu Ser Cys Asp Cys
        115                 120                 125

Leu Gln Gly Phe Gln Ile Cys His Ser Leu Gly Gly Gly Thr Gly Ser
    130                 135                 140

Gly Met Gly Thr Leu Leu Ile Ser Lys Leu Arg Glu Glu Tyr Pro Asp
145                 150                 155                 160

Arg Ile Met Met Thr Phe Ser Ile Ile Pro Ser Pro Lys Val Ser Asp
                165                 170                 175

Thr Val Val Glu Pro Tyr Asn Thr Thr Leu Ser Val His Gln Leu Val
            180                 185                 190

Glu Asn Ser Asp Glu Ser Met Cys Ile Asp Asn Glu Ala Leu Tyr Asp
        195                 200                 205

Ile Cys Phe Arg Thr Leu Lys Leu Thr Thr Pro Thr Phe Gly Asp Leu
    210                 215                 220

Asn His Leu Val Ser Ala Val Ser Gly Val Thr Cys Cys Leu Arg
225                 230                 235                 240

Phe Pro Gly Gln Leu Asn Ser Asp Leu Arg Lys Leu Ala Val Asn Leu
                245                 250                 255

Val Pro Phe Pro Arg Leu His Phe Phe Met Met Gly Phe Ala Pro Leu
            260                 265                 270

Ser Ser Arg Gly Ser Gln Gln Tyr Arg Gly Leu Ser Val Pro Asp Val
        275                 280                 285

Thr Gln Gln Met Phe Asp Ala Lys Asn Met Met Gln Ala Ala Asp Pro
    290                 295                 300
```

```
Ala His Gly Arg Tyr Leu Thr Ala Ser Ala Leu Phe Arg Gly Arg Met
305                 310                 315                 320

Ser Thr Lys Glu Val Asp Glu Gln Met Leu Asn Val Gln Asn Lys Asn
                325                 330                 335

Ser Ser Tyr Phe Ile Glu Trp Ile Pro Asn Asn Ile Lys Ser Ser Ile
            340                 345                 350

Cys Asp Ile Pro Pro Lys Gly Leu Lys Met Ala Val Thr Phe Val Gly
        355                 360                 365

Asn Asn Thr Cys Ile Gln Glu Met Phe Arg Arg Val Gly Glu Gln Phe
    370                 375                 380

Thr Ala Met Phe Arg Arg Lys Ala Phe Leu His Trp Tyr Thr Gly Glu
385                 390                 395                 400

Gly Met Asp Glu Met Glu Phe Thr Glu Ala Glu Ser Asn Met Asn Asp
                405                 410                 415

Leu Val Ser Glu Tyr Gln Gln Tyr Gln Asp Ala Thr Ile Glu Glu Glu
            420                 425                 430

Gly Glu Phe Asp Glu Glu Gln Tyr
            435                 440

<210> SEQ ID NO 39
<211> LENGTH: 398
<212> TYPE: PRT
<213> ORGANISM: Trypanosoma cyclops

<400> SEQUENCE: 39

Met Arg Glu Ile Val Cys Ile Gln Ala Gly Gln Cys Gly Asn Gln Ile
1               5                   10                  15

Gly Ser Lys Phe Trp Glu Val Ile Ser Asp Glu His Gly Val Asp Pro
                20                  25                  30

Thr Gly Thr Tyr Gln Gly Asp Ser Asp Leu Gln Leu Glu Arg Ile Asn
            35                  40                  45

Val Tyr Phe Asp Glu Ala Thr Gly Gly Arg Tyr Val Pro Arg Ala Val
        50                  55                  60

Leu Ile Asp Leu Glu Pro Gly Thr Met Asp Ser Val Arg Ala Gly Pro
65                  70                  75                  80

Tyr Gly Gln Val Phe Arg Pro Asp Asn Phe Ile Phe Gly Gln Ser Gly
                85                  90                  95

Ala Gly Asn Asn Trp Ala Lys Gly His Tyr Thr Glu Gly Ala Glu Leu
            100                 105                 110

Ile Asp Ser Val Leu Asp Val Cys Arg Lys Glu Ala Glu Ser Cys Asp
        115                 120                 125

Cys Leu Gln Gly Phe Gln Ile Ala His Ser Leu Gly Gly Gly Thr Gly
    130                 135                 140

Ser Gly Met Gly Thr Leu Leu Ile Ser Lys Leu Arg Glu Glu Tyr Pro
145                 150                 155                 160

Asp Arg Ile Met Met Thr Phe Ser Ile Ile Pro Ser Pro Lys Val Ser
                165                 170                 175

Asp Thr Val Val Glu Pro Tyr Asn Thr Thr Leu Ser Val His Gln Leu
            180                 185                 190

Val Glu Asn Ser Asp Glu Ser Met Cys Ile Asp Asn Glu Ala Leu Tyr
        195                 200                 205

Asp Ile Cys Phe Arg Thr Leu Lys Leu Thr Thr Pro Thr Phe Gly Asp
    210                 215                 220

Leu Asn His Leu Val Ser Ala Val Met Ser Gly Val Thr Cys Cys Leu
225                 230                 235                 240
```

```
Arg Phe Pro Gly Gln Leu Asn Ser Asp Leu Arg Lys Leu Ala Val Asn
                245                 250                 255
Leu Val Pro Phe Pro Arg Leu His Phe Phe Met Met Gly Phe Ala Pro
            260                 265                 270
Leu Thr Ser Arg Gly Ser Gln Gln Tyr Arg Gly Leu Ser Val Pro Glu
        275                 280                 285
Leu Thr Gln Gln Met Phe Asp Ala Lys Asn Met Met Gln Ala Ala Asp
    290                 295                 300
Pro Arg His Gly Arg Tyr Leu Thr Ala Ser Ala Leu Phe Arg Gly Arg
305                 310                 315                 320
Met Ser Thr Lys Glu Val Asp Glu Gln Met Leu Asn Val Leu Asn Lys
                325                 330                 335
Asn Ser Ser Tyr Phe Ile Glu Trp Ile Pro Asn Asn Ile Lys Ser Ser
            340                 345                 350
Ile Cys Asp Ile Pro Pro Lys Gly Leu Lys Met Ala Val Thr Phe Ile
        355                 360                 365
Gly Asn Asn Thr Cys Ile Gln Glu Met Phe Arg Arg Val Gly Glu Gln
    370                 375                 380
Phe Thr Ala Met Phe Arg Arg Lys Ala Phe Leu His Trp Tyr
385                 390                 395

<210> SEQ ID NO 40
<211> LENGTH: 442
<212> TYPE: PRT
<213> ORGANISM: Trypanosoma danilewskyi

<400> SEQUENCE: 40

Met Arg Glu Ile Val Cys Val Gln Ala Gly Gln Cys Gly Asn Gln Ile
1               5                   10                  15
Gly Ser Lys Phe Trp Glu Val Ile Ser Asp Glu His Gly Val Asp Pro
                20                  25                  30
Thr Gly Thr Tyr Gln Gly Asp Ser Asp Leu Gln Leu Glu Arg Ile Asn
            35                  40                  45
Val Tyr Phe Asp Glu Ala Thr Gly Gly Arg Tyr Val Pro Arg Ala Val
50                  55                  60
Leu Ile Asp Leu Glu Pro Gly Thr Met Asp Ser Val Arg Ala Gly Pro
65                  70                  75                  80
Tyr Gly Gln Ile Phe Arg Pro Asp Asn Phe Ile Phe Gly Gln Ser Gly
                85                  90                  95
Ala Gly Asn Asn Trp Ala Lys Gly His Tyr Thr Glu Gly Ala Glu Leu
            100                 105                 110
Ile Asp Ser Val Leu Asp Val Cys Arg Lys Glu Ala Glu Ser Cys Asp
        115                 120                 125
Cys Leu Gln Gly Phe Gln Ile Ala His Ser Leu Gly Gly Gly Thr Gly
    130                 135                 140
Ser Gly Met Gly Thr Leu Leu Ile Ser Lys Leu Arg Glu Glu Tyr Pro
145                 150                 155                 160
Asp Arg Ile Met Met Thr Phe Ser Ile Ile Pro Ser Pro Lys Val Ser
                165                 170                 175
Asp Thr Val Val Glu Pro Tyr Asn Thr Thr Leu Ser Val His Gln Leu
            180                 185                 190
Val Glu Asn Ser Asp Glu Ser Met Cys Ile Asp Asn Glu Ala Leu Tyr
        195                 200                 205
Asp Ile Cys Phe Arg Thr Leu Lys Leu Thr Thr Pro Thr Phe Gly Asp
```

```
                  210                 215                 220
Leu Asn His Leu Val Ser Ala Val Met Ser Gly Val Thr Cys Cys Leu
225                 230                 235                 240

Arg Phe Pro Gly Gln Leu Asn Ser Asp Leu Arg Lys Leu Ala Val Asn
                245                 250                 255

Leu Val Pro Phe Pro Arg Leu His Phe Met Met Gly Phe Ala Pro
                260                 265                 270

Leu Thr Ser Arg Gly Ser Gln Gln Tyr Arg Gly Leu Ser Val Pro Glu
                275                 280                 285

Leu Thr Gln Gln Met Phe Asp Ala Lys Asn Met Met Gln Ala Ala Glu
                290                 295                 300

Pro Arg His Gly Arg Tyr Leu Thr Ala Ser Ala Leu Phe Arg Gly Arg
305                 310                 315                 320

Met Ser Thr Lys Glu Ile Asp Glu Gln Met Leu Asn Val Gln Asn Lys
                325                 330                 335

Asn Ser Ser Tyr Phe Ile Glu Trp Ile Pro Asn Asn Ile Lys Ser Ser
                340                 345                 350

Ile Cys Asp Ile Pro Pro Lys Gly Leu Lys Met Ala Val Thr Phe Ile
                355                 360                 365

Gly Asn Asn Thr Cys Ile Gln Glu Met Phe Arg Arg Val Gly Glu Gln
                370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Val Glu Glu
                420                 425                 430

Glu Gly Glu Phe Asp Glu Glu Gln Tyr
                435                 440

<210> SEQ ID NO 41
<211> LENGTH: 445
<212> TYPE: PRT
<213> ORGANISM: Bos taurus

<400> SEQUENCE: 41

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
                20                  25                  30

Thr Gly Ser Tyr His Gly Asp Ser Asp Leu Gln Leu Glu Arg Ile Asn
                35                  40                  45

Val Tyr Tyr Asn Glu Ala Thr Gly Asn Lys Tyr Val Pro Arg Ala Ile
            50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
                100                 105                 110

Val Asp Ser Val Leu Asp Val Val Arg Lys Glu Ser Glu Ser Cys Asp
                115                 120                 125

Cys Leu Gln Gly Phe Gln Leu Thr His Ser Leu Gly Gly Gly Thr Gly
            130                 135                 140
```

Ser Gly Met Gly Thr Leu Leu Ile Ser Lys Ile Arg Glu Glu Tyr Pro
145                 150                 155                 160

Asp Arg Ile Met Asn Thr Phe Ser Val Met Pro Ser Pro Lys Val Ser
            165                 170                 175

Asp Thr Val Val Glu Pro Tyr Asn Ala Thr Leu Ser Val His Gln Leu
            180                 185                 190

Val Glu Asn Thr Asp Glu Thr Tyr Ser Ile Asp Asn Glu Ala Leu Tyr
            195                 200                 205

Asp Ile Cys Phe Arg Thr Leu Lys Leu Thr Thr Pro Thr Tyr Gly Asp
            210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
            245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
            275                 280                 285

Leu Thr Gln Gln Met Phe Asp Ser Lys Asn Met Met Ala Ala Cys Asp
            290                 295                 300

Pro Arg His Gly Arg Tyr Leu Thr Val Ala Ala Ile Phe Arg Gly Arg
305                 310                 315                 320

Met Ser Met Lys Glu Val Asp Glu Gln Met Leu Asn Val Gln Asn Lys
            325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ser Ala Thr Phe Ile
            355                 360                 365

Gly Asn Ser Thr Ala Ile Gln Glu Leu Phe Lys Arg Ile Ser Glu Gln
            370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
            405                 410                 415

Asp Leu Val Ser Glu Tyr Gln Gln Tyr Gln Asp Ala Thr Ala Asp Glu
            420                 425                 430

Gln Gly Glu Phe Glu Glu Glu Gly Glu Asp Glu Ala
            435                 440                 445

<210> SEQ ID NO 42
<211> LENGTH: 445
<212> TYPE: PRT
<213> ORGANISM: Homo sapiens

<400> SEQUENCE: 42

Met Arg Glu Ile Val His Leu Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Glu Arg Ile Asn
            35                  40                  45

Val Tyr Tyr Asn Glu Ala Thr Gly Gly Lys Tyr Val Pro Arg Ala Val
            50                  55                  60

Leu Val Asp Leu Glu Pro Gly Thr Met Asp Ser Val Arg Ser Gly Pro
65                  70                  75                  80

```
Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
                100                 105                 110

Val Asp Ser Val Leu Asp Val Val Arg Lys Glu Ala Glu Ser Cys Asp
                115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
                180                 185                 190

Val Glu Asn Thr Asp Glu Thr Tyr Cys Ile Asp Asn Glu Ala Leu Tyr
                195                 200                 205

Asp Ile Cys Phe Arg Thr Leu Lys Leu Thr Thr Pro Thr Tyr Gly Asp
        210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
                260                 265                 270

Leu Thr Ser Arg Gly Ser Gln Tyr Arg Ala Leu Thr Val Pro Glu
                275                 280                 285

Leu Thr Gln Gln Met Phe Asp Ala Lys Asn Met Met Ala Ala Cys Asp
        290                 295                 300

Pro Arg His Gly Arg Tyr Leu Thr Val Ala Ala Ile Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
                340                 345                 350

Val Cys Asp Ile Pro Pro Arg Gly Leu Lys Met Ser Ala Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
                420                 425                 430

Glu Gly Glu Phe Glu Glu Glu Ala Glu Glu Val Ala
                435                 440                 445
```